US009868679B2

(12) United States Patent
Murray et al.

(10) Patent No.: US 9,868,679 B2
(45) Date of Patent: Jan. 16, 2018

(54) PROCESS FOR ISOMERIZATION AND DECARBOXYLATION OF UNSATURATED ORGANIC COMPOUNDS WITH A METAL CATALYST OR CATALYST PRECURSOR

(71) Applicant: The United States of America, as represented by the Secretary of Agriculture, Washington, DC (US)

(72) Inventors: Rex E. Murray, Peoria, IL (US); Kenneth M. Doll, Peoria, IL (US); Zengshe Liu, Morton, IL (US)

(73) Assignee: THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 1 day.

(21) Appl. No.: 14/203,686

(22) Filed: Mar. 11, 2014

(65) Prior Publication Data
US 2014/0275592 A1 Sep. 18, 2014

Related U.S. Application Data

(60) Provisional application No. 61/788,192, filed on Mar. 15, 2013.

(51) Int. Cl.
| | |
|---|---|
| C07C 51/00 | (2006.01) |
| C07C 1/207 | (2006.01) |
| C07C 51/353 | (2006.01) |
| C07C 6/04 | (2006.01) |
| C07C 2/22 | (2006.01) |
| C11C 3/14 | (2006.01) |
| C07C 67/333 | (2006.01) |
| C10G 50/00 | (2006.01) |
| C10G 3/00 | (2006.01) |

(52) U.S. Cl.
CPC .......... *C07C 1/2078* (2013.01); *C07C 2/22* (2013.01); *C07C 6/04* (2013.01); *C07C 51/353* (2013.01); *C07C 67/333* (2013.01); *C10G 3/47* (2013.01); *C10G 50/00* (2013.01); *C11C 3/14* (2013.01); *C07C 2521/06* (2013.01); *C07C 2527/12* (2013.01); *C07C 2527/13* (2013.01); *C07C 2531/20* (2013.01); *C07C 2531/24* (2013.01)

(58) Field of Classification Search
CPC .................................................. C07C 2523/46
See application file for complete search history.

(56) References Cited

U.S. PATENT DOCUMENTS

| | | | |
|---|---|---|---|
| 4,138,411 A | 2/1979 | Gandilhon | |
| 5,077,447 A | 12/1991 | Miller et al. | |
| 5,719,301 A * | 2/1998 | Sleeter | 554/24 |
| 6,455,716 B2 * | 9/2002 | Kenneally et al. | 554/158 |
| 2006/0161032 A1 | 7/2006 | Murzin et al. | |
| 2007/0281875 A1 | 12/2007 | Scheibel et al. | |
| 2011/0105817 A1 | 5/2011 | Zwijnenburg et al. | |

FOREIGN PATENT DOCUMENTS

WO 2011/126688 A1 10/2011

OTHER PUBLICATIONS

Ohlmann et al. J. Am. Chem. Soc. 2012 (published Jul. 20, 2012), 134, 13716-13729.*
Mol. Green Chemistry, 2002, 4, 5-13.*
Chorfa et al. Applied Catalysis A: General 387 (2010) 75-86.*
Salvini, Antonella, et al., "Alkene isomerization by non-hydridic phosphine substituted ruthenium carbonyl carboxylates", Journal of Molecular Catalysis A: Chemical, 159, 2000, pp. 185-195.
Gao, Yuan, et al., "An efficient binuclear catalyst for decomposition of formic acid", Chem. Commun., 1998, pp. 2365-2366.
Basu, Amitabha, et al., "Metal Clusters in Homogeneous Catalysis: Isomerization of Methyl Linoleate*", Journal of Molecular Catalysis, 38, 1986, pp. 315-321.
Czaun, Miklos, et al., "Hydrogen Generation from Formic Acid Decomposition by Ruthenium Carbonyl Complexes. Tetraruthenium Dodecacarbonyl Tetrahydride as an Active Intermediate", ChemSusChem, 2011, 4, pp. 1241-1248.
Castiglioni, M., et al., "Reactions of Dodecacarbonyltriruthenium with Pentenes", Inorganic Chemistry, vol. 15, No. 2, 1976, pp. 394-396.
Mukesh, Doble, et al., "Kinetics and Mathematical Modeling of Isomerization of Methyl Linoleate on Ruthenium Catalyust. 1. Conjugation and Hydrogenation", Ind. Eng. Chem. Prod. Res. Dev., vol. 24, No. 2, 1985, pp. 318-323.
Grotjahn, Douglas B., "Extensive Isomerization of Alkenes Using a Bifunctional Catalyst: An Alkene Zipper", J. Am. Chem. Soc., vol. 129, No. 31, 2007, pp. 9592-9593.
Erdogan, Gulin, et al., "Mild and Selective Deutereation adn Isomerization of Alkenes by a Bifunctional Catalyst and Deuterium Oxide", J. Am. Chem., Soc., vol. 131, No. 30, 2009, pp. 10354-10355.
Narasimhan, Srinivasa, et al., "Kinetics and Mathematical Modeling of Isomerization of Methyl Linoleate on Ruthenium Catalyst. 2. Conjugation and Polymerization", Ind. Eng. Chem. Prod. Res. Dev., 1985, 24, pp. 324-326.

(Continued)

*Primary Examiner* — Clinton A Brooks
*Assistant Examiner* — Ana Z Muresan
(74) *Attorney, Agent, or Firm* — John D. Fado; G. Byron Stover

(57) ABSTRACT

Disclosed is a method for using a metal catalyst or catalyst precursor that catalyzes the isomerization of an unsaturated fatty acid, unsaturated fatty acid derivative, or an unsaturated triglyceride. Also disclosed is a method for using a metal catalyst or catalyst precursor that catalyzes the decarboxylation of an unsaturated organic compound. Also disclosed is a method for using a catalyst or catalyst precursor for the dual function isomerization and decarboxylation of an unsaturated fatty acid to an unsaturated organic compound.

24 Claims, 70 Drawing Sheets

(56) References Cited

OTHER PUBLICATIONS

Narasimhan, C. S., et al., "Isomerisation of Metyhyl Linoleate on Ruthenium (III)-Alkoxide Complex", Journal of Molecular Catalysis, 52, 1989, pp. 305-309.
Sherlock, Stephen J., et al., "A Convenient Route to an Uncommon Class of Polymeric and Binuclear Ruthenium (I) Complexes Containing Diphosphine and Dithioether Ligands", Organometallics, 1988, vol. 7, No. 7, pp. 1663-1666.
Pertici, Paolo, et al., "( nano6-Naphthalene)(nano4-cycloocta-1,5-diene)ruthenium(0) as efficient catalytic precursor for the isomerization of methyl linoleate under mild conditions", Journal of Molecular Catalysis A: Chemical, 144, 1999, pp. 7-13.
Muetterties, E.L., "Molecular Metal Clusters", Science, May 20, 1977, vol. 196, No. 4292, pp. 839-848.
Sivaramakrishna, Akella, et al., "Selective Isomerization of 1-alkenes by binary metal carbonyl compounds", Polyhedron, 27, 2008, pp. 1911-1916.

* cited by examiner

The decarboxylation and isomerization of 10-undecenoic acid with $Ru_3(CO)_{12}$ ran over multiple days, with added eicosane, in a reactive distillation, day 2 product The decarboxylation and isomerization of 10-undecenoic acid with $Ru_3(CO)_{12}$ ran over multiple days, with added eicosane, in a reactive distillation, day 4 product The decarboxylation and isomerization of 9-cis-octadecenoic acid with Bis(tricyclohexylphosphine) isopentenylidene dichlororuthenium, at 250 °C for 4 hours The transformation of R-12-hydroxy-9-cis-octadecenoic acid with $Ru_3(CO)_{12}$ at 250 °C for 4 hours.

The transformation of R-12-hydroxy-9-cis-octadecenoic acid with Ru$_3$(CO)$_{12}$ at 250 °C for 24 hours.

NMR Tiolein, 4 hours reaction

NMR Triolein, starting material.

¹H NMR soybean oil 24 hour reaction, 125 °C

¹H NMR soybean oil 24 hour reaction, 175 °C $^1$H NMR soybean oil 24 hour control experiment, 175 °C.

Mixed catalyst, 4 hours

Mixed catalyst, 24 hours $^1$H NMR spectrum of the isomerized octadecene from Example 10, used as a starting material in Example 47

$^{13}$C NMR spectrum of the isomerized octadecene from Example 10, using starting material of Example 47

¹H NMR spectrum of the polymerized isomerized octadecene of Example 47

$^{13}$C NMR spectrum of the polymerized isomerized octadecene of Example 47

GC-FID chromatogram of the cross metathesis reaction of isomerized heptadecene showing a mixture of isomers of alkenes of various size GC-FID chromatogram of isomerized methyl cis-9-octadecene after a metathesis reaction with ethane

PROCESS FOR ISOMERIZATION AND DECARBOXYLATION OF UNSATURATED ORGANIC COMPOUNDS WITH A METAL CATALYST OR CATALYST PRECURSOR

CROSS-REFERENCE TO RELATED APPLICATION

This present application claims priority under 35 U.S.C. §119(e) to U.S. Provisional Ser. No. 61/788,192, which was filed on Mar. 15, 2013, and is hereby incorporated by reference.

FIELD OF INVENTION

This invention relates to the use of a metal catalyst or catalyst precursor that catalyzes the isomerization of an unsaturated fatty acid, unsaturated fatty acid derivative, alkene, or an unsaturated triglyceride. Also disclosed is the use of a metal catalyst or catalyst precursor that catalyzes the decarboxylation of an unsaturated organic compound. Also disclosed is the use of a catalyst or catalyst precursor for the dual function isomerization and decarboxylation of an unsaturated fatty acid to an unsaturated organic compound.

BACKGROUND OF INVENTION

Research has focused on the process of converting bio-based fatty acids and their derivatives to olefins or isomerized fatty compounds for valuable industrial applications. Preferably, this process would utilize a low cost feedstock material such as unsaturated fatty acids, carboxylic acids, unsaturated fatty acid derivatives, alkenes, and convert said reactants to a more commercially desirable product. Such desirable products include isomerized olefins, α-olefins, and decarboxylated products.

In order to facilitate the isomerization of the alkene reactant, there is a need to develop a low-cost catalyst and catalyst precursor compounds to lower the activation energy of such a reaction and generate desirable commercial end products. Preferably, the catalyst would facilitate both the decarboxylation and isomerization of feedstock material to generate the desirable end product. Alternatively, the catalyst would either isomerize or decarboxylate feedstock material. Preferably the catalyst would be low cost material and have a high turnover number.

BRIEF SUMMARY OF THE INVENTION

Disclosed herein is a process for the production of an isomerized unsaturated organic compound, the process comprising contacting an unsaturated fatty acid, unsaturated fatty acid derivative, or an unsaturated triglyceride in the presence of a catalyst or catalyst precursor containing ruthenium or osmium at a temperature at which isomerization occurs and recovering the isomerized unsaturated organic compound product, wherein the isomerization does not require the step of adding a carboxylic acid anhydride and the catalyst or catalyst precursor does not contain a phosphine ligand.

In an embodiment of the invention, the process for the production of an isomerized unsaturated organic compound comprises an additional step of contacting an additional acid to an unsaturated fatty acid, unsaturated fatty acid derivative, or an unsaturated triglyceride in the presence of a catalyst or catalyst precursor. In another embodiment, the additional acid is a monocarboxylic acid. In yet another embodiment of the invention, the monocarboxylic acid is benzoic acid, cinnamic acid, propanoic acid, undecanoic acid, acetic acid, stearic acid, or oleic acid.

In an embodiment of the invention, the process for the production of an isomerized unsaturated organic compound utilizes a catalyst or catalyst precursor containing both ruthenium and osmium compounds. In another embodiment of the invention, the catalyst or catalyst precursor is selected from the group consisting of ruthenium carbonyl or ruthenium chloride. In yet another embodiment of the invention, the catalyst or catalyst precursor is osmium carbonyl.

In another embodiment of the invention, the process for the production of an isomerized unsaturated organic compound yields an olefin. In one embodiment of the invention, the disclosed isomerization process yields an isomerized unsaturated organic compound product having a mixture of internal and α-olefins. In yet another embodiment of the invention, the isomerization process yields an isomerized unsaturated organic compound product having a conjugated internal olefin.

In yet another embodiment of the invention, the process for the production of an isomerized unsaturated organic compound yields an olefin wherein the olefin is further subject to an oligomerization or a polymerization reaction. In one aspect of invention, the olefin product from the isomerization process is further subject to a metathesis reaction.

Disclosed herein a process for the production of a decarboxylated unsaturated organic compound, the process comprising contacting a carboxylic acid in the presence of a catalyst or catalyst precursor containing ruthenium or osmium at a temperature at which decarboxylation occurs and recovering the decarboxylated unsaturated organic compound product, wherein the decarboxylation does not require the step of adding a carboxylic acid anhydride.

In an embodiment of the invention, the process for the production of a decarboxylated unsaturated carboxylic acid comprises the additional step of contacting an additional acid to the carboxylic acid in the presence of a catalyst or catalyst precursor. In another embodiment, the additional acid is a monocarboxylic acid. In yet another embodiment of the invention, the monocarboxylic acid is benzoic acid, cinnamic acid, acetic acid, undecanoic acid, propanoic acid, stearic acid, or oleic acid.

In an embodiment of the invention, the process for the production of a decarboxylated unsaturated carboxylic acid utilizes a catalyst or catalyst precursor containing both ruthenium and osmium compounds. In another embodiment of the invention, the catalyst or catalyst precursor is selected from the group consisting of ruthenium carbonyl or ruthenium chloride. In yet another embodiment of the invention, the catalyst or catalyst precursor is osmium carbonyl.

In another embodiment of the invention, the process for the production of a decarboxylated unsaturated carboxylic acid yields an olefin. In one embodiment of the invention, the disclosed decarboxylation process yields a mixture of internal and α-olefins. In yet another embodiment of the invention, the decarboxylation process yields a decarboxylated unsaturated carboxylic acid having a conjugated internal olefin.

In yet another embodiment of the invention, the process for the production of an decarboxylated unsaturated organic compound yields an olefin wherein the olefin is further subject to an oligomerization or a polymerization reaction. In one aspect of invention, the olefin product from decarboxylation process is further subject to a metathesis reaction.

Disclosed herein is a process for the isomerization and decarboxylation of an unsaturated organic compound, the process comprising contacting an unsaturated fatty acid in the presence of a catalyst or catalyst precursor containing ruthenium or osmium at a temperature at which the isomerization and decarboxylation occurs and recovering the isomerized and decarboxylated unsaturated organic compound.

In an embodiment of the invention, the process of the production of an isomerized and decarboxylated unsaturated organic compound comprises an additional step of contacting an additional acid to the unsaturated fatty acid in the presence of a catalyst or catalyst precursor. In another embodiment, the additional acid is a monocarboxylic acid. In yet another embodiment of the invention, the monocarboxylic acid is benzoic acid, cinnamic acid, propanoic acid, undecanoic acid, acetic acid, stearic acid, or oleic acid.

In an embodiment of the invention, the process for the production of isomerized and decarboxylated unsaturated organic compound utilizes a catalyst or catalyst precursor containing both ruthenium and osmium compounds. In another embodiment of the invention, the catalyst or catalyst precursor is selected from the group consisting of ruthenium carbonyl or ruthenium chloride. In yet another embodiment of the invention, the catalyst of catalyst precursor is osmium carbonyl.

In yet another embodiment of the invention, the process of the production of an isomerized and decarboxylated unsaturated organic compound yields an olefin. In one embodiment of the invention, the disclosed isomerization and decarboxylation process yields a mixture of internal and α-olefins. In yet another embodiment of the invention, the isomerization and decarboxylation process yields an unsaturated organic compound product having a conjugated internal olefin.

Also disclosed is a process for the production of an isomerized vegetable oil, the process comprising contacting a vegetable oil in the presence of a catalyst or catalyst precursor containing ruthenium or osmium at a temperature at which isomerization occurs and recovering the isomerized vegetable oil product, wherein the isomerization does not require the step of adding a carboxylic acid anhydride and the catalyst or catalyst precursor does not contain a phosphine ligand.

In an embodiment of the invention, the process for the production of an isomerized vegetable oil comprises an additional step of contacting vegetable oil in the presence of a catalyst or catalyst precursor. In another embodiment, the additional acid is a monocarboxylic acid. In yet another embodiment of the invention, the monocarboxylic acid is benzoic acid, cinnamic acid, propanoic acid, undecanoic acid, acetic acid, stearic acid, or oleic acid.

In an embodiment of the invention, the process for the production of an isomerized vegetable oil utilizes a catalyst or catalyst precursor containing both ruthenium and osmium compounds. In another embodiment of the invention, the catalyst or catalyst precursor is selected from the group consisting of ruthenium carbonyl or ruthenium chloride. In yet another embodiment of the invention, the catalyst or catalyst precursor compound is osmium carbonyl.

In another embodiment of the invention, the process for the production of an isomerized vegetable oil yields an olefin containing triglyceride. In one embodiment of the invention, the disclosed isomerized vegetable oil process yields an isomerized vegetable oil having a mixture of internal and α-olefins containing triglycerides. In yet another embodiment of the invention, the isomerization process yields an isomerized vegetable oil having a conjugated internal olefin.

In yet another embodiment of the invention, the process of the production of an isomerized vegetable oil utilizes soybean oil.

Also disclosed herein is a process for the isomerization and/or decarboxylation of the unsaturated organic compound wherein the process does not require the step of adding a carboxylic anhydride.

BRIEF DESCRIPTION OF THE DRAWINGS

The present invention may best be understood from the following detailed descriptions of the embodiments of the invention illustrated in the drawings, wherein.

DETAILED DESCRIPTION OF THE INVENTION

Definitions

Figure 1:
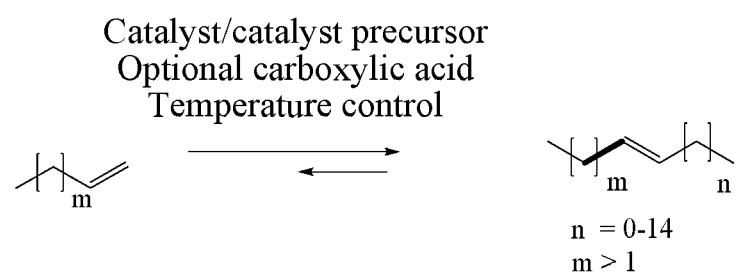
FIG. 1 is depiction of an exemplar reaction scheme for the isomerization of an unsaturated organic compound to an isomerized α-olefin, wherein n is between 0-14 for the purposes of the figure.
Figure 2:
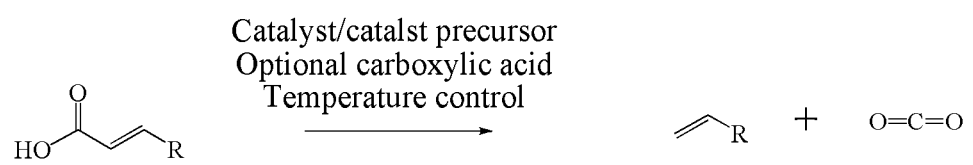
FIG. 2 is a depiction of an exemplar reaction scheme for the decarboxylation of an unsaturated carboxylic acid to produce an unsaturated organic compound.
Figure 3:
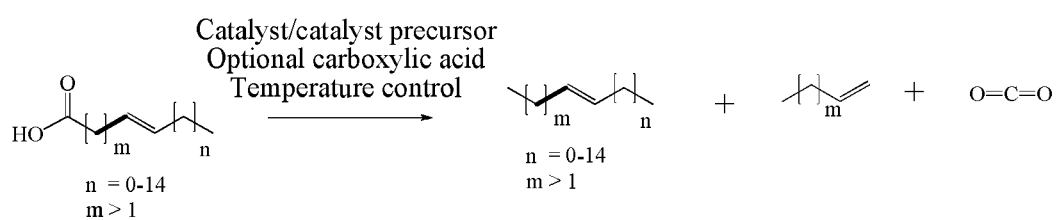
FIG. 3 is a depiction of an exemplar reaction scheme for the isomerization and decarboxylation of an unsaturated carboxylic acid to produce an unsaturated organic compound, wherein n is between 0-14 for the purposes of the figure.

As used in the specification and claims, the singular form "a", "an" and "the" include plural references unless the context clearly dictates otherwise.

Hereinafter, the present invention is explained in detail with reference to the following examples. The examples, however, should not in any sense be interpreted as limiting the scope of the present invention.

As used herein the term "alkene" or "olefin" refers to an unsaturated compound containing at least one carbon to carbon double bond. Examples of such include, but are not limited to any hydrocarbyl, hydrocarbyl aromatics, substitute or unsubstituted unsaturated fatty acids, unsaturated fatty esters, triglycerides diol diesters, mono-esters, derivatives of olefins having been reacted under olefin metathesis processes such as cross metathesis, ring-opening metathesis, ring-closing metathesis, acyclic diene metathesis or derivatives of olefins having been polymerized.

As used herein, the term "fatty acid" is to be understood in this specification as a long chain carboxylic acid having at least six carbon atoms. Fatty acids may be saturated or unsaturated compounds. These compounds may contain linear or branched alkyl groups, for example, linear or branched alkyl groups having between six and thirty carbon atoms. Preferably fatty acids comprise one or more ethylenically unsaturated carbons in the alkyl chain and include hexenoic acid, heptenoic acid, octenoic acid, nonenoic acid, decenoic acid, undecenoic acid, undecylenic acid, hendecenoic acid, dodecenoic acid, tridecenoic acid, tetradecenoic acid, myristitoleic acid, myristelaidic acid, pentadecenoic acid, hexadecenoid acid, palmitoleic acid, palmelaidic acid, heptadecenoic acid, octadecenoic acid, petroselinic acid, petroselaidic acid, oleic acid, elaidic acid, vaccenic acid, ricinoleic acid, ricinelaidic acid, nonadecenoic acid, eicosenoic acid, gondolic acid, heneicosenoic acid, docosenoic acid, erucic acid, brassidic acid, tricosenoic acid, tetracosenoic acid, nervonic acid, linoleic acid, lineladic acid, conjugated linoleic acid, linolenic acid, gamma linolenic acid, eicosadienoic acid, homogamma linolenic acid, eicosatrienoic acid, eicosatetranoic acid, arachidonic acid, eicosapentaenoic acid, EPA, docosadienoic acid, docosatrienoic acid, docosatetraenoic acid, docosapentaenoic acid, docosahexaenoic acid, and DHA.

As used herein, the term "fatty acid derivative" is to be understood in this specification as any compound comprising one or more groups derived from fatty acids. Examples of fatty acid derivatives are salts of fatty acids, for example salts, carboxylate salts, alkali salts, esters of fatty acids, preferably fatty acid ester group containing lipids, such as fatty acid ester group containing glycerolipids, fatty acid ester group containing glycerophospho-lipids, fatty acid ester group containing sphingolipids, fatty acid ester group containing sterol lipids, fatty acid ester group containing prenol lipids, fatty acid ester group containing saccharolipids and fatty acid ester group containing polyketides.

Preferred fatty acid derivatives are: octadecenoic acid, cinnamic acid, undecenoic acid, hexadecenoic acid, hydroxy octadecenoic acid.

As used herein, the term "recovering" as used in the context of recovering an isomerized product, decarboxylated product, or a tandem isomerized and decarboxylated product includes: crystallization, distillation, reactive distillation, extrusion, decanting, extraction, microfiltration, nanofiltration, or such techniques that are known to those skilled in the art.

The disclosed process utilizes a metal-based homogeneous or heterogeneous catalyst. As used herein, the term "catalyst precursor" a metal compound where it can be activated in order to be used as a catalyst, particularly as an olefin isomerization or decarboxylation catalyst. Generally, such catalysts are activated by means of heating as described herein below. In one embodiment, the catalyst precursor form as a catalyst in situ with the process described herein.

The catalyst or catalyst precursors used in the process contain ruthenium or osmium compounds. It is contemplated that the catalyst or catalyst precursor contained both ruthenium and osmium would be utilized for the disclosed isomerization, decarboxylation, and duel isomerization decarboxylation processes.

The selection of a suitable ruthenium or osmium compound to provide the catalytic activity for isomerization or decarboxylation or tandem isomerization and decarboxylation reaction is not narrowly critical. Essentially any ruthenium or osmium compound can be effectively utilized to carry out the disclosed isomerization and/or decarboxylation reactions. However, the invention is believed to involve novel ruthenium-based catalysts and osmium-based catalysts that promote the isomerization of an olefin and decarboxylation of an unsaturated carboxylic acid as the said metal forms a complex with the reaction mixture. It is believed the primary requirement for the generation of such catalysts and the requisite catalytic activity are ruthenium precursors to the catalyst which can be converted to $[Ru(CO)_2RCO_2]_n$ or similar compounds even if the precursor during the reaction fails to be converted to such structures. $[Ru(CO)_2RCO_2]_n$ or similar compounds may or may not be the isomerization or decarboxylation catalyst of the invention but it has been noted that the use of such compounds assures the effective catalytic reaction and the results herein characterized. The process of this invention may be practiced with a vast array of ruthenium and/or osmium compounds. Even instances where the ruthenium or osmium compound is too stable for catalyzing the reaction, catalysts can be effected by including a compound which does not adversely affect the isomerization or decarboxylation reaction and stimulates the ruthenium or osmium compound to be converted to a species having catalytic activity. For example, ruthenium chloride is a sluggish catalyst but is made quite active by the addition of an alkali such as an alkali metal salt of a carboxylic acid, viz. sodium oleate. It is not presumed that simple ruthenium salt compounds are the catalyst or that many of the ruthenium compounds herein used to effect the catalytic reaction are the catalyst. The exact ruthenium or osmium containing compound or compounds that constitute the catalyst of this invention is not appreciated but what is appreciated is that many ruthenium or osmium compounds can be used to in situ generate the catalyst. The diversity of the selection of ruthenium compounds or osmium compounds suitably employable as precursors to catalysts in the process of the invention is quite broad. It is further contemplated that the catalyst or catalyst precursor is recovered for subsequent isomerization, decarboxylation, or tandem the isomerization and decarboxylation reactions. It is preferable that the catalyst or precursor be maintained in an anaerobic atmosphere to prevent oxidation of the catalyst of precursor.

Compounds containing such ruthenium moieties include ruthenium carboxylates and ruthenium carbonyls such as $[Ru(CO)_2Acetate]_n$, $Ru_3(CO)_{12}$, $[Ru(CO)_2(EtCO_2)]_n$, or $[Ru_xC_yO_zH_w]_n$ where X is an integer greater or equal to 1, and W, Y, and Z are whole numbers or zero. Other catalyst or catalyst precursor containing ruthenium compounds include ruthenium carbenes and ruthenium chloride. The preferred catalyst and catalyst precursors are $Ru_3(CO)_{12}$, $[Ru(CO)_2(EtCO_2)]_n$, $Ru_3O(EtCO_2)_m(H_2O)_n$. Catalyst or catalyst precursors containing osmium compounds having a ligand of chloride, carbene, or carboxylate. As used in determining the precursor formula, n and m are integers greater than zero.

It is contemplated that the catalyst compounds may range from supported material such as ruthenium on carbon, alumina, and the like. Other contemplated support material includes silica, alumina, zeolites, zirconia, titania, titania, carbon, polyacrylic acid copolymers, acrylic acid containing polymers, and methacrylic acid containing polymers.

The preferred catalysts are formed from ruthenium carbonyl carboxylates, or precursors which can convert into these species. Based on the recognition that ruthenium carbonyl reacts with carboxylic acids to produce soluble orange-yellow complexes possessing the empirical formula $[Ru(CO)_2RCO_2]_n$ and the fact these complexes appear sufficiently labile to accommodate coordination of alkenyl double bonds and ruthenium-bound carboxylates, it is believed that such structures are involved in the catalysis of the isomerization and decarboxylation process. For example, it is known that in the presence of carbon monoxide, $[Ru(CO)_2RCO_2]_n$ is readily converted to $Ru_2(CO)_6(RCO_2)_2$ dimer. Analogously, substitution with other ligands such as phosphines gives $Ru_2(CO)_4(L)_2(RCO_2)_2$ complexes, where L is a donor ligand. Similar affinity for coordination is thus proposed for alkenyl derivatives.

It is contemplated that compounds containing ruthenium includes tetrahydridotetraruthenium dodecacarbonyl, $H_4Ru_4(CO)_{12}$, which can also be used to form the catalyst.

Catalyst precursors such as ruthenium(III) chloride, ruthenium(III) iodide, tris(2,2-bipyridyl)ruthenium(II) chloride hexahydrate, dichlorotricarbonylruthenium (II) dimer, $[RuCl_2(CO)_3]_2$, ruthenium (III) acetoacetonate, ruthenium (IV) oxide, ruthenium on carbon, ruthenium on alumina, and ruthenocene are contemplated to exhibit some level of catalyst activity.

The olefin isomerization process of this invention using $Ru(CO)_X$ compounds may be conducted at temperatures in the range of about 50° C. to about 350° C., but preferably in the range of about 150° C. to about 300° C. The isomerization process is typically conducted in an inert atmosphere e.g., under nitrogen, argon or in the presence of other gases such as hydrogen, carbon dioxide, carbon monoxide, and ethylene. The process is typically conducted at atmospheric pressure (about 1.0 bars) but may be conducted at any manageable pressure typically in the range of about 0.1 to about 25 bars, and preferably in the range of about 0.5 bars to about 5.0 bars. The reaction may be carried out at pressures which are subatmospheric, atmospheric or superatmospheric. In some situations, reaction can also be conducted under vacuum such as in a distillation apparatus.

The olefin decarboxylation process of this invention using the empirical formula $Ru(CO)_X$, compounds may be conducted at temperatures in the range of about 90° C. to about 350° C., but preferably in the range of about 150° C. to about 300° C. The decarboxylation process is typically conducted in an inert atmosphere e.g., under nitrogen, argon or in the presence of other gases such as hydrogen, carbon dioxide, carbon monoxide, and ethylene. The process is typically conducted at atmospheric pressure (about 1.0 bars) but may be conducted at any manageable pressure typically in the range of about 0.1 to about 25 bars, and preferably in the range of about 0.5 bars to about 5.0 bars. The reaction may be carried out at pressures which are subatmospheric, atmospheric or superatmospheric. In some situations, reaction can also be conducted under vacuum such as in a distillation apparatus.

The dual tandem isomerization and decarboxylation process of this invention using $Ru(CO)_X$ compounds may be conducted at temperatures in the range of about 90° C. to about 350° C., but preferably in the range of about 150° C. to about 300° C. The isomerization and decarboxylation process is typically conducted in an inert atmosphere e.g., under nitrogen or in the presence of other gases such as hydrogen, carbon dioxide, carbon monoxide, and ethylene. The process is typically conducted at atmospheric pressure (about 1.0 bars) but may be conducted at any manageable pressure typically in the range of about 0.1 to about 25 bars, and preferably in the range of about 0.5 bars to about 5.0 bars. The reaction may be carried out at pressures which are subatmospheric, atmospheric or superatmospheric. In some situations, reaction can also be conducted under vacuum such as in a distillation apparatus.

It has been found that $[Ru(CO)_2RCO_2]_n$, can be generated in several ways. For example, the trinuclear complex, $[Ru_3O(C_2H_5COO)_6(H_2O)_3](C_2H_5COO)]$ gives an efficient isomerization or decarboxylation catalyst. Visual color change observations suggest $Ru_3O(C_2H_5COO)_6(H_2O)_3](C_2H_5COO)$ can convert to $[Ru(CO)_2RCO_2]_n$ under isomerization or decarboxylation reaction conditions under an argon atmosphere. It is contemplated that generation of the ruthenium complex would be generated in inert atmospheres such as argon through a redox reaction. Visual evidence of this reaction observed a green air oxidized complex turning yellow amber following isomerization or decarboxylation catalysis.

The amount of the ruthenium catalyst useful for effecting the isomerization and/or decarboxylation reaction is not narrowly critical. The typical amount is a catalytically effective amount, that is, an amount which is sufficient to effect the desired isomerization and/or decarboxylation. For example, it has been established that ruthenium catalyst concentrations ranging roughly from about 50,000 parts to about 0.05 part per million (ppm) ruthenium based on the weight of the liquid phase reaction medium can be used to effect the reaction. It is believed that larger and smaller amounts of the catalyst may be used to effect the reaction. The most preferred range is from about 5,000 ppm to about 0.5 ppm ruthenium, same basis.

As used herein the term "apparently complete steady state" refers to an observable amount of isomerized and/or decarboxylated product via gas chromatography, wherein additional time or the addition of catalyst or catalyst precursor would not result in a change in product distribution.

The following examples set forth methods in accordance with the invention. It is to be understood, however, that these examples are provided by way of illustration and nothing therein should be taken as a limitation upon the overall scope of the invention.

Example 1: Isomerization of Oleic Acid with $[Ru(CO)_2Acetate]_n$ 2.9 mg of $[Ru(CO)_2Acetate]_n$ and 5.10 grams of oleic acid (90% United States Biochemical Corporation) was charged to a round-bottomed flask equipped with a stir bar, thermometer, and nitrogen inlet. The calculated ruthenium concentration was 270 parts per million. The purged flask was heated in a sand-bath crucible at 263° C.-277° C. for 1 hour. Upon cooling the flask contents started to cloud and solidify at 31° C.-32° C.

Example 2: Isomerization and Decarboxylation of Oleic Acid

A melted small sample of the flask contents from Example 1 was taken from the original reaction mixture by pipette and charged to a small vial. The vial was flushed with nitrogen and crimped. The sample was place on a hot plate. The sample appears to start vaporizing (septum puffed up). Within about one minute the vial was removed from the heat and allowed to cool. The vial, cooled to room temperature, was a yellow flowing liquid (liquid Analyzed by IR) that eventually solidified. Through this short heating, the melting point was decreased compared to the prior composition. The vial was again heated on the hot plate while being continuously purged with nitrogen vial a Pasteur Pipette (packed through the septum) for a few minutes. The release of a gaseous substance was observed using a bubbler. When the vial was cooled to room temperature, it resulted in an intensely yellow colored liquid substance that solidified to a solid overnight. The vial contents was treated with an additional ruthenium in the form of $Ru_3(CO)_{12}$ (a 1 mg particle) under nitrogen. The vial, equipped with a Pasteur pipette for nitrogen delivery was placed on the hot plate next to a very small beaker filled with sand and containing the bulb of a high temperature thermometer at 260° C. The vial occasionally bubbled as the temperature reached 260° C. The heating lasted approximately 0.7 hr. The cooled vial contained a viscous liquid. IR analysis indicated that the oleic acid was noticeably being isomerized and decarboxylated. The carbonyl frequency at $1710$ $cm^{-1}$ was decreasing while a weaker olefin band at $1465$ $cm^{-1}$ was increasing relative to previous IR samples. A small amount of the reaction product was dissolved in petroleum ether. GC analysis verified isomeric $C_{17}$ olefins products.

Example 3: Decarboxylation of Cinnamic Acid Using $Ru_3(CO)_{12}$

In a vial, 0.10 grams of trans-cinnamic acid was added to 1.1 mg of $Ru_3(CO)_{12}$. As a comparative example, a separate vial with 0.10 grams of trans-cinnamic acid with no ruthenium was prepared.

The vials were flushed with nitrogen, capped with a septum, crimped, and fitted with a Pasteur Pipette (for the introduction of nitrogen atmosphere and the release of gaseous products). The Pipette bulb was pierced with a nitrogen inlet needle to maintain a nitrogen atmosphere. The vials were placed together on a hot plate next to a very small beaker filled with sand and containing the bulb of a high temperature thermometer.

As the hot plate warmed, the $Ru_3(CO)_{12}$-containing vial melted at a sand bath temperature of 99° C. forming an orange solution initially. As the sand temperature reached 135° C., (hot plate setting 250° C.) the $Ru_3(CO)_{12}$-containing vial started to bubble with the appearance of a "cloudy gas" evolving into the Pipette and then the refluxing of a liquid which condensed in the Pasteur Pipette and returned to the vial. Refluxing on the sides of the vial were also observable. The vial initially containing ruthenium was heated 20-30 minutes and the sand temperature increased to 154° C. At a sand temperature of 85° C., the vial with $Ru_3(CO)_{12}$ solidified to a clear yellow-orange solid with a styrene odor. The vial lost a mass of ~0.02 grams, indication the loss of $CO_2$ via decarboxylation.

In the vial where no ruthenium was added, the trans-cinnamic acid melted at ~105° C. forming a yellow-green liquid. The vial was heated 20-30 minutes and the sand temperature increased to 154° C. Continual application of heat did not appear to change the yellow-green liquid. The hot plate was turned off and the vial was allowed to cool. At a sand temperature of 95° C. the vial containing no ruthenium solidified.

The contents of each vial was dissolve in about 0.2 mL of acetone and analyzed by gas chromatography. In the vial containing $Ru_3(CO)_{12}$ showed a relative peak area ratio of 0.708 styrene and 0.292 trans-cinnamic acid. In the vial without ruthenium added, a relative peak area ratio of 0.001 styrene:0.999 of trans-cinnamic acid.

Example 4: Isomerization of 10-Undecylenic Acid with $Ru_3(CO)_{12}$ at 180° C.

10-Undecylenic acid (0.124 grams) and $Ru_3(CO)_{12}$ (0.7 mg) were added to a small vial. The vial was flushed with nitrogen, capped, crimped, fitted with a wire hook, and suspended in an 180° C. oil bath. The reaction mixture was heated several days at a temperature range of 180° C. to 185° C. The final solution remained amber orange in color. Occasionally, the vial was removed briefly from the bath for the removal of a GC sample (at times of 5 h, 20 h, 40 h, 116.5 h, and 186 h). Samples were diluted with acetone prior to GC analysis. GC analysis showed principally the isomerized undecylenic acid product.

Example 5: Ruthenium-Catalyzed Decarboxylation of Carboxylic Acid Using $Ru_3(CO)_{12}$ In separate vials the following carboxylic acids were added to vials containing the specified masses of $Ru_3(CO)_{12}$ as indicated in Table 1 below. Each vial was flushed with nitrogen, capped and crimped to form an air-tight seal. A copper wire was wrapped around the vial to create a suspension hook and a label was attached. Each assembly was weighed prior to heating.

TABLE 1

| Carboxylic Acid | Ruthenium Complex |
| --- | --- |
| 0.0981 grams of trans-cinnamic acid (MP 133-134° C.) | 1.8 mg of $Ru_3(CO)_{12}$ |
| 0.1094 grams of maleic acid (MP 140-142° C.) | 1.4 mg of $Ru_3(CO)_{12}$ |
| 0.1006 grams of benzoic acid (122-123° C.) | 1.8 mg of $Ru_3(CO)_{12}$ |

Example 5A: Decarboxylation of Trans-Cinnamic Acid

The vial was fitted with a nitrogen inlet needle attached to a bubbler and suspended in an oil bath at 127° C. The bath was gradually warmed and the mixture melted forming an orange solution. The nitrogen bubble rate was calibrated in an effort to detect the evolution of product gases from the vial such as carbon dioxide. The temperature of the oil bath was increased to 215° C. (gaseous bubbles, and some refluxing of a more volatile liquid could be seen in the vial). After approximately 30 minutes at 215° C. the vial was removed from the oil bath, the solution was bright red in color while still hot. The mass loss from the vial was 0.0291 grams.

Example 5B: Decarboxylation of Maleic Acid

The vial was fitted with a nitrogen inlet needle attached to a bubbler and suspended in an oil bath at 163° C. The mixture melted but an insoluble residue was apparent (possibly isomerization to fumaric acid). The nitrogen bubble rate was calibrated in an effort to detect the evolution of product gases from the vial such as carbon dioxide. The temperature of the oil bath was increased to 195° C. (gaseous bubbles, and some refluxing of a more volatile liquid could be seen in the vial). After approximately 15 minutes at 190-196° C. the vial was removed from the oil bath, the solution was bright red in color while still hot. The mass loss from the vial was 0.0310 grams.

Example 5C: Decarboxylation of Benzoic Acid

The vial was fitted with a nitrogen inlet needle attached to a bubbler and suspended in an oil bath at 165° C. The bath was gradually warmed and the mixture immediately melted forming an orange solution. The nitrogen bubble rate was calibrated in an effort to detect the evolution of product gases from the vial such as carbon dioxide. The temperature of the oil bath was increased to 220° C. After approximately 15 minutes at 215° C.-220° C. the vial was removed from the oil bath, the solution was bright red in color while still hot, but solidified to a yellow solid. The mass loss was not detectable from the vial during the reaction.

Example 6: Decarboxylation of 10-Undecylenic Acid

The vial was charged with $Ru_3(CO)_{12}$ (2.1 mg) and 10-Undecylenic Acid (0.1636 g), flushed with nitrogen, capped, crimped, and fitted with a nitrogen inlet needle that was attached to a bubbler. The sample was warmed on a hot plate warmed to 280° C.-300° C. for 1 hour. As the reaction progressed, gas evolution and the condensation (refluxing) of a volatile liquid above the burnt orange catalyst solution was observed. When the vial was removed from the heat source, immediately turned a lighter amber color. The weight loss during the reaction was 0.0263 grams or 16.08%. For total conversion of 10-undecylenic acid (Mw 184.28) to decene isomer(s) (Mw 140.27) the expected mass loss would be 23.9%. GC Analysis confirmed that decene isomers and undecylenic acid isomers were formed.

Example 7: Decarboxylation of Oleic Acid

The vial was charged with $Ru_3(CO)_{12}$ (3.3 mg) and oleic acid (0.2109 g), flushed with nitrogen, capped, crimped, and fitted with a nitrogen inlet needle that was attached to a bubbler. The sample was heated on a hot plate warmed to 280° C.-300° C. for 1 hour. The weight loss during the reaction was 0.0351 grams or 16.64%.

Example 8: Decarboxylation of Linoleic Acid

The vial was charged with $Ru_3(CO)_{12}$ (2.3 mg) and linoleic acid (0.1733 g), flushed with nitrogen, capped, crimped, and fitted with a nitrogen inlet needle that was attached to a bubbler. The sample was heated on a hot plate warmed to 280° C.-300° C. for 1 hour. The weight loss during the reaction was 0.0075 grams.

Example 9: Decarboxylation of Stearic Acid

The vial was charged with $Ru_3(CO)_{12}$ (1.9 mg) and stearic acid (0.2277 g), flushed with nitrogen, capped, crimped, and fitted with a nitrogen inlet needle that was attached to a bubbler. The sample was heated on a hot plate warmed to 280° C.-300° C. for 1 hour. The weight loss during the reaction was 0.0027 grams.

Figure 4:
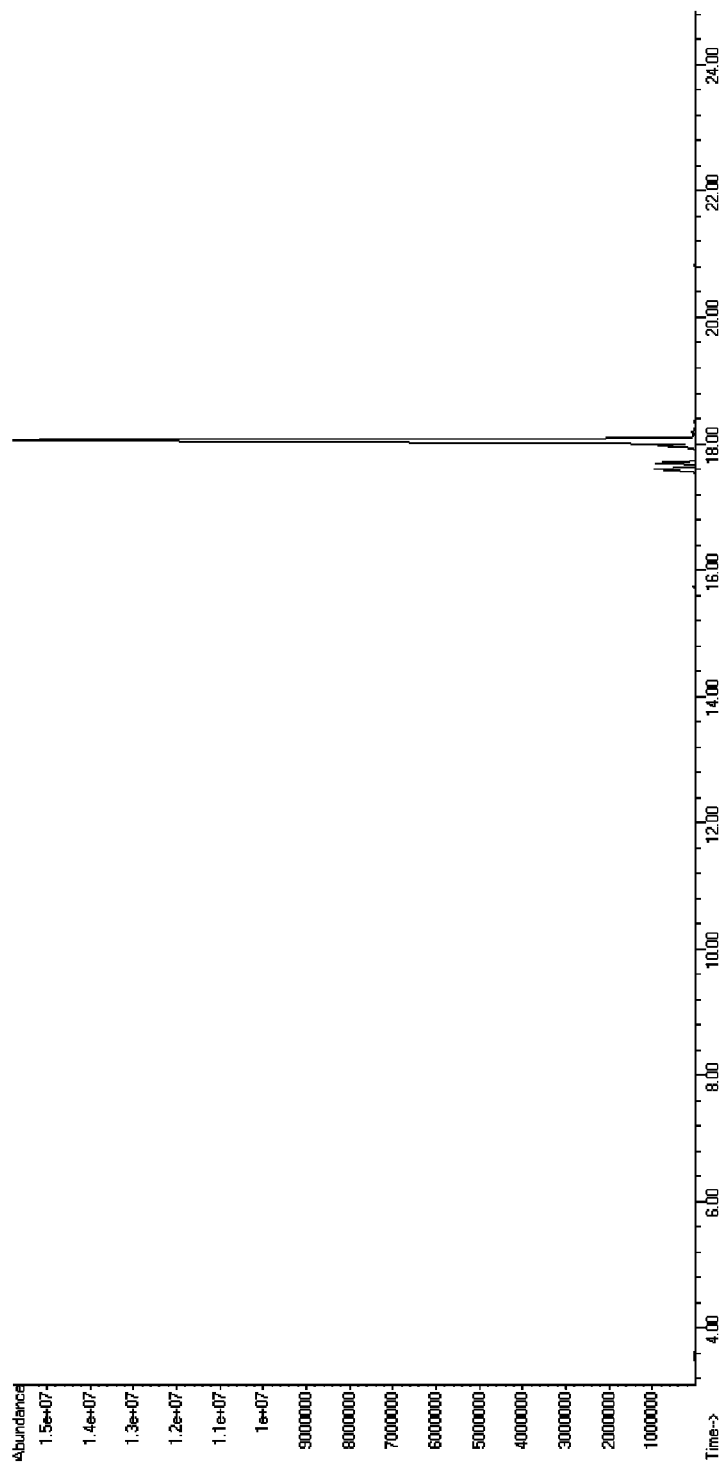
FIG. 4 is a chromatogram of a gas chromatography-mass spectrometry of 1-octadecene as a function of elution time (minutes).
Figure 5:
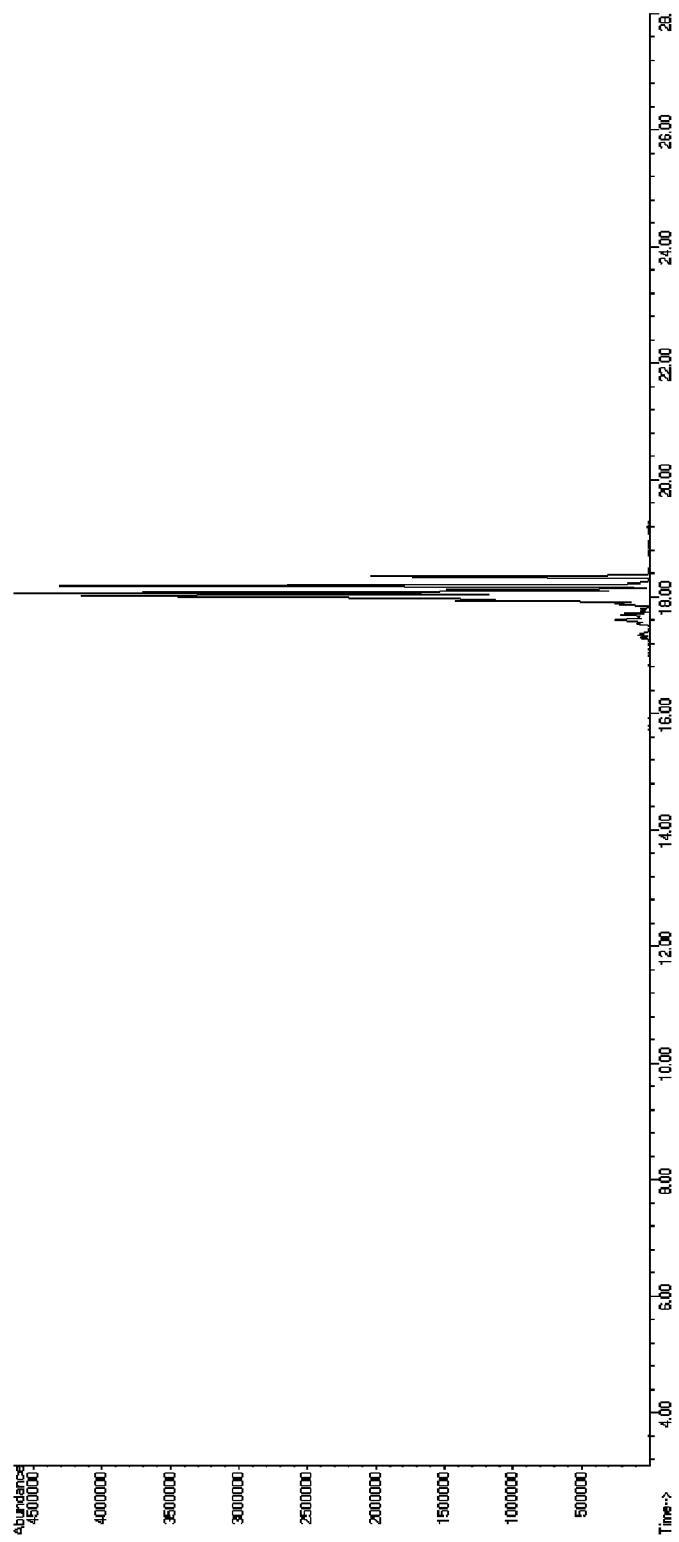
FIG. 5 is a chromatogram of a gas chromatography-mass spectrometry of 1-octadecene after the isomerization process described in Example 10 as a function of elution time (minutes).

Example 10: The Isomerization of 1-Octadecene with the Reaction Prepared in an Inert-Atmosphere Dry-Box Inside an inert atmosphere dry-box, 4.9834 g of 1-octadecene, 0.0519 g octadecanoic acid, and 0.003 g $Ru_3(CO)_{12}$ were weighed into a Pyrex 16×150 mm culture tube which was sealed with and a septa capped lid. The tube was removed from the dry-box and connected to argon flow from a Schlenk line through a 22 gauge needle. The tube was heated in an aluminum block which was set to achieve a temperature of 250° C., and reacted for 4 hours. The actual reaction temperature varied with substrate and production as some of the reactants and products reflux under these conditions which can cool the reaction tube. The reaction turned pale yellow, and was analyzed by GC-MS. The GC-MS utilized was an Agilent 7890A gas chromatograph equipped with a 7683B series injector and a 5975 C quadrapole mass detector. A J&W 123-3832, 30 m×320 um×0.25 um, column was used. Injections were 1 uL and a 50:1 split ratio was used. Temperatures were: MS Source 230° C., MS Quad 150° C., GC inlet 340° C., GC Auxiliary line 340° C. The oven temperature program was: 40° C. hold 3 min, ramp 10° C./min to 190° C. hold 5 min, ramp 25° C./min to 340° C. Samples of ~10 uL were dissolved in 1 mL of acetone for analysis, and response factors were calculated by injection of known compounds using the same method. The starting material, FIG. 4 and the product, FIG. 5, depict the effect of the isomerization.

Example 11: Isomerization of 1-Octadecene with $[Ru(CO)_2(EtCO_2)]_n$

Figure 6:
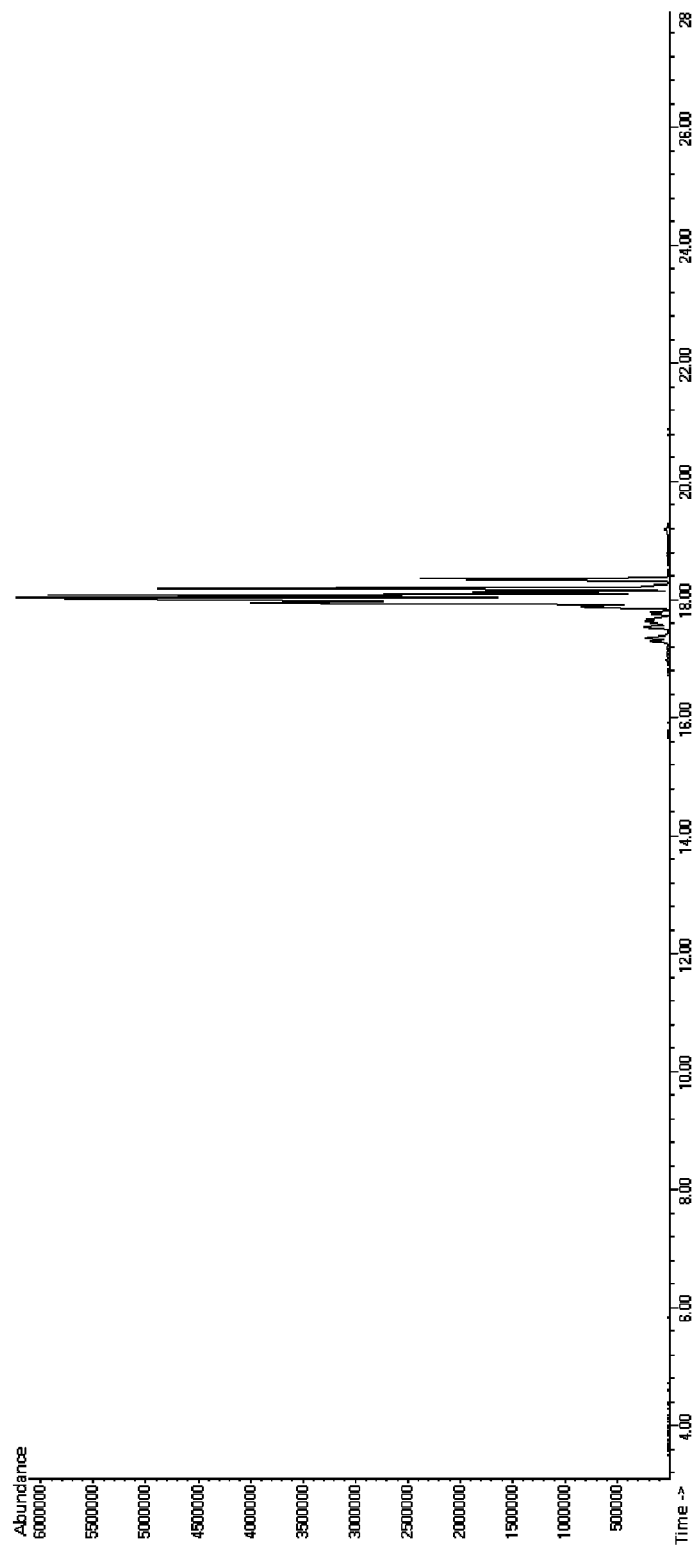
FIG. 6 is a chromatogram of a gas chromatography-mass spectrometry of 1-octadecene after the isomerization process described in Example 11 as a function of elution time (minutes).

This reaction was performed identically to Example 10, but in this case, 2.0017 g of 1-octadecene and 0.002 g $[Ru(CO)_2(EtCO_2)]_n$ were used. This reaction solution turned orange, then brown. The chromatogram, FIG. 6, has a similar distribution to that in Example 10.

Example 11a Control Experiment

Isomerization with No Ruthenium Catalyst Precursor

Figure 7:
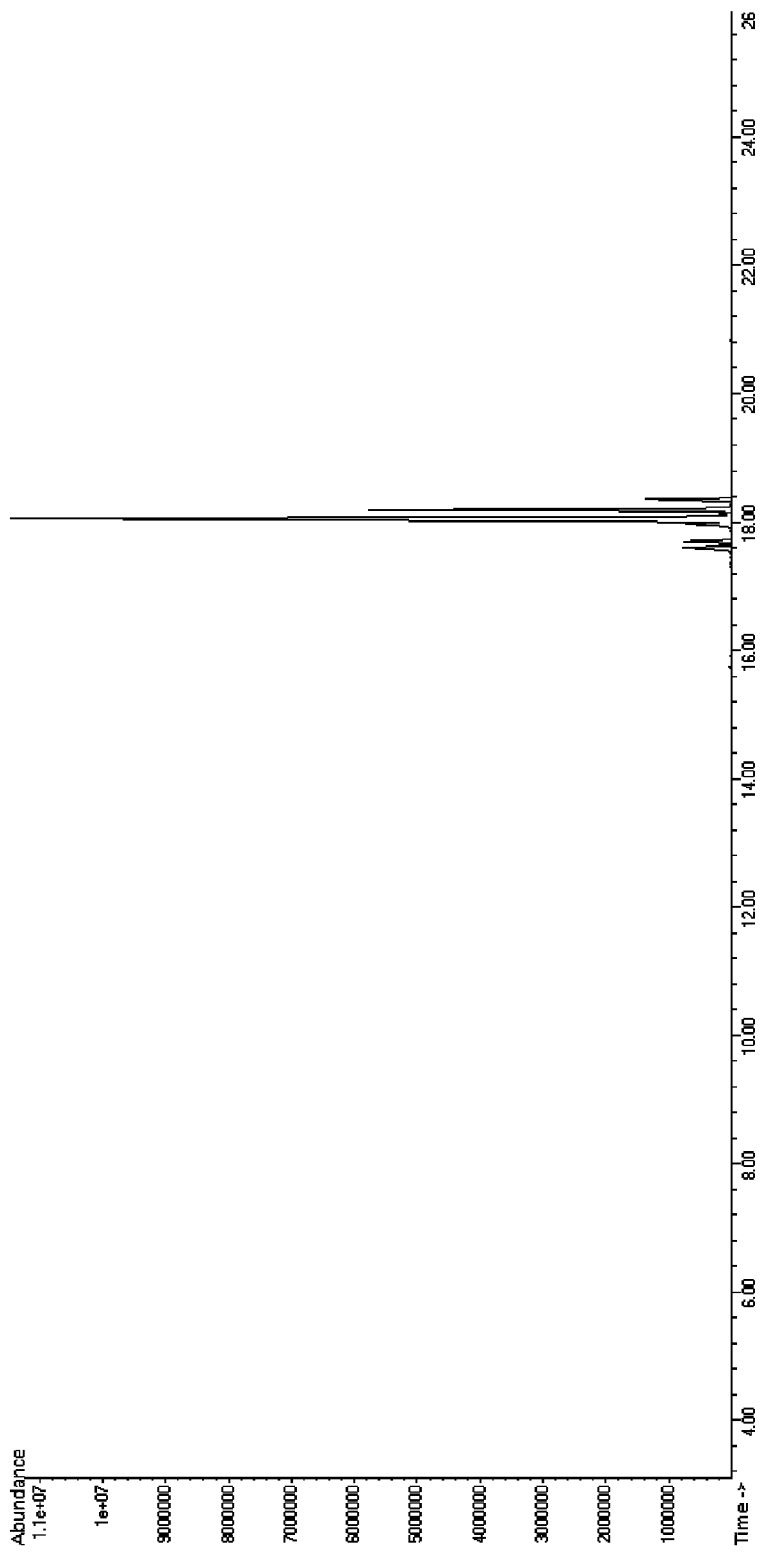
FIG. 7 is a chromatogram of a gas chromatography-mass spectrometry of 1-octadecene after the isomerization process described in Example 11A as a function of elution time (minutes).

This was reaction was performed identically to Example 10, but in this case, 5.0519 g of 1-octadecene, but no stearic acid or $Ru_3(CO)_{12}$ were used. The chromatogram, FIG. 7, is much less isomerized than in Example 10.

Example 12: Isomerization without the Presence of Octadecanoic Acid

Figure 8:
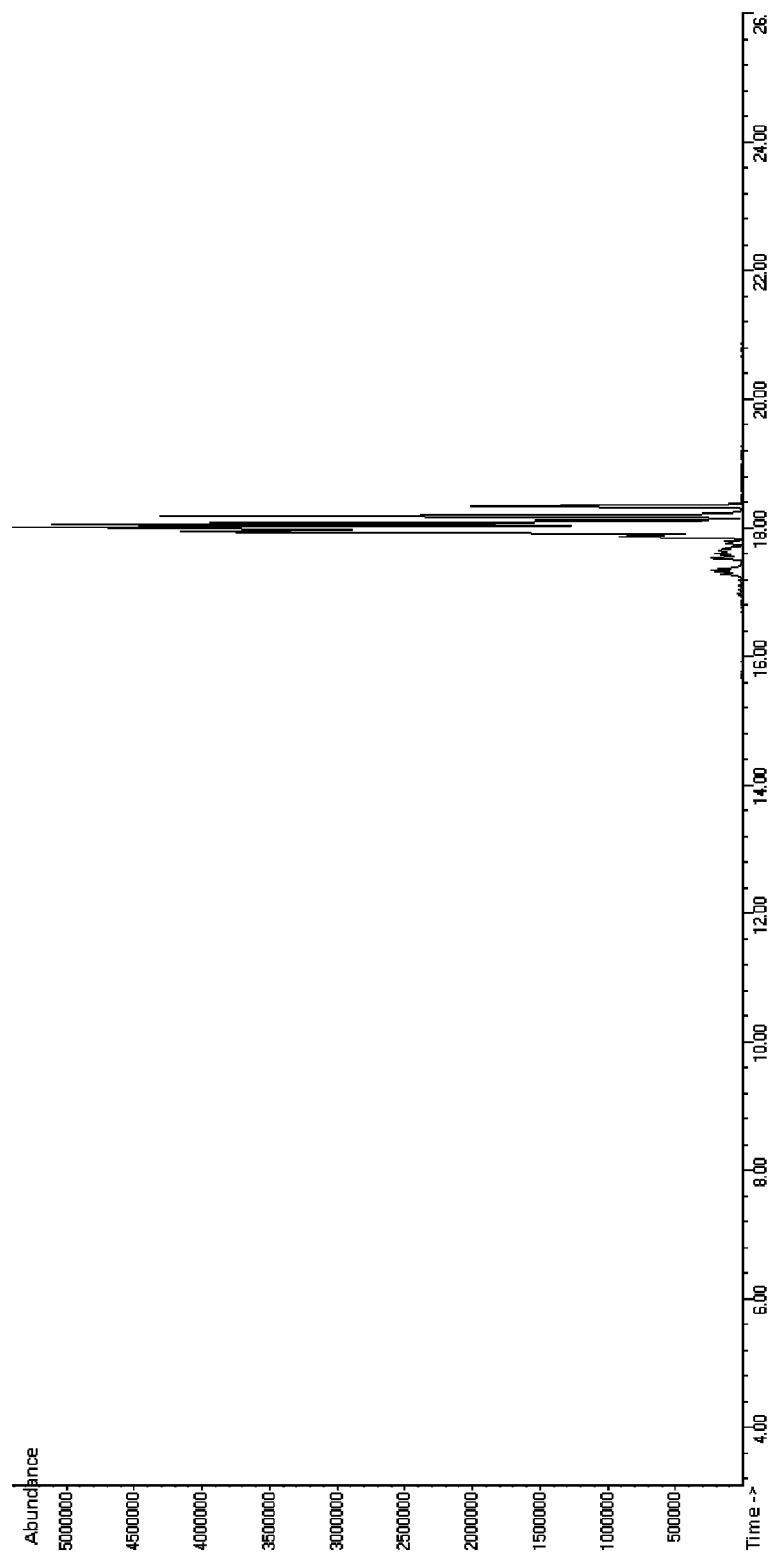
FIG. 8 is a chromatogram of a gas chromatography-mass spectrometry of 1-octadecene after the isomerization process described in Example 12 as a function of elution time (minutes).

This was reaction was performed identically to Example 10, but in this case, 5.0519 g of 1-octadecene and 0.043 g $Ru_3(CO)_{12}$. No octadecanoic acid was used and the reaction temperature was only 150° C. The chromatogram, FIG. 8, has a similar distribution to that in Example 10.

Figure 9:
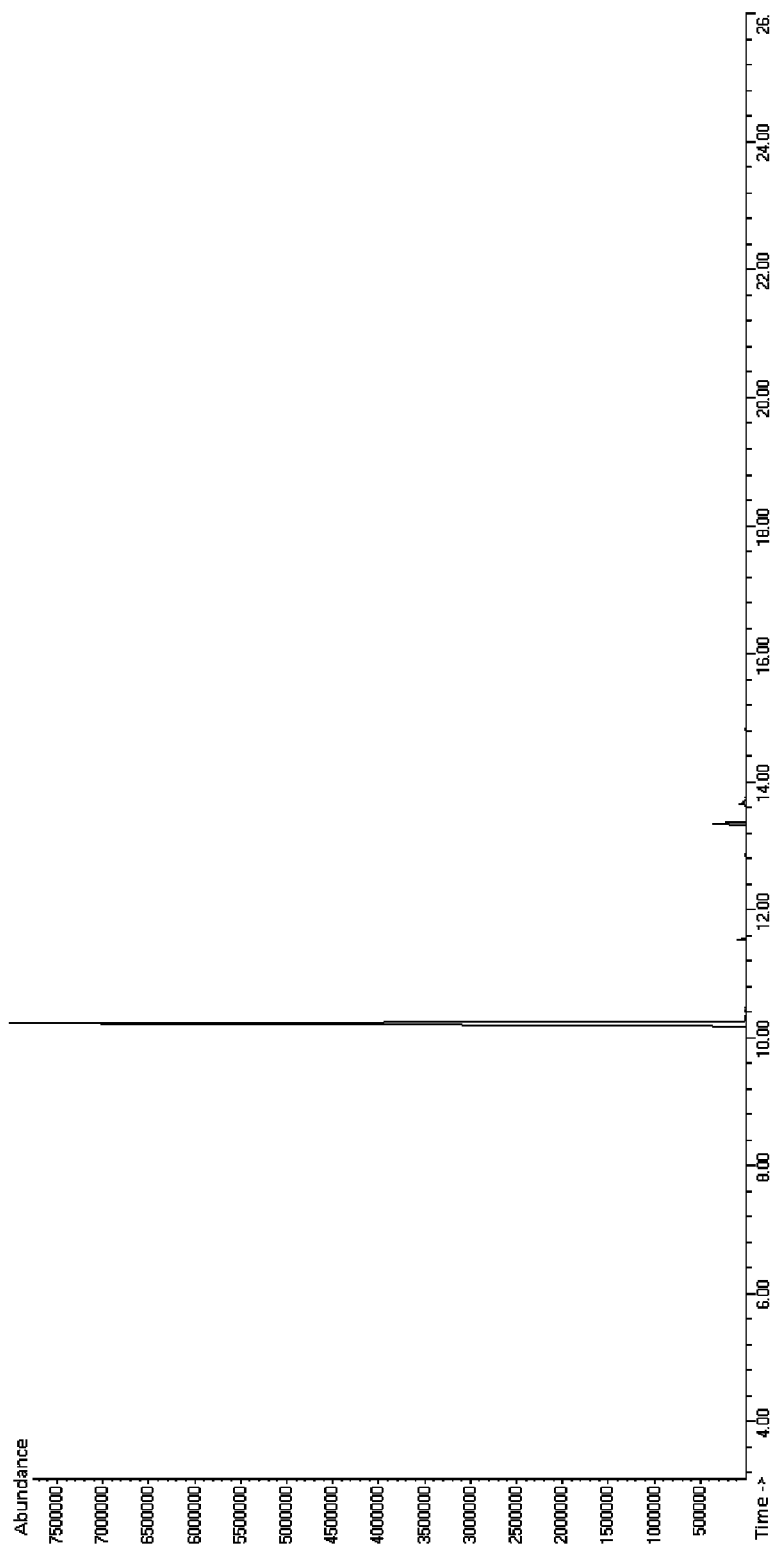
FIG. 9 is a chromatogram of a gas chromatography-mass spectrometry of 2-methyl-1-undecene as a function of elution time (minutes), before the isomerization process described in Example 13.
Figure 10:
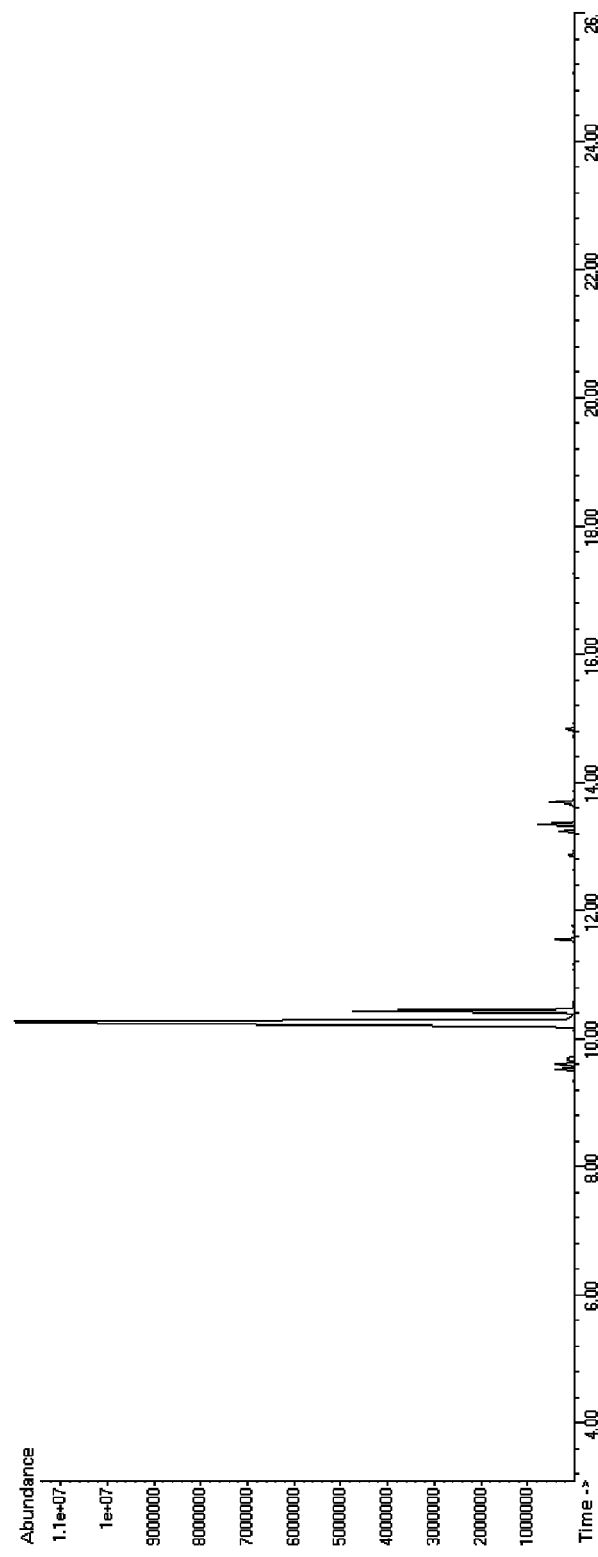
FIG. 10 is a chromatogram of a gas chromatography-mass spectrometry of 2-methyl-1-undecene after the isomerization process described in Example 13 as a function of elution time (minutes).

Example 13: Isomerization of 2-Methyl-1-Undecene with $Ru_3(CO)_{12}$/Octadecanoic Acid A stock solution of catalyst precursor was made, inside an inert atmosphere dry-box, by melting 5.0382 g of octadecanoic acid and adding 0.0010 g $Ru_3(CO)_{12}$. This solution was heated to 100° C. for 45 minutes, upon which time the solution turned orange. Upon cooling a yellow solution could be observed, which solidified at room temperature. Inside of the dry-box, 0.0674 g of catalyst precursor stock solution was added to 0.9387 g of 2-methyl-1-undecenoene in a speta capped pyrex culture tube. This tube was taken out of the dry-box, connected by needle to an argon flow via Schlenk line, and heated to 200° C. for 4 hours. This sample was analyzed by GC-MS, as done in Example 10. Comparison of the chromatograms, FIGS. 9 and 10, show 14% conversion to the 2-methyl-2-undecene.

Figure 11:
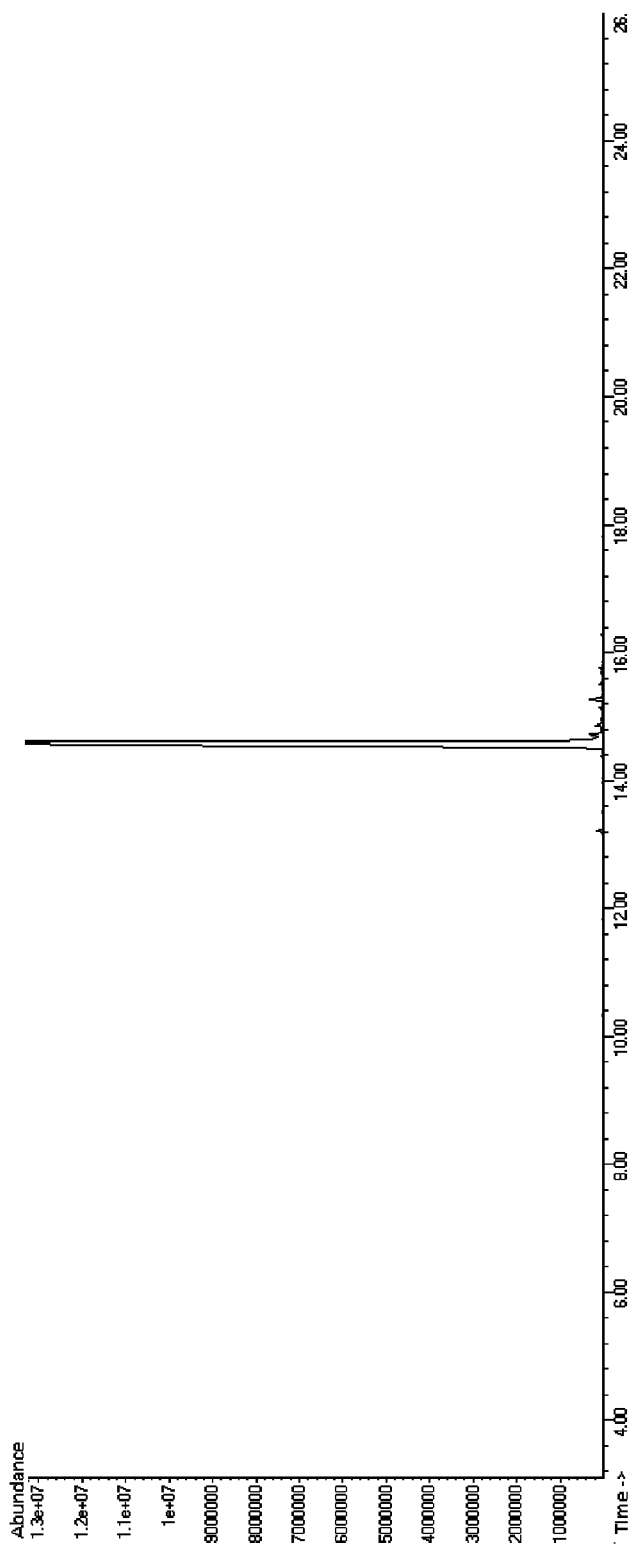
FIG. 11 is a chromatogram of a gas chromatography-mass spectrometry of methyl-10-undecenoate as a function of elution time (minutes), before the isomerization process described in Example 14.
Figure 12:
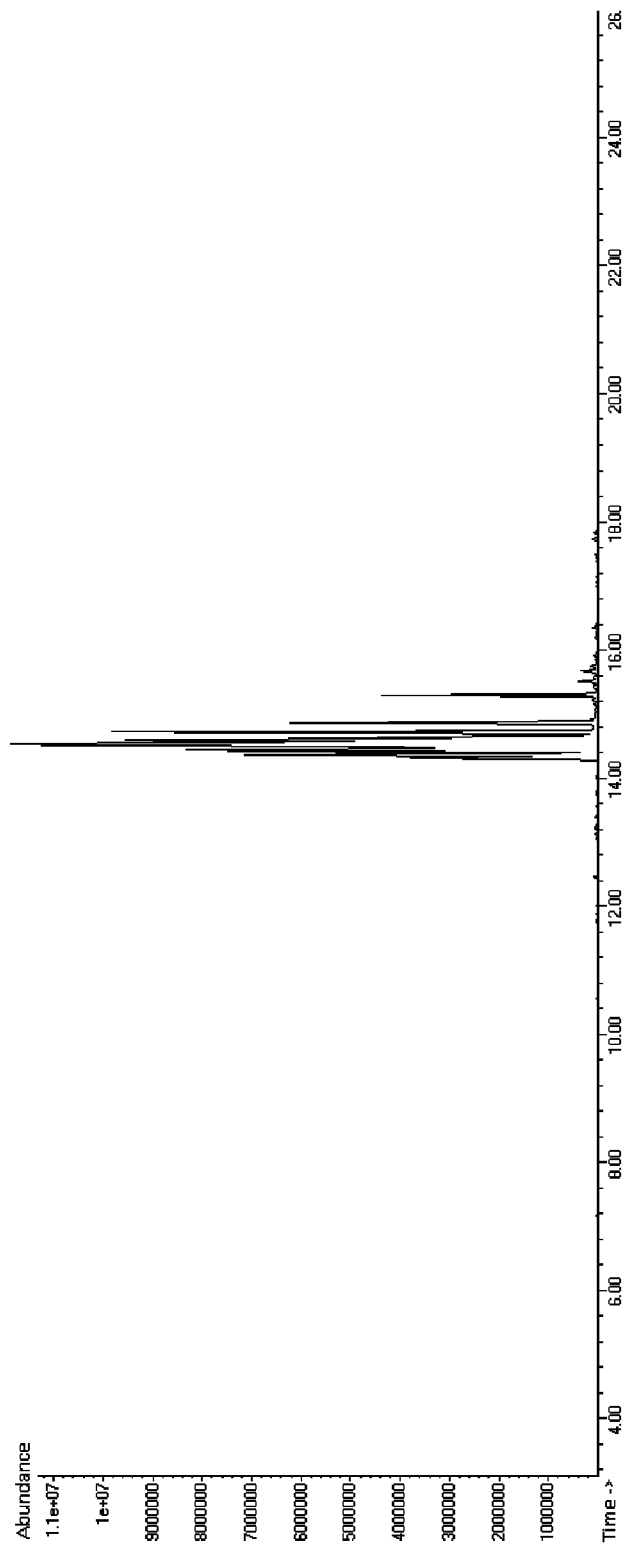
FIG. 12 is a chromatogram of a gas chromatography-mass spectrometry of methyl-10-undecenoate, after the isomerization process described in Example 14 as a function of elution time (minutes).

Example 14: Isomerization of Methyl 10-Undecenoate with $[Ru(CO)_2(EtCO_2)]_n$ in 4 Hours This reaction was ran by the same method as Example 10, using 0.0021 g of $[Ru(CO)_2(EtCO_2)]_n$ and 2.0521 g of methyl 10-undecenoate. This reaction was run at 250° C. for 4 hours. Comparison of the chromatograms, FIGS. 11 and 12, show apparently complete steady state isomerization.

Example 15: Isomerization of Methyl 10-Undecenoate with $[Ru(CO)_2(EtCO_2)]_n$ in 4 Hours at 150° C.

Figure 13:
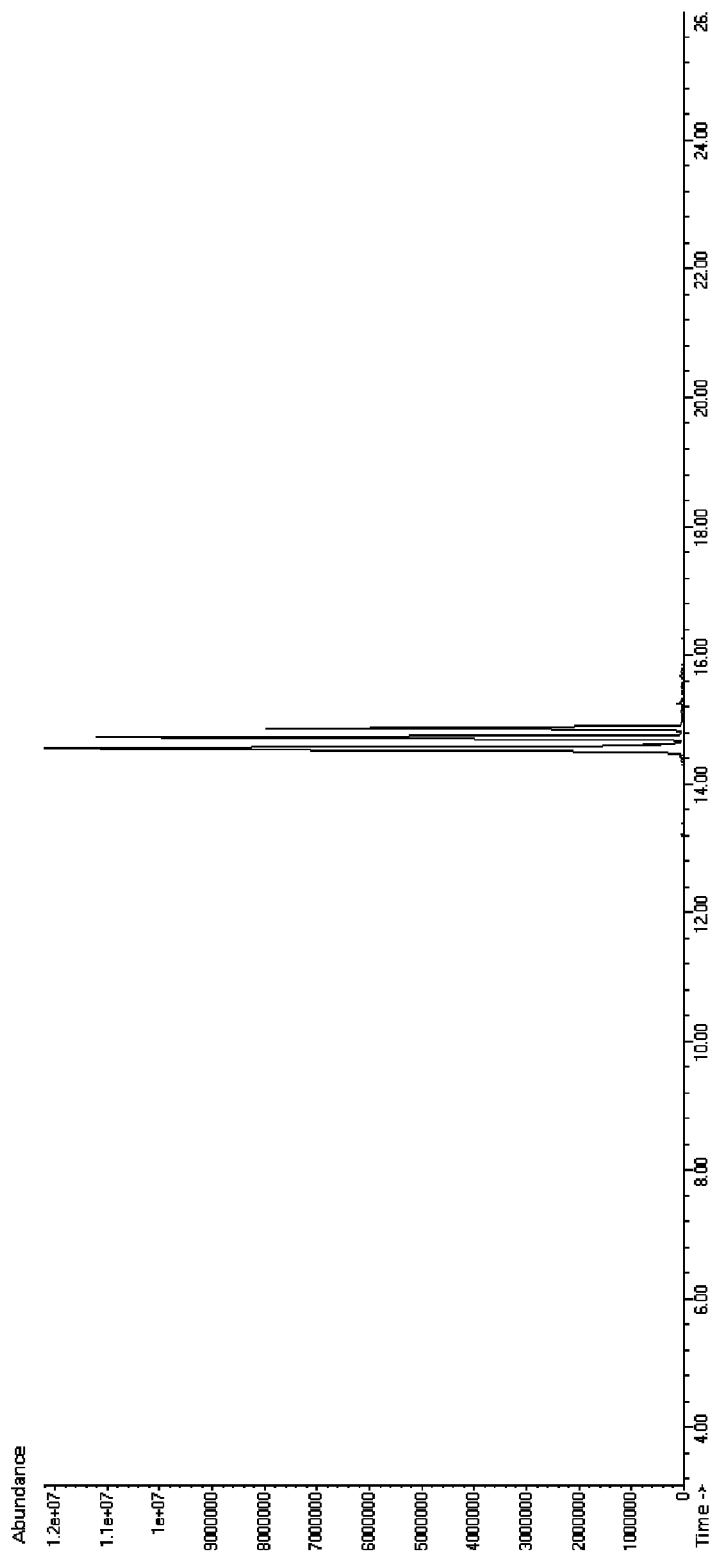
FIG. 13 is a chromatogram of a gas chromatography-mass spectrometry of methyl-10-undecenoate after the isomerization process described in Example 15 as a function of elution time (minutes).

This reaction was ran by the same method as Example 10, using 0.0028 g of $[Ru(CO)_2(EtCO_2)]_n$ and 2.0095 g of methyl 10-undecenoate. This reaction was run at 150° C. for 4 hours. The GC-MS of the product, FIG. 13, shows only a small amount of isomerization where only ~4 isomers were observable.

Figure 14:
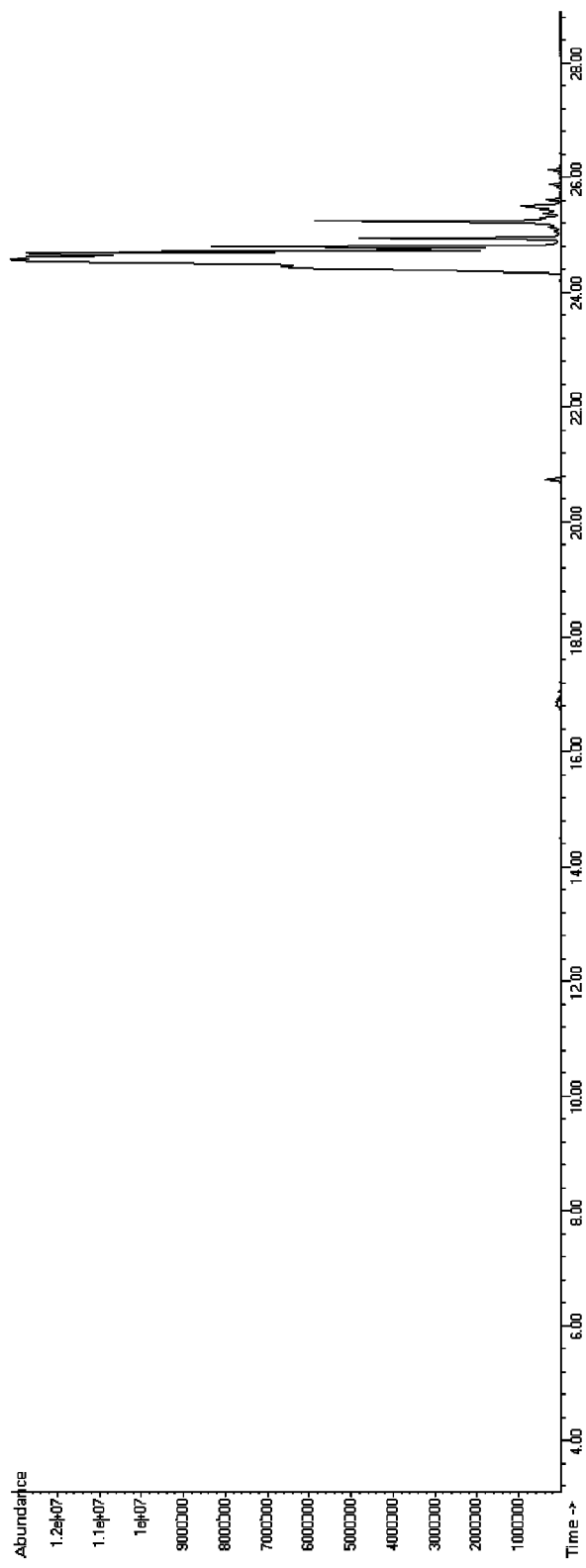
FIG. 14 is a chromatogram of a gas chromatography-mass spectrometry of methyl 9-octadecenoate after the isomerization process for 4 hours as described in Example 16 as a function of elution time (minutes).
Figure 16:
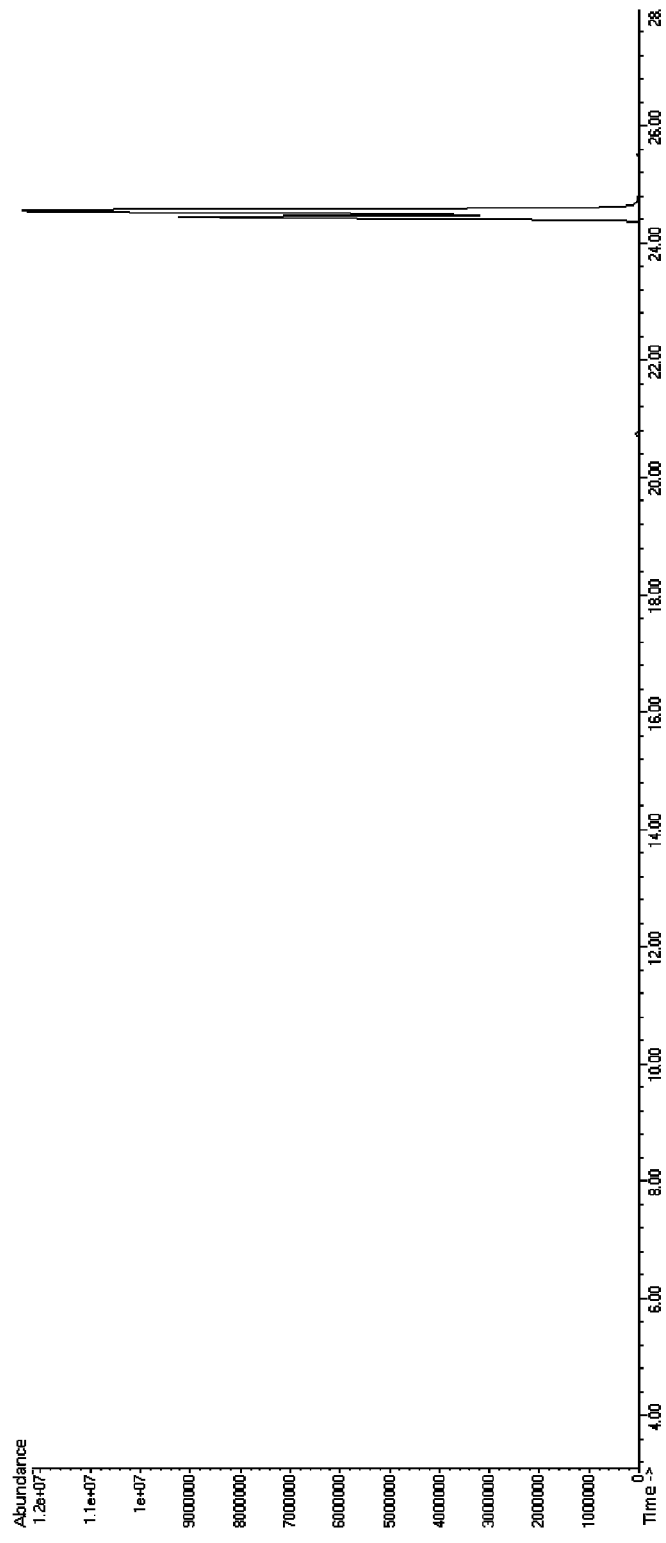
FIG. 16 is a chromatogram of a gas chromatography-mass spectrometry of methyl 9-cis-octadecenoate after the isomerization process for 4 hours as described in Example 16 as a function of elution time (minutes).

Example 16: Isomerization of Methyl 9-Cis-Octadecenoate with $[Ru(CO)_2(EtCO_2)]_n$ in 4 Hours This reaction was ran by the same method as Example 10, using 0.0026 g of $[Ru(CO)_2(EtCO_2)]_n$ and 2.0013 g of methyl 9-cis-octadecenoate. This reaction was run at 250° C. for 4 hours. The GC-MS of the product, FIG. 14, shows apparently complete steady state isomerization. The GC-MS of the product, FIG. 16, shows partial isomerization with reaction at 150° C. for 4 hours.

Figure 15:
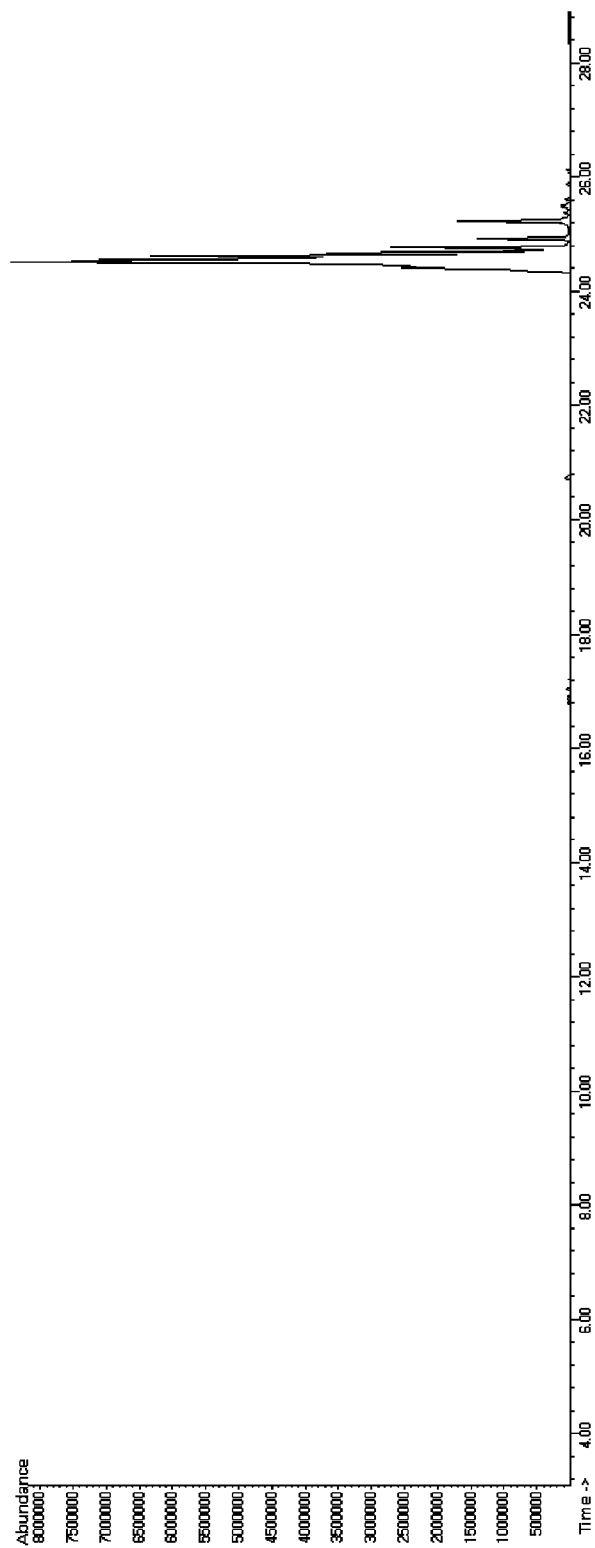
FIG. 15 is a chromatogram of a gas chromatography-mass spectrometry of methyl 9-octadecenoate after the isomerization process for 24 hours as described in Example 17 as a function of elution time (minutes).

Example 17: Isomerization of Methyl 9-Cis-Octadecenoate with $[Ru(CO)_2(EtCO_2)]_n$ in 24 Hours This reaction was ran by the same method as Example 10, using 0.0024 g of $[Ru(CO)_2(EtCO_2)]_n$ and 2.0061 g of methyl 9-cis-octadecenoate. This reaction was run at 250° C. for 4 hours. The GC-MS of the product, FIG. 15, shows apparently complete steady state isomerization.

Example 18: Isomerization of Methyl 9-Cis-Octadecenoate with $[Ru(CO)_2(EtCO_2)]_n$ in 24 Hours at 150° C.

Figure 17:
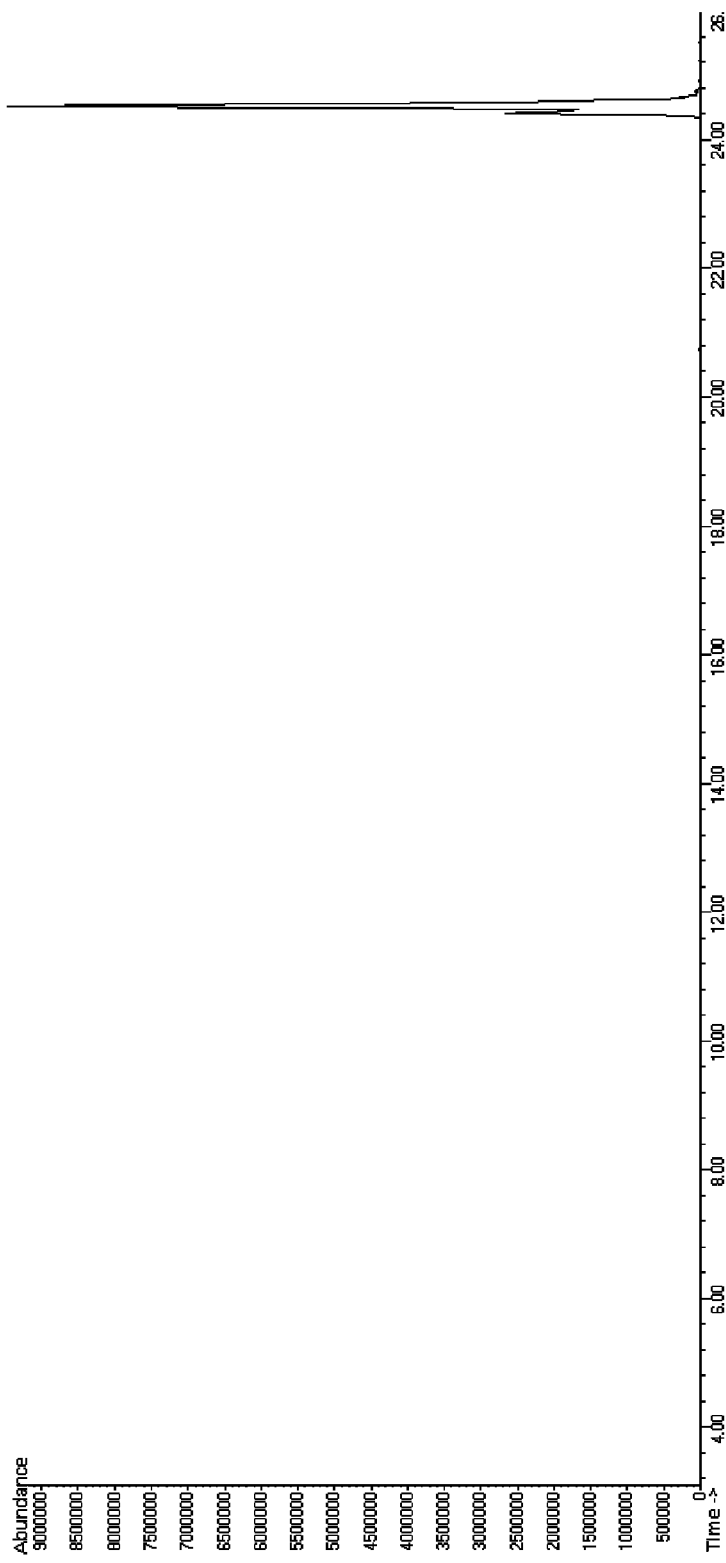
FIG. 17 is a chromatogram of a gas chromatography-mass spectrometry of methyl 9-octadecenoate after the isomerization process for 24 hours as described in Example 18 as a function of elution time (minutes).

This reaction was ran by the same method as Example 10, using 0.0031 g of $[Ru(CO)_2(EtCO_2)]_n$ and 2.0109 g of methyl 9-cis-octadecenoate. This reaction was run at 150° C. for 24 hours. The GC-MS of the product, FIG. 17, shows only a small amount of isomerization where only 2 isomers were observed.

Figure 57:
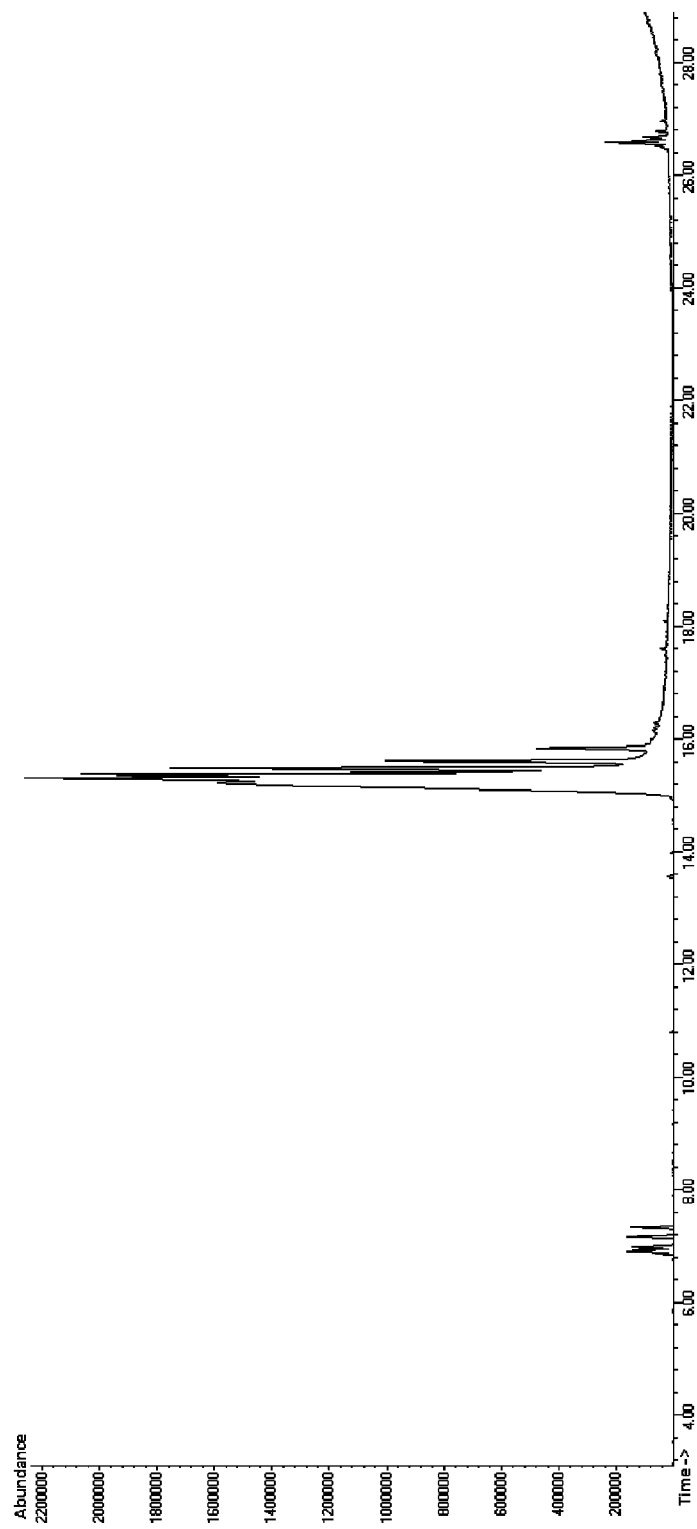
FIG. 57 is a chromatogram of a gas chromatography-mass spectrometry of 10-undecenoic acid after the decarboxylation and isomerization process as described in Example 19 as a function of elution time (minutes).
Figure 58:
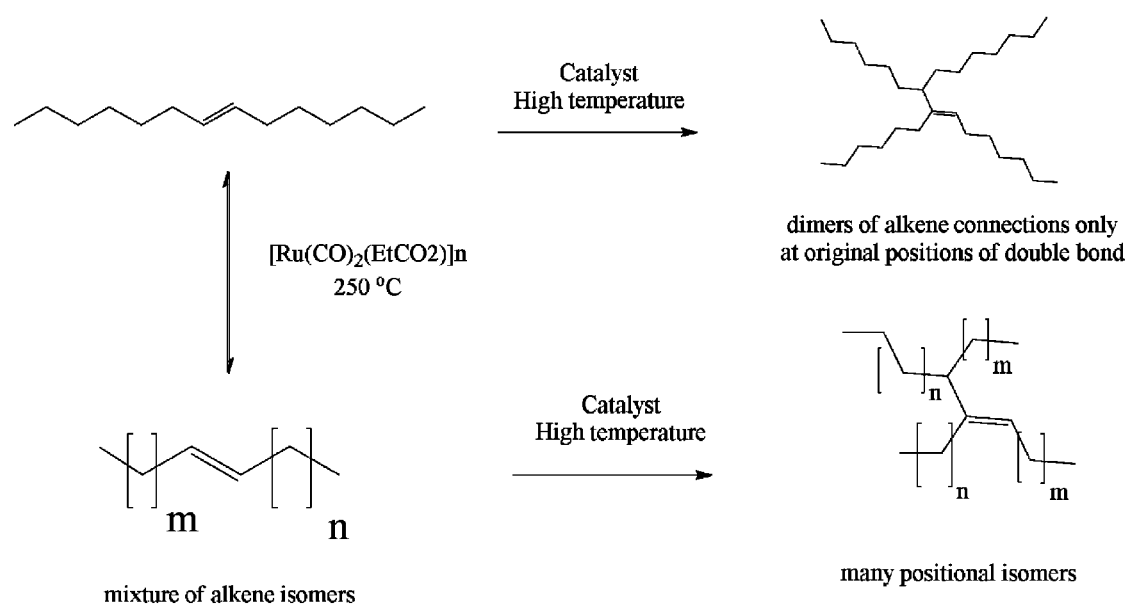
FIG. 58 is a depiction of an exemplar reaction scheme for the polymerization of an alkene, where the tandem isomerization stem gives a different product than the polymerization alone.

Example 19: The Decarboxylation and Isomerization of 10-Undecenoic Acid with $[Ru(CO)_2(EtCO_2)]_n$ at 250° C. for 4 Hours This reaction was ran by the same method as Example 10, using 0.0021 g of $[Ru(CO)_2(EtCO_2)]_n$ and 2.0460 g of 10-undecenoic acid. This reaction was run at 250° C. for 4 hours. The GC-MS chromatogram, FIG. 57, shows apparently complete steady state isomerization and alkene production of ~2%.

Figure 18:
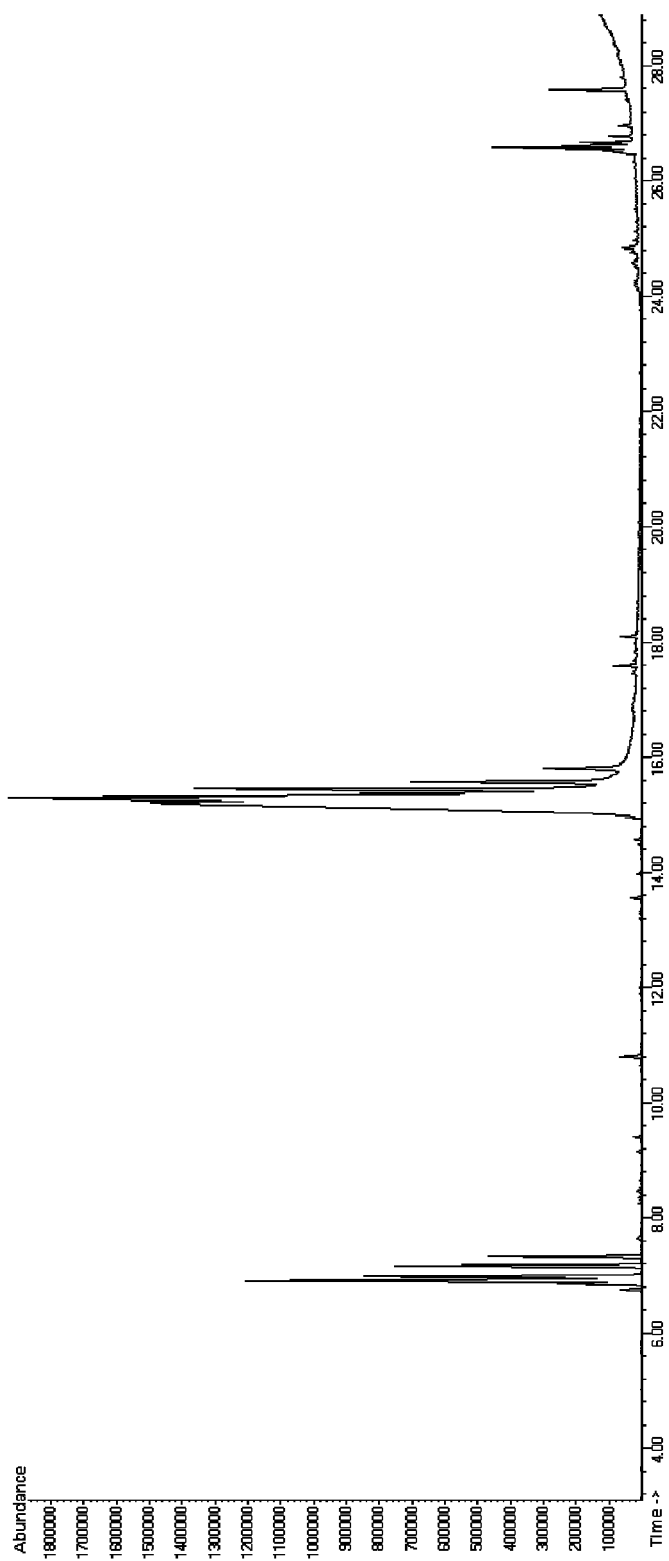
FIG. 18 is a chromatogram of a gas chromatography-mass spectrometry of 10-undecenoic acid after the decarboxylation and isomerization process as described in Example 20 as a function of elution time (minutes).

Example 20: The Decarboxylation and Isomerization of 10-Undecenoic Acid with [Ru(CO)$_2$(EtCO$_2$)]$_n$ at 250° C. for 24 Hours This reaction was ran by the same method as Example 10, using 0.0028 g of [Ru(CO)$_2$(EtCO$_2$)]$_n$ and 2.0437 g of 10-undecenoic acid. This reaction was run at 250° C. for 24 hours. The GC-MS chromatogram, FIG. 18, shows apparently complete steady state isomerization and alkene production of ~11%.

Figure 19:
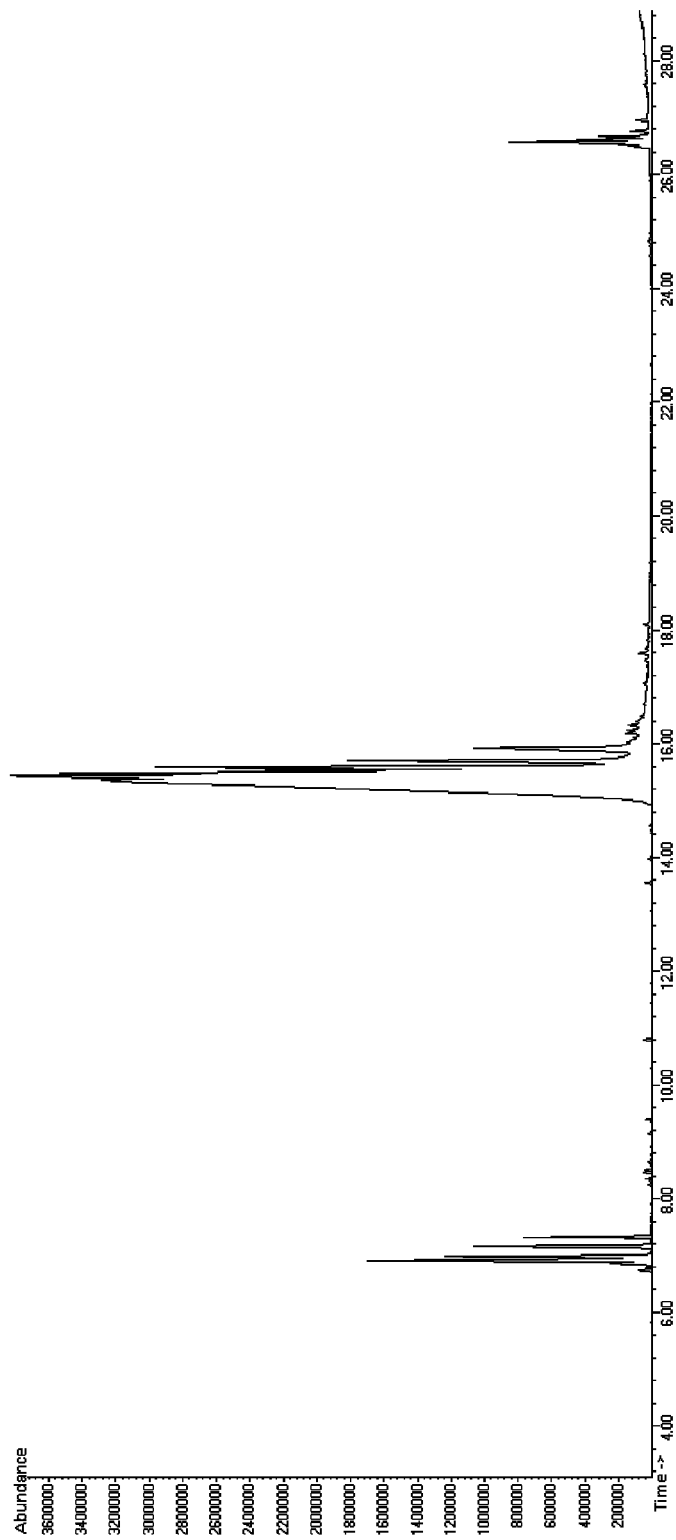
FIG. 19 is a chromatogram of a gas chromatography-mass spectrometry of 10-undecenoic acid after the decarboxylation and isomerization process as described in Example 21 as a function of elution time (minutes).

Example 21: The Decarboxylation and Isomerization of 10-Undecenoic Acid with Os$_3$(CO)$_{12}$ at 250° C. for 4 Hours A stock solution was made by the same method as Example 10 using 0.0195 g Os$_3$(CO)$_{12}$ and 5.0086 g 10-undecenoic acid. Inside an inert atmosphere dry-box, an aliquot of this stock solution, 0.5454 g was reacted combined with an additional 0.5057 g of 10-undecenoic acid in a septa capped 16×150 mm culture tube. This tube was removed from the dry-box and heated to 250° C. under an argon flow from a Schlenk line, for 2 hours, resulting in a pale yellow solution. The actual reaction temperature varied with substrate and production as some of the reactants and products reflux under these conditions which can cool the reaction tube. The GC-MS chromatogram of the product, FIG. 19, shows ~12% alkene production.

Figure 20:
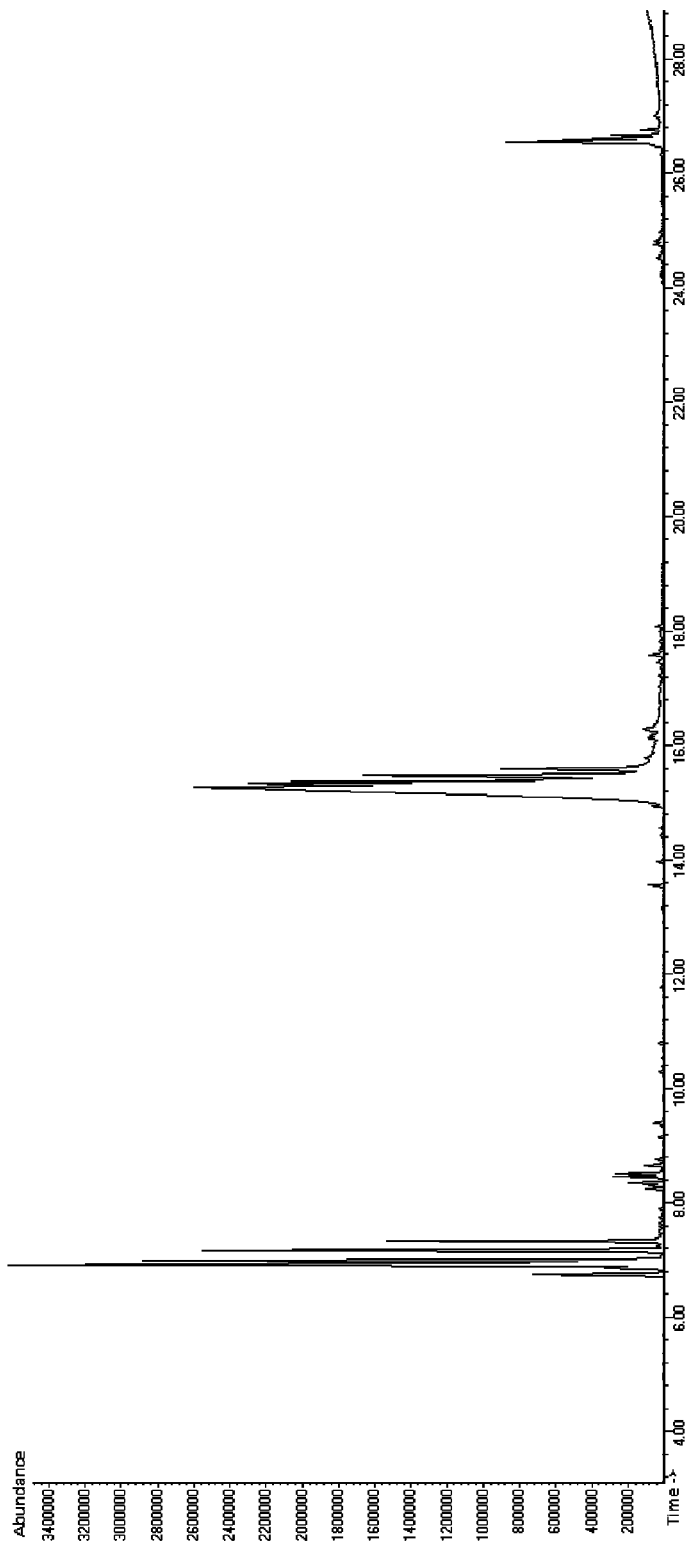
FIG. 20 is a chromatogram of a gas chromatography-mass spectrometry of 10-undecenoic acid after the decarboxylation and isomerization process as described in Example 22 as a function of elution time (minutes).

Example 22: The Decarboxylation and Isomerization of 10-Undecenoic Acid with Os$_3$(CO)$_{12}$ at 250° C. for 24 Hours The method for this reaction was identical to Example 10, using 0.6017 g stock solution, 0.5454 g additional 10-undecenoic acid. This product was bright yellow, and its GC-MS chromatogram, FIG. 20, shows ~21% alkene production.

Figure 21:
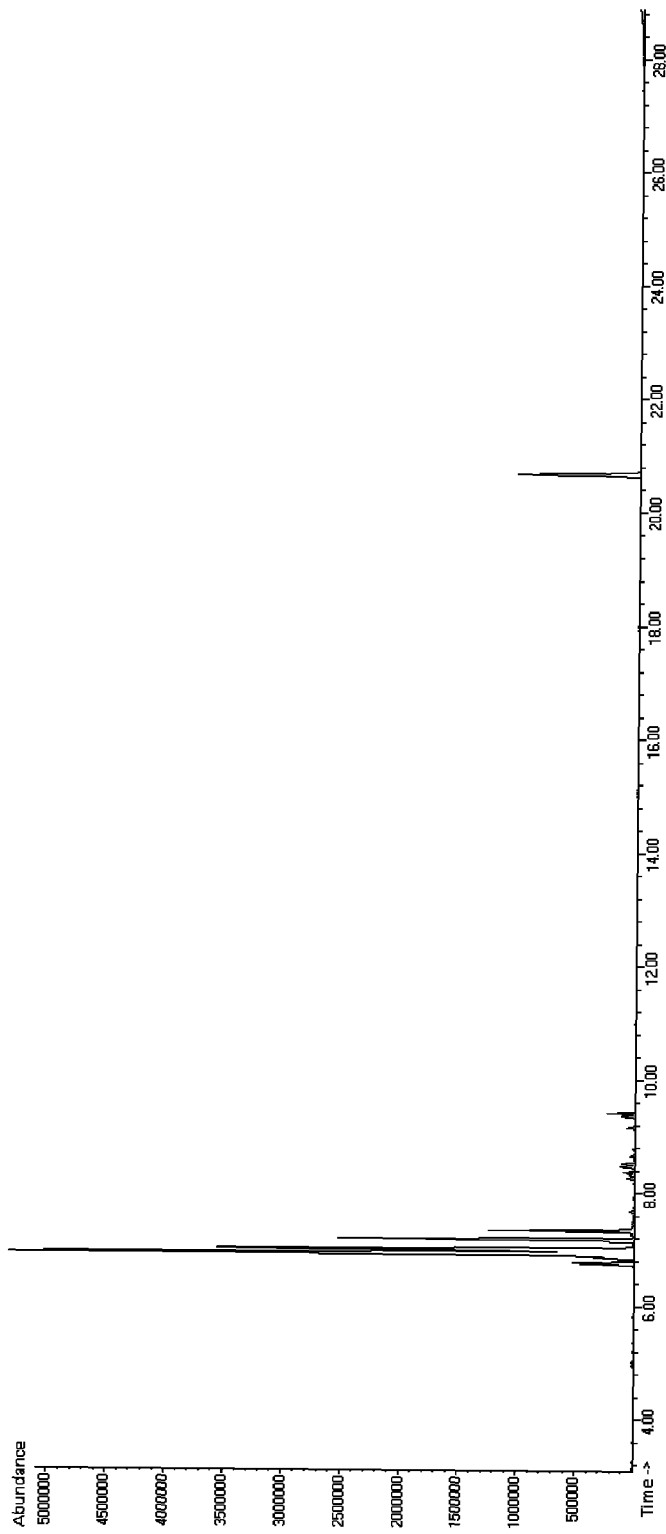
FIG. 21 is a chromatogram of a gas chromatography-mass spectrometry of 10-undecenoic acid after the decarboxylation and isomerization process as described in Example 23 as a function of elution time (minutes).
Figure 22:
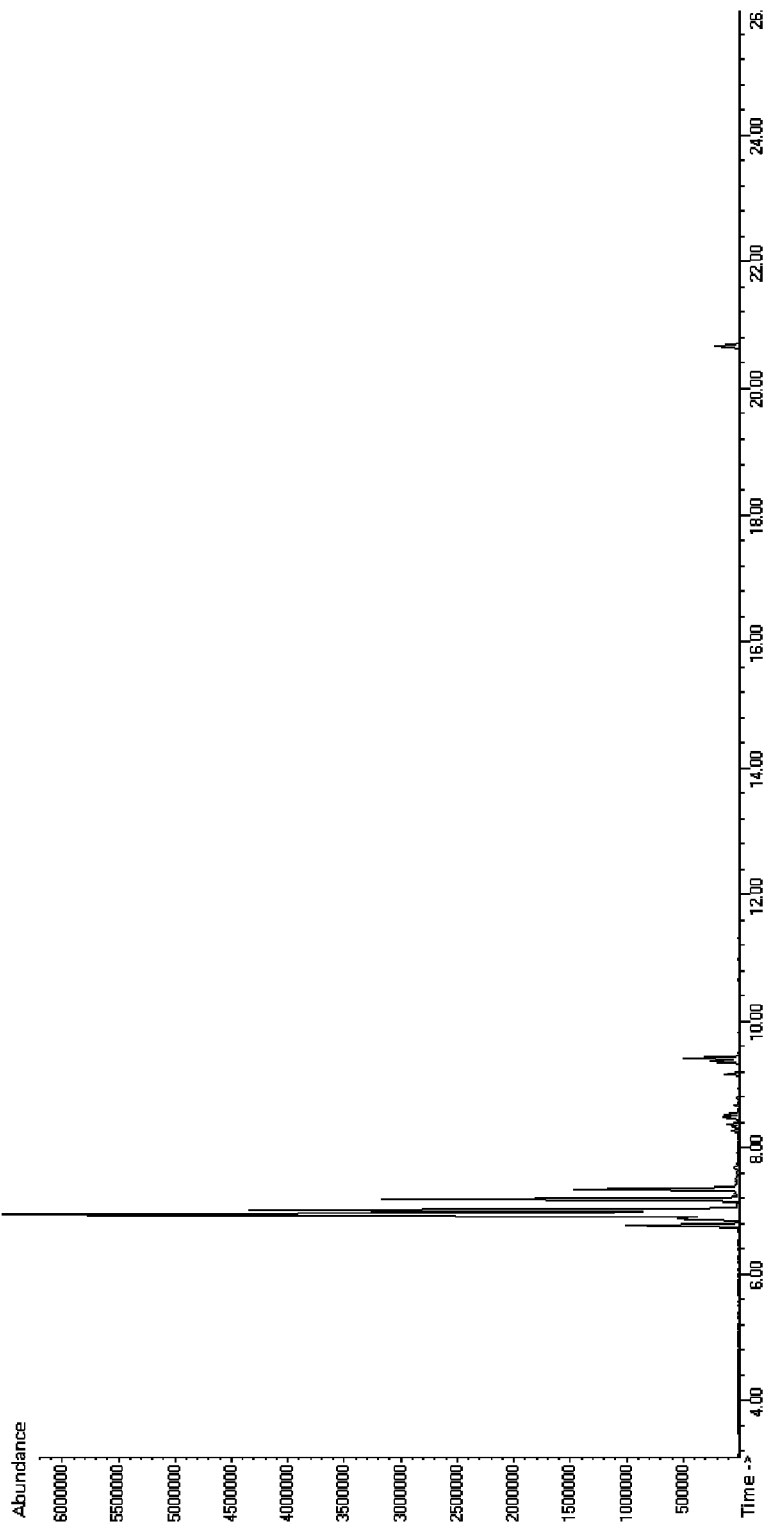
FIG. 22 is a chromatogram of a gas chromatography-mass spectrometry of 10-undecenoic acid after the decarboxylation and isomerization process as described in Example 23 as a function of elution time (minutes).
Figure 23:
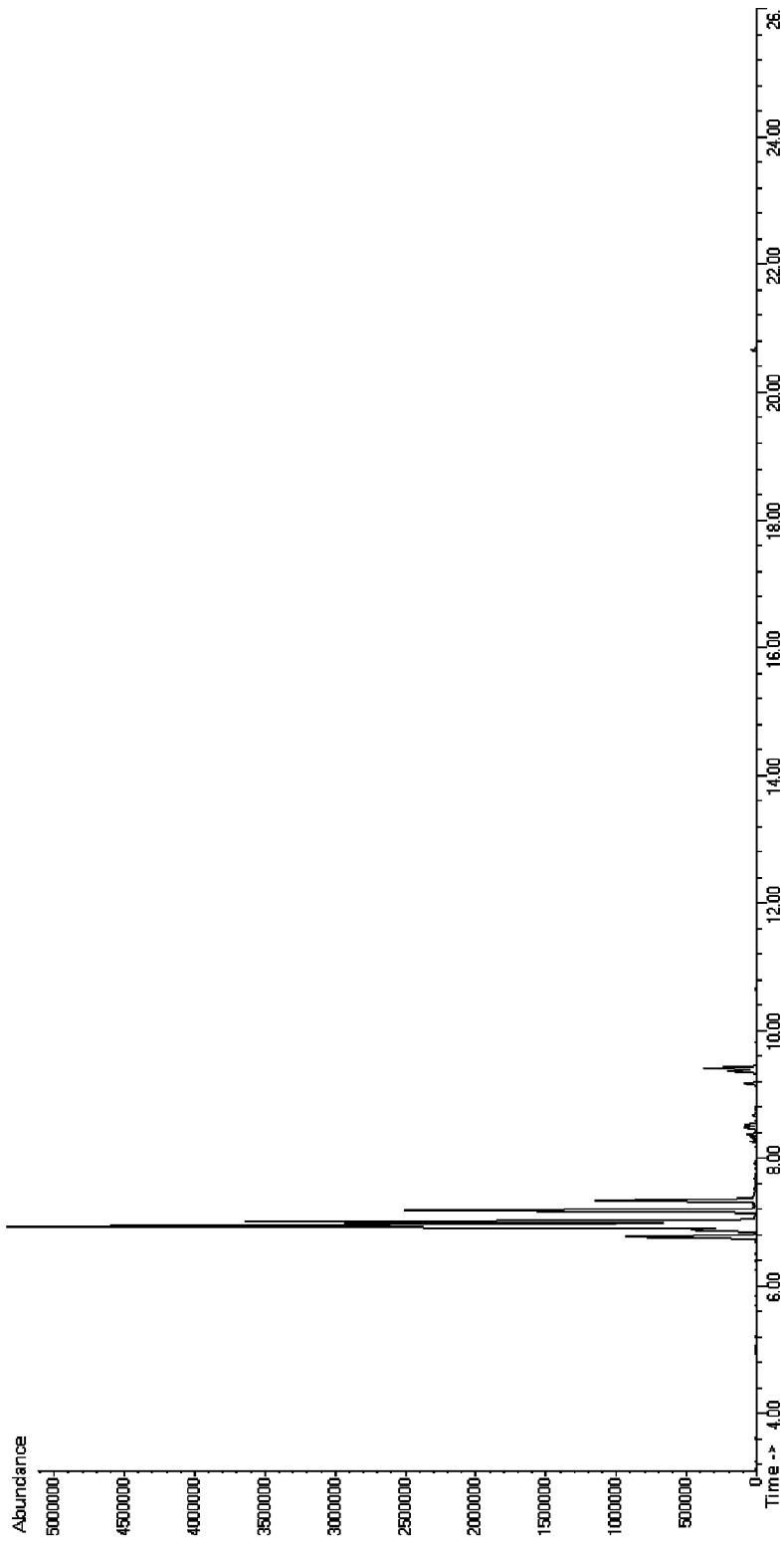
FIG. 23 is a chromatogram of a gas chromatography-mass spectrometry of 10-undecenoic acid after the decarboxylation and isomerization process as described in Example 23 as a function of elution time (minutes).
Figure 24:
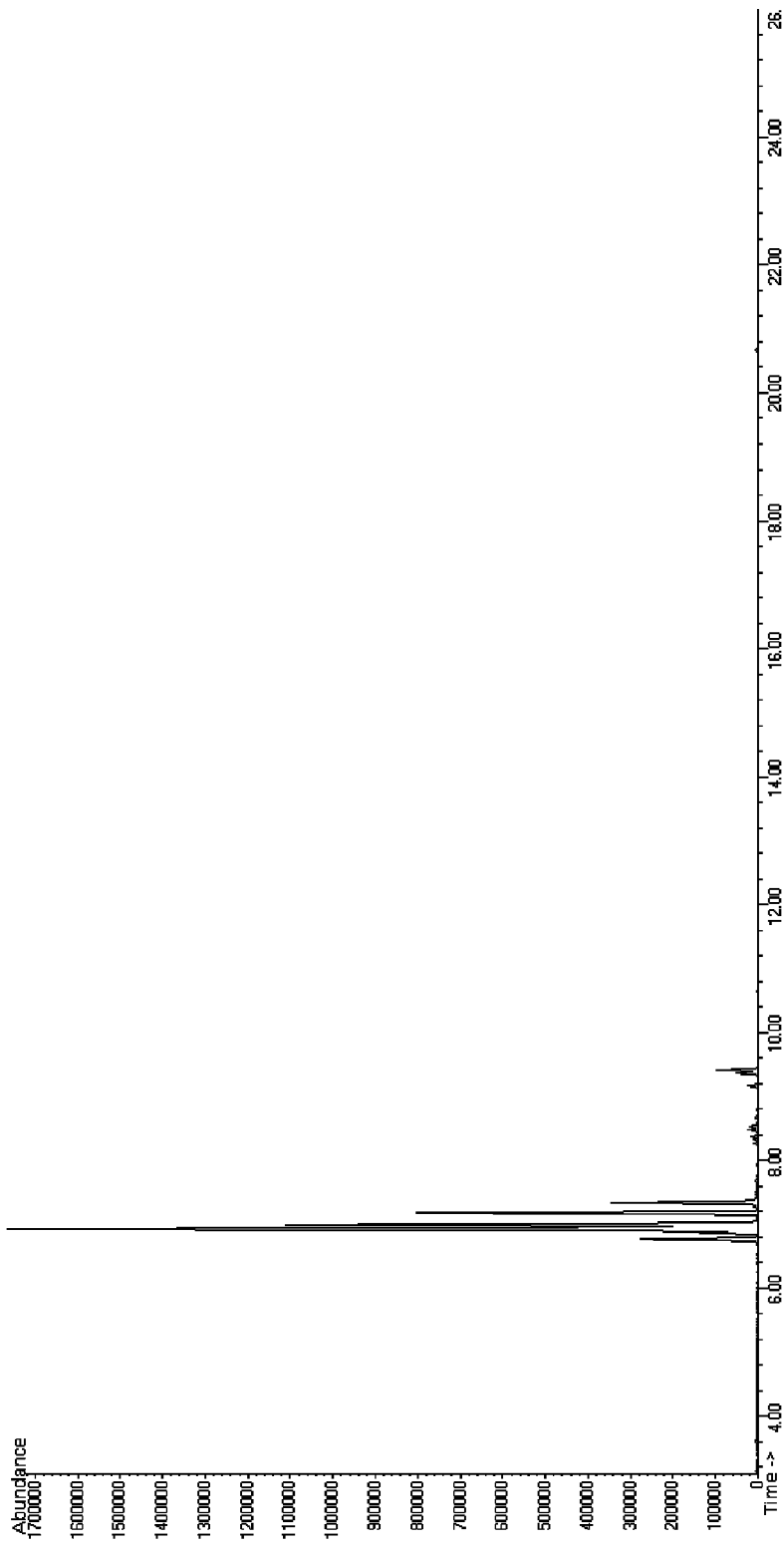
FIG. 24 is a chromatogram of a gas chromatography-mass spectrometry of 10-undecenoic acid after the decarboxylation and isomerization process as described in Example 23 as a function of elution time (minutes).

Example 23: The Decarboxylation and Isomerization of 10-Undecenoic Acid with Ru$_3$(CO)$_{12}$ Ran Over Multiple Days, with Added Eicosane, in a Reactive Distillation Inside of an inert atmosphere dry-box, 7.9091 g 10-undecenoic acid, 0.2296 g Ru$_3$(CO)$_{12}$ and 12.1056 g eicosane were added to a 50 mL round bottomed flask. The flask was attached to a condenser and the apparatus was removed from the dry-box and connected to a distillation head. A Schlenk flask was used as a receiver so samples could be taken with minimal exposure to air. Argon flow was connected to the still through a Schlenk line, and the reaction heated with an aluminum block on a hotplate, to ~250° C. Glass wool was packed around the condenser as necessary to control reflux vs. distillation rate. After 4 hours, a 1.6812 g fraction collected, analyzed by GC-MS, FIG. 21, and confirmed to be completely alkene and eicosane. The still was allowed to cool overnight under argon. The following day, an additional 2.2968 g of alkene was collected, FIG. 22, and the reactor was allowed to cool and 2.2360 g of fresh 10-undecenoic acid was added to the vessel which was left overnight under argon. Further fractions of alkene were collected on days 3 and 4, FIG. 23 and FIG. 24, respectively, between which, 0.6052 g of fresh 10-undecenoic acid was added. Overall, a total of 4.53 g of alkene was collected, and the 10-undecenoic acid in the reaction pot was isomerized to an apparently complete steady state.

Example 23a Control Experiment

Figure 25:
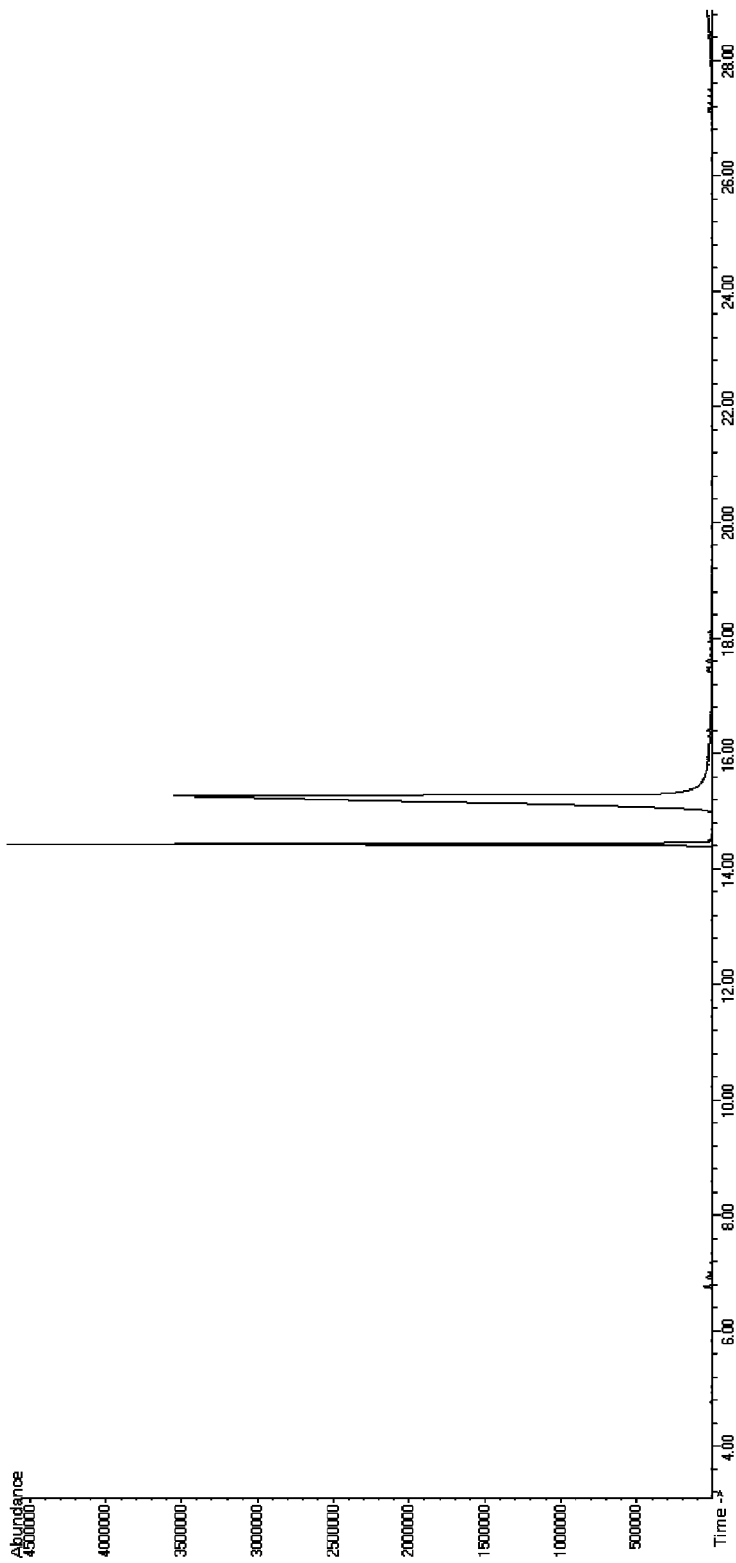
FIG. 25 is a chromatogram of a gas chromatography-mass spectrometry of undecanoic acid as described in Example 23A as a function of elution time (minutes).

The Reaction of a Saturated Fatty Acid, Undecanoic Acid with Ru$_3$(CO)$_{12}$ at 250° C. for 4 Hours This reaction was run by the method in Example 10. A mass of 1.0633 g of undecanoic acid was used with 0.0095 g Ru$_3$(CO)$_{12}$. As an internal standard, 0.1982 g of pentadecane was also added to the reaction. The resultant GC-MS, FIG. 25, shows no reaction products were produced in any quantity over 1%.

Figure 26:
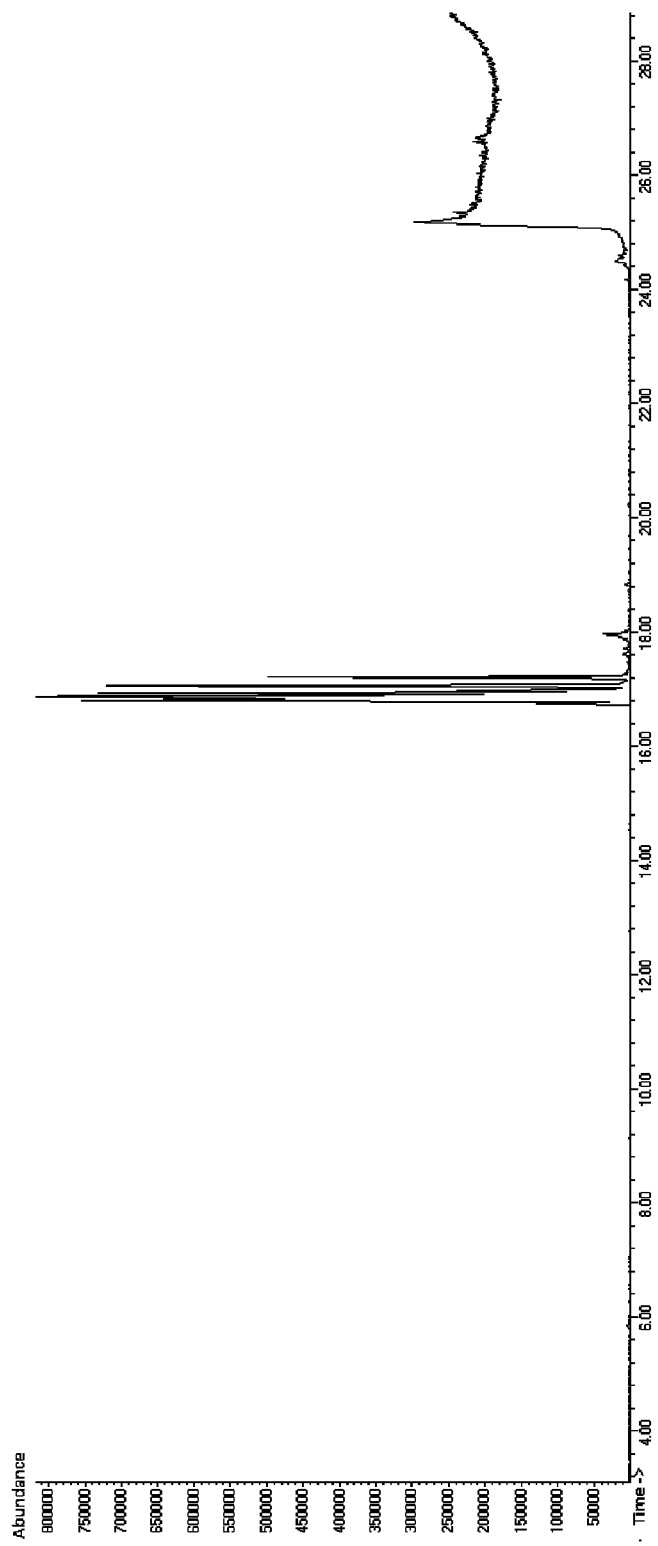
FIG. 26 is a chromatogram of a gas chromatography-mass spectrometry of 9-cis-octadecenoic acid after the decarboxylation and isomerization process as described in Example 24 as a function of elution time (minutes).

Example 24: The Decarboxylation and Isomerization of 9-Cis-Octadecenoic Acid with [Ru(CO)$_2$(EtCO$_2$)]$_n$ at 250° C. for 4 Hours This reaction was ran by the same method as Example 10, using 0.0020 g of [Ru(CO)$_2$(EtCO$_2$)]$_n$ and 2.0534 g of 9-cis-octadecenoic acid. This reaction was run at 250° C. for 4 hours. The GC-MS chromatogram, FIG. 26, shows apparently complete steady state isomerization and alkene production of nearly 50%.

Figure 27:
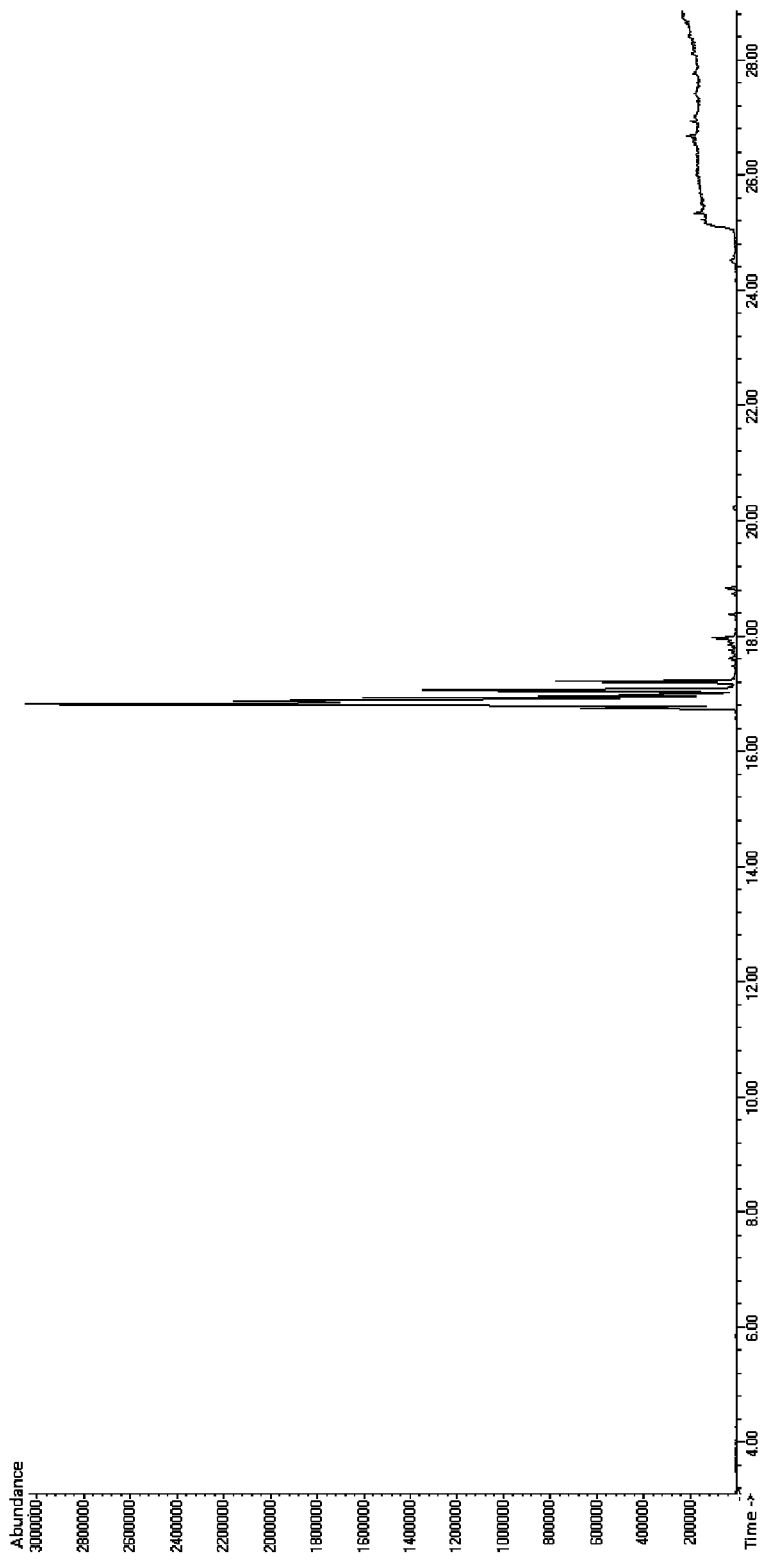
FIG. 27 is a chromatogram of a gas chromatography-mass spectrometry of 9-cis-octadecenoic acid after the decarboxylation and isomerization process as described in Example 25 as a function of elution time (minutes).

Example 25: The Decarboxylation and Isomerization of 9-Cis-Octadecenoic Acid with [Ru(CO)$_2$(EtCO$_2$)]$_n$ at 250° C. for 24 Hours This reaction was ran by the same method as Example 10, using 0.0029 g of [Ru(CO)$_2$(EtCO$_2$)]$_n$ and 2.0134 g of 9-cis-octadecenoic acid. This reaction was run at 250° C. for 24 hours. The GC-MS chromatogram, FIG. 27, shows apparently complete steady state isomerization and nearly complete alkene production.

Figure 28:
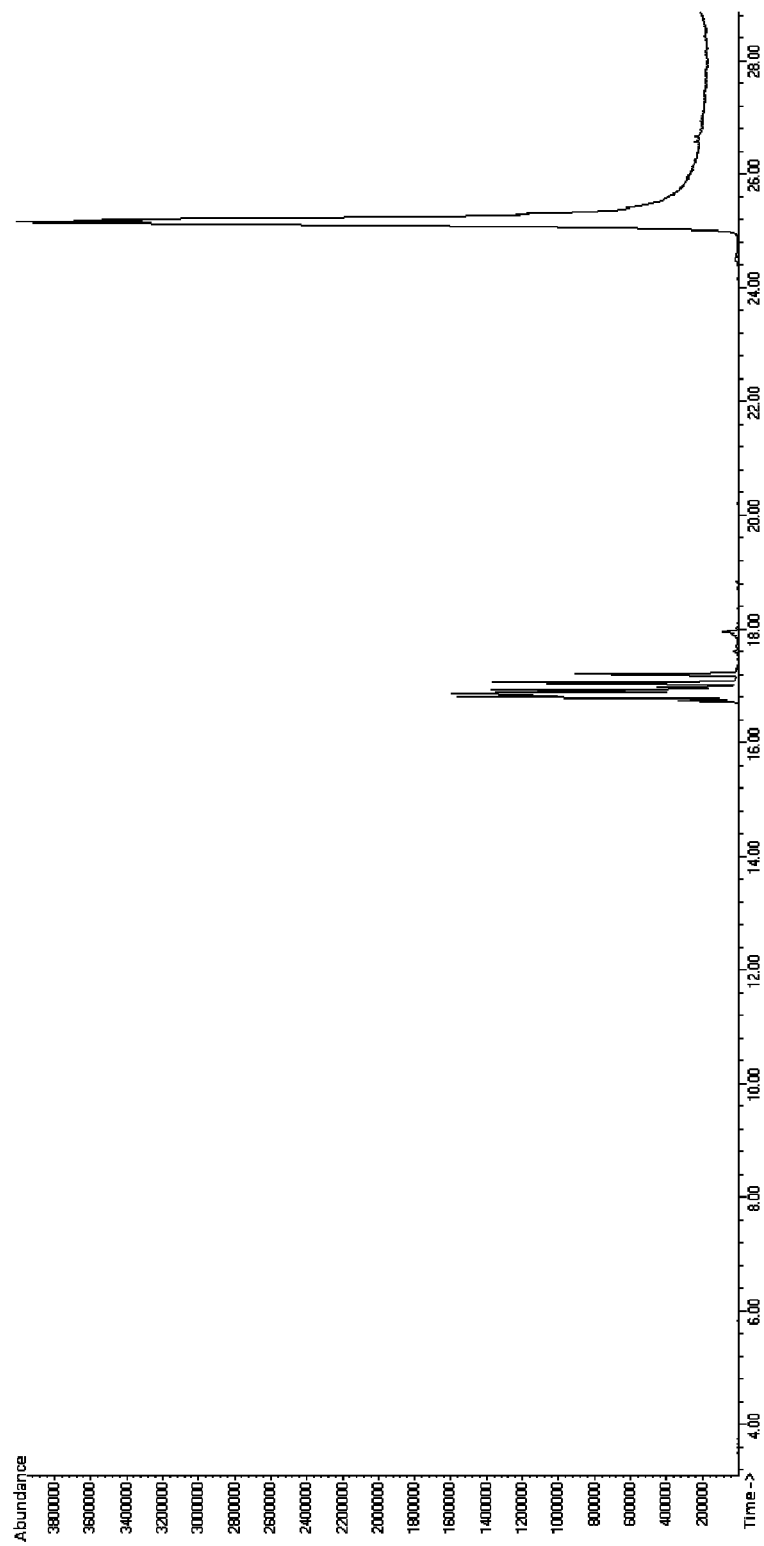
FIG. 28 is a chromatogram of a gas chromatography-mass spectrometry of 9-cis-octadecenoic acid after the decarboxylation and isomerization process as described in Example 26 as a function of elution time (minutes).

Example 26: The Decarboxylation and Isomerization of 9-Cis-Octadecenoic Acid with Ru$_3$O(EtCO$_2$)$_m$(H$_2$O)$_n$ at 250° C. for 4 Hours This reaction was ran by the same method as Example 10, using 0.0024 g of Ru$_3$O(EtCO$_2$)$_m$(H$_2$O)$_n$ and 2.0155 g of 9-cis-octadecenoic acid. This reaction was run at 250° C. for 4 hours. The GC-MS chromatogram, FIG. 28, shows apparently complete steady state isomerization and alkene production of ~12%.

Figure 29:
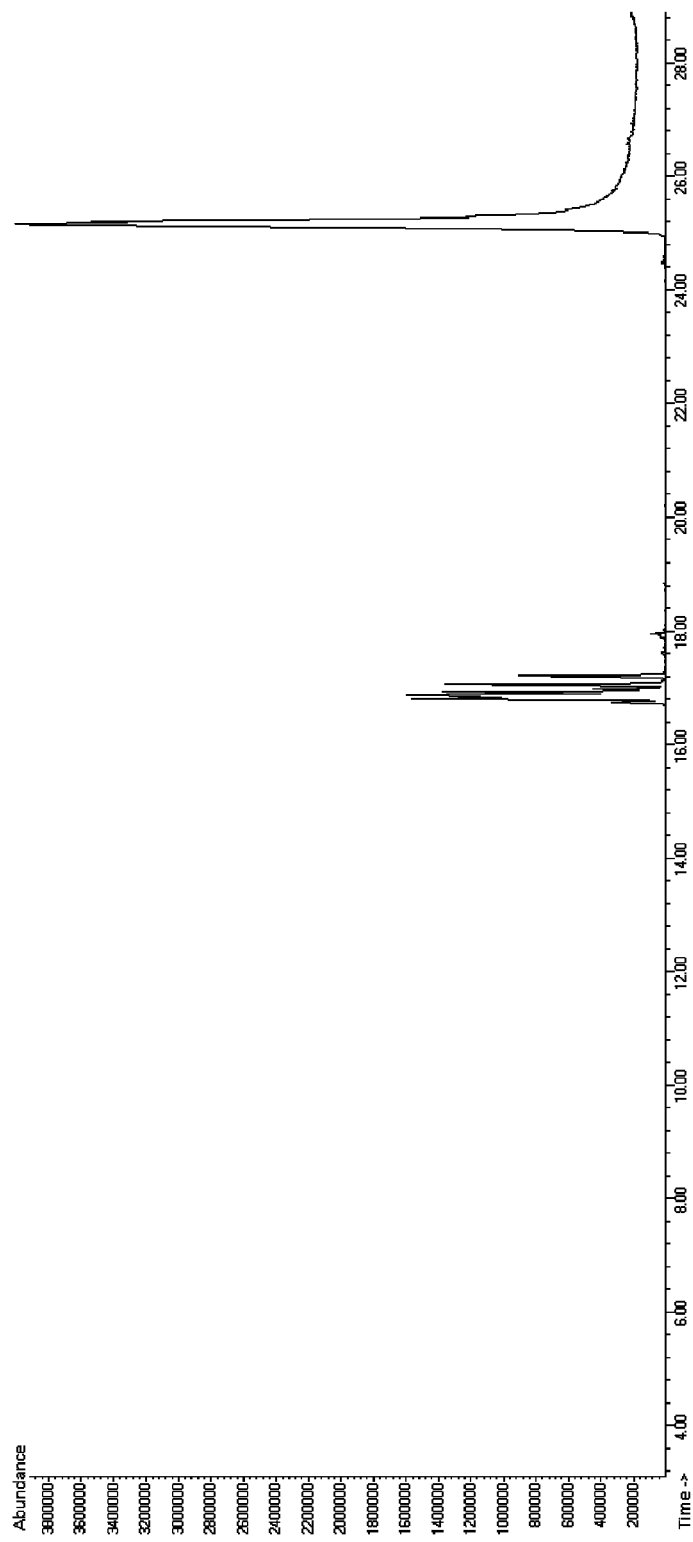
FIG. 29 is a chromatogram of a gas chromatography-mass spectrometry of 9-cis-octadecenoic acid after the decarboxylation and isomerization process as described in Example 27 as a function of elution time (minutes).

Example 27: The Decarboxylation and Isomerization of 9-Cis-Octadecenoic Acid with Ru$_3$O(EtCO$_2$)$_m$(H$_2$O)$_n$ at 250° C. for 24 Hours This reaction was ran by the same method as Example 10, using 0.0026 g of Ru$_3$O(EtCO$_2$)$_m$(H$_2$O)$_n$ and 2.0038 g of 9-cis-octadecenoic acid. This reaction was run at 250° C. for 24 hours. The GC-MS chromatogram, FIG. 29, shows apparently complete steady state isomerization and alkene production of ~22%.

Figure 30:
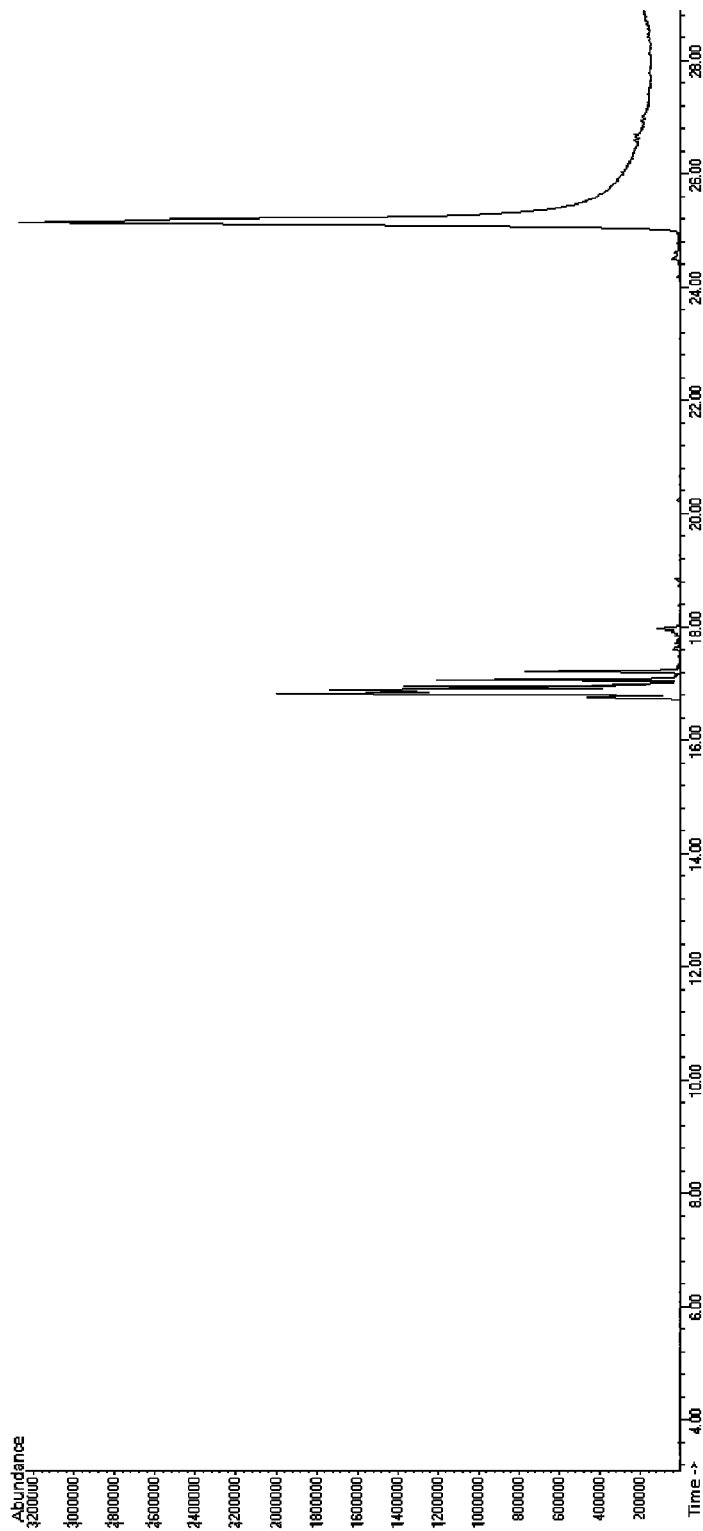
FIG. 30 is a chromatogram of a gas chromatography-mass spectrometry of 9-cis-octadecenoic acid after the decarboxylation and isomerization process as described in Example 28 as a function of elution time (minutes).

Example 28: The Decarboxylation and Isomerization of 9-Cis-Octadecenoic Acid with Ru$_3$(CO)$_{12}$ at 250° C. for 4 Hours A stock solution was made by the same method as Example 10 using 0.0128 g Ru$_3$(CO)$_{12}$ and 5.0102 g 9-cisoctadecenoic acid. Inside an inert atmosphere dry-box, an aliquot of this stock solution, 0.5023 g was reacted combined with an additional 0.5085 g of 9-cis-octadecenoic acid in a septa capped 16×150 mm culture tube. This tube was removed from the dry-box and heated to 250° C. under an argon flow from a Schlenk line, for 4 hours, resulting in a pale yellow solution. The GC-MS chromatogram of the product, FIG. 30, shows ~28% alkene production.

Figure 31:
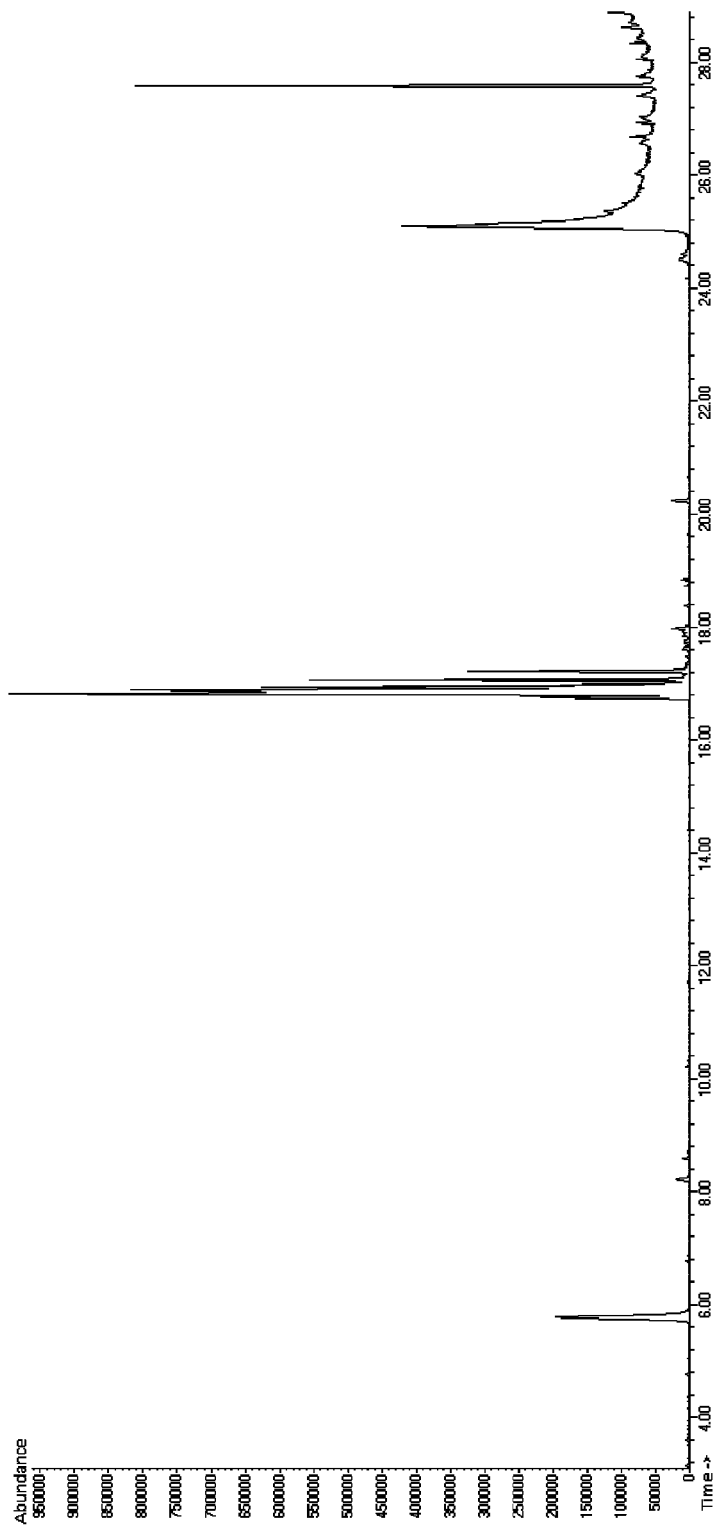
FIG. 31 is a chromatogram of a gas chromatography-mass spectrometry of 9-cis-octadecenoic acid after the decarboxylation and isomerization process as described in Example 29 as a function of elution time (minutes).

Example 29: The Decarboxylation and Isomerization of 9-Cis-Octadecenoic Acid with $Ru_3(CO)_{12}$ at 250° C. for 24 Hours The method for this reaction was identical to Example 10, using 0.5028 g stock solution, 0.5061 g additional 9-cis-octadecenoic acid. This product was bright yellow, and its GC-MS chromatogram, FIG. 31, shows ~45% alkene production.

Figure 32:
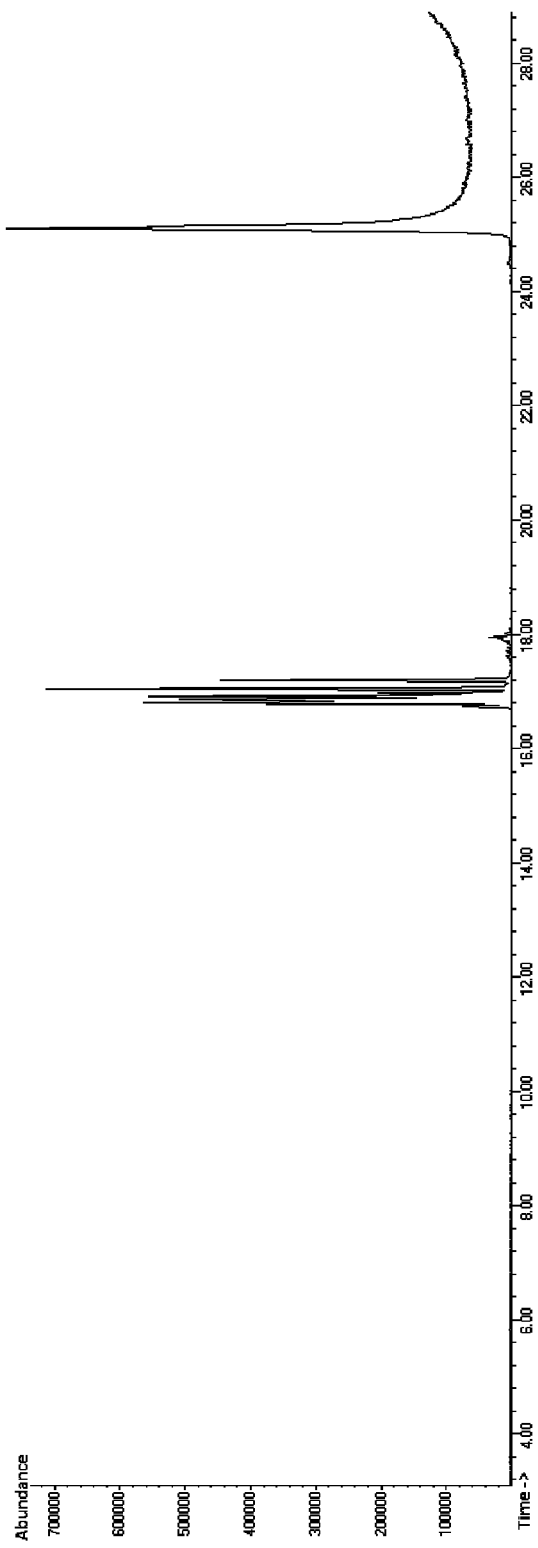
FIG. 32 is a chromatogram of a gas chromatography-mass spectrometry of 9-cis-octadecenoic acid after the decarboxylation and isomerization process as described in Example 30 as a function of elution time (minutes).

Example 30: The Decarboxylation and Isomerization of 9-Cis-Octadecenoic Acid with $Os_3(CO)_{12}$ at 250° C. for 4 Hours A stock solution was made by the same method as Example 10 using 0.0165 g $Os_3(CO)_{12}$ and 5.0086 g 9-cis-octadecenoic acid. Inside an inert atmosphere dry-box, an aliquot of this stock solution, 0.5013 g was reacted combined with an additional 0.5345 g of 9-cis-octadecenoic acid in a septa capped 16×150 mm culture tube. This tube was removed from the dry-box and heated to 250° C. under an argon flow from a Schlenk line, for 4 hours, resulting in a pale yellow solution. The GC-MS chromatogram of the product, FIG. 32, shows ~28% alkene production.

Figure 33:
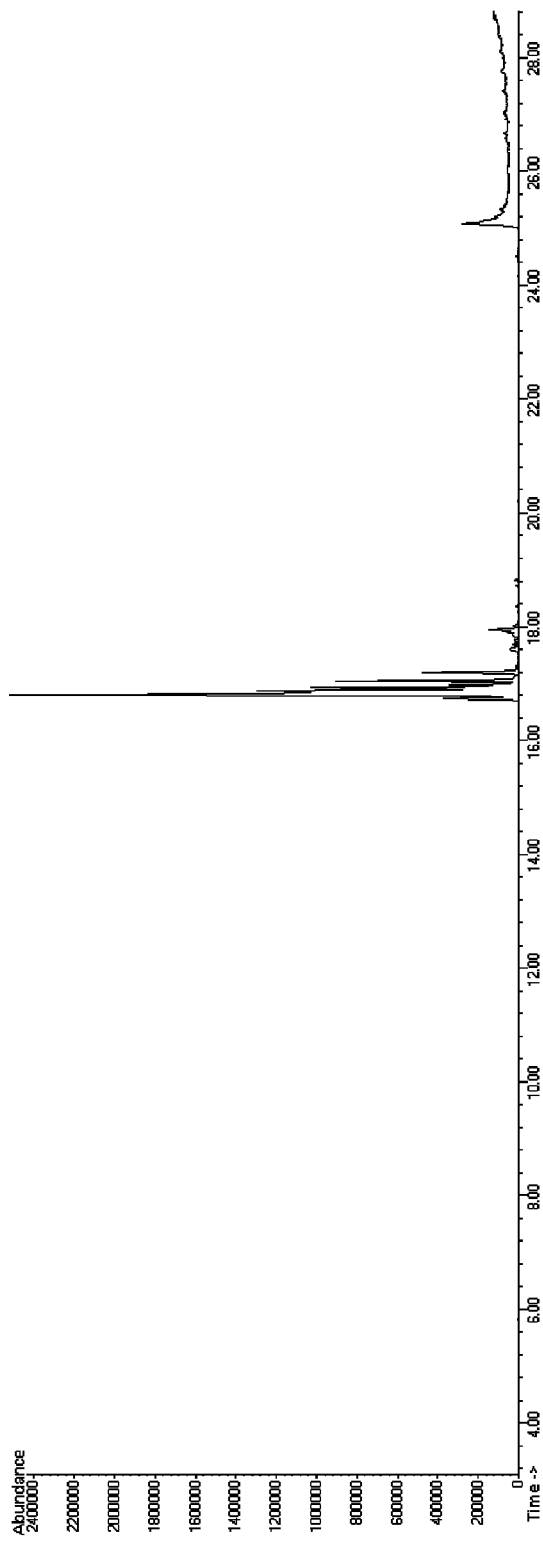
FIG. 33 is a chromatogram of a gas chromatography-mass spectrometry of 9-cis-octadecenoic acid after the decarboxylation and isomerization process as described in Example 31 as a function of elution time (minutes).

Example 31: The Decarboxylation and Isomerization of 9-Cis-Octadecenoic with $Os_3(CO)_{12}$ at 250° C. for 24 Hours The method for this reaction was identical to Example 10, using 0.5379 g stock solution, 0.5180 g additional 9-cis-octadecenoic acid. This product was bright yellow, and its GC-MS chromatogram, FIG. 33, shows ~45% alkene production.

Figure 34:
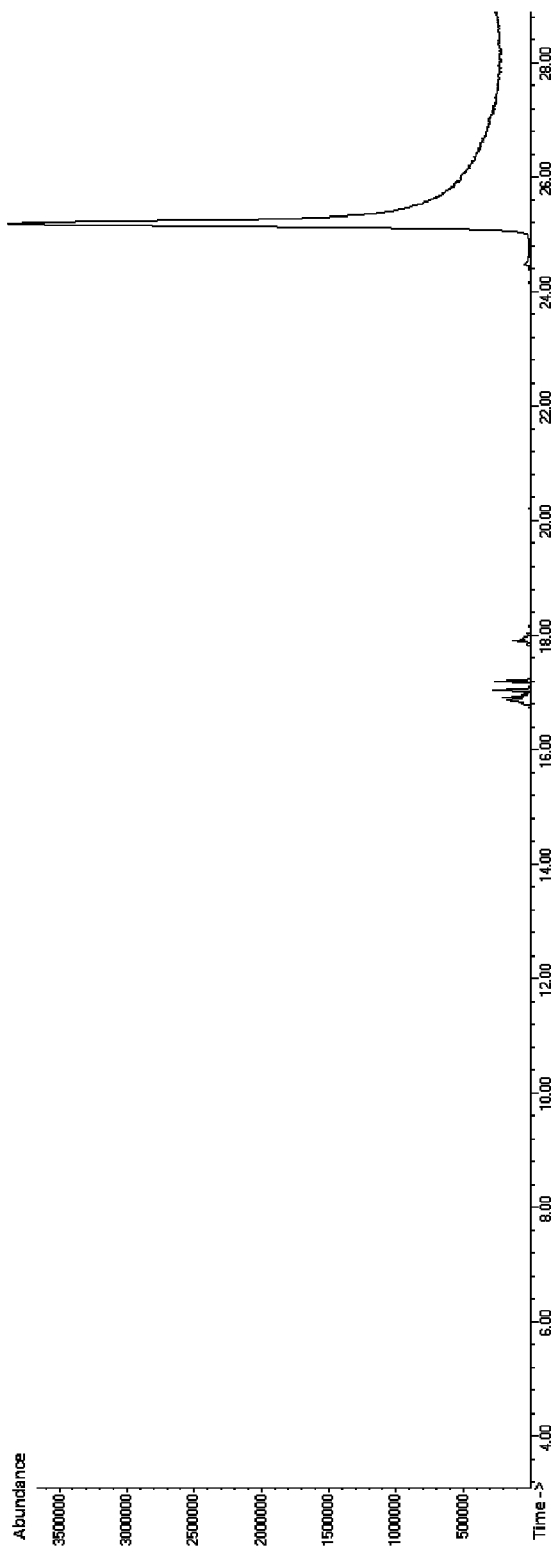
FIG. 34 is a chromatogram of a gas chromatography-mass spectrometry of 9-cis-octadecenoic acid after the decarboxylation and isomerization process as described in Example 32 as a function of elution time (minutes).

Example 32: The Decarboxylation and Isomerization of 9-Cis-Octadecenoic Acid with Benzylidene-Bis(Tricyclohexylphosphine)Dichlororuthenium, Grubbs Generation I, at 250° C. for 4 Hours This reaction was ran by the same method as Example 10, using 0.0021 g of Grubbs Generation 1, and 2.0349 g of 9-cis-octadecenoic acid. In this instance, the Grubbs catalyst is used as a precursor for the decarboxylation and isomerization reaction and not as a metathesis catalyst. This reaction was run at 250° C. for 4 hours. The GC-MS chromatogram, FIG. 34, shows apparently complete steady state isomerization and alkene production of ~1%.

Figure 35:
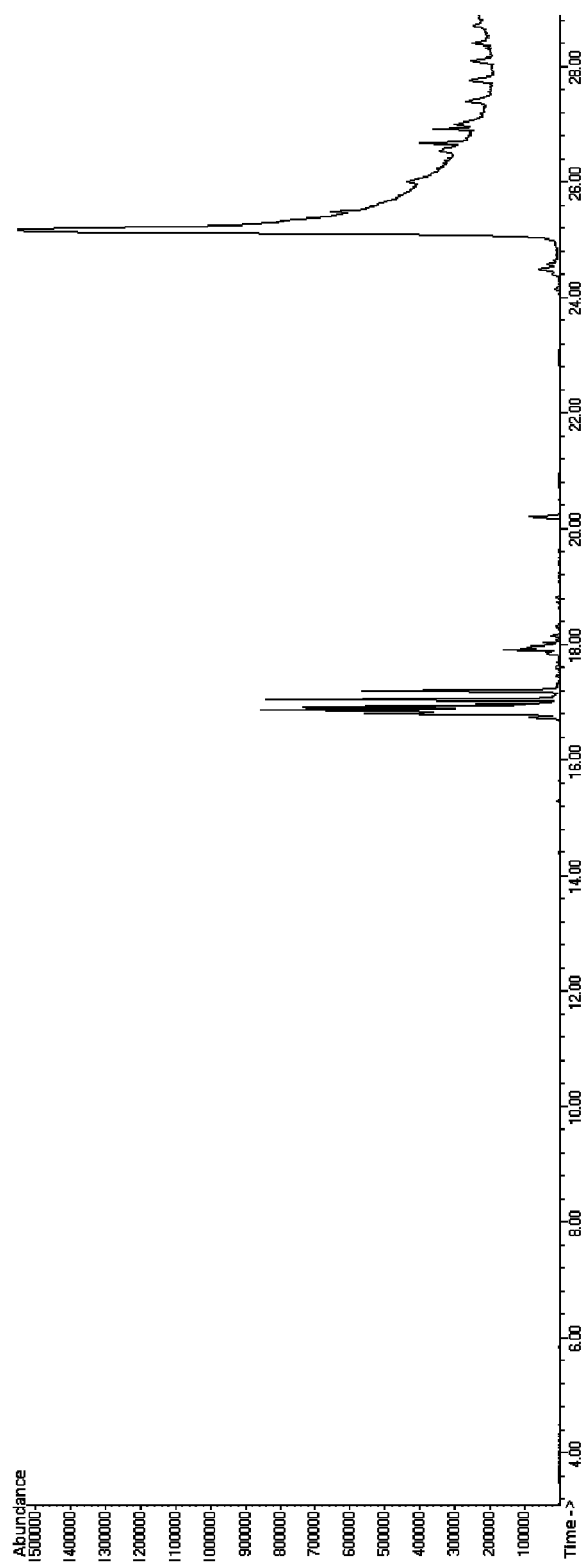
FIG. 35 is a chromatogram of a gas chromatography-mass spectrometry of 9-cis-octadecenoic acid after the decarboxylation and isomerization process as described in Example 33 as a function of elution time (minutes).

Example 33: The Decarboxylation and Isomerization of 9-Cis-Octadecenoic Acid with Benzylidene-Bis(Tricyclohexylphosphine)Dichlororuthenium, Grubbs Generation I, at 250° C. for 24 Hours This reaction was run by the same method as Example 10, using 0.0024 g of Grubbs Generation I, and 2.0603 g of 9-cis-octadecenoic acid. In this instance, the Grubbs catalyst is used as a precursor for the decarboxylation and isomerization reaction and not as a metathesis catalyst. This reaction was run at 250° C. for 24 hours. The GC-MS chromatogram, FIG. 35, shows apparently complete steady state isomerization and alkene production of ~9%.

Figure 36:
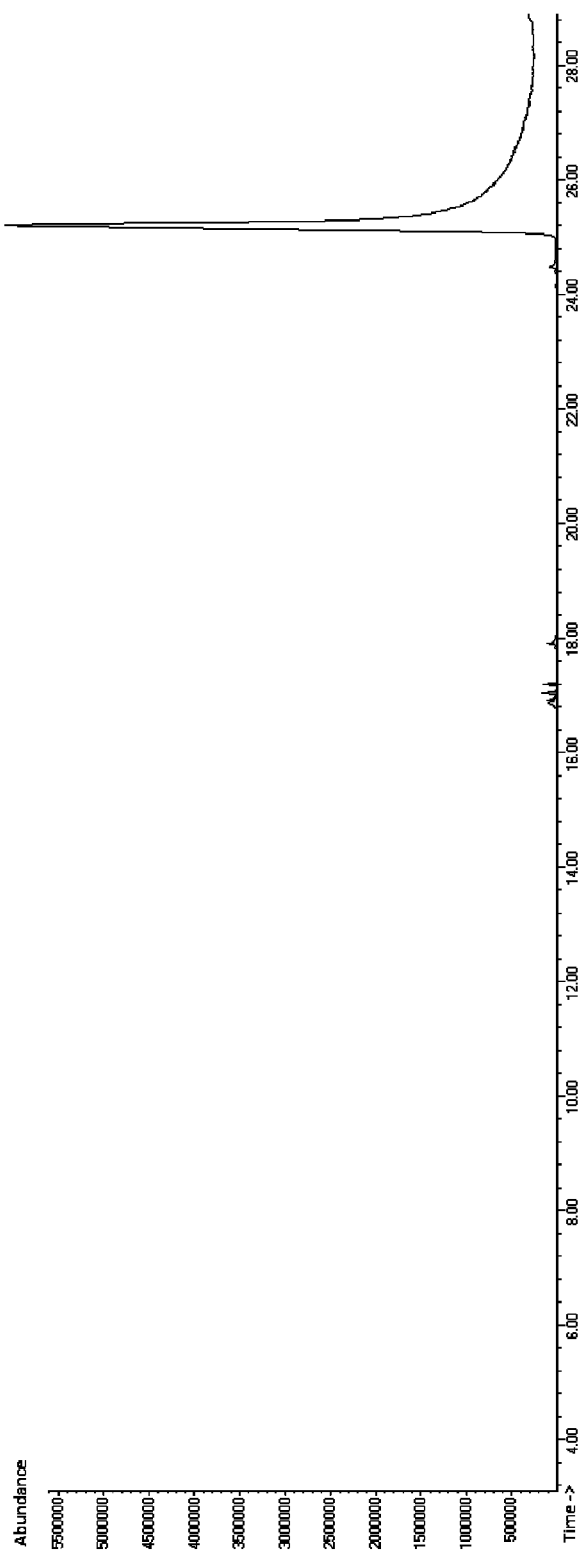
FIG. 36 is a chromatogram of a gas chromatography-mass spectrometry of 9-cis-octadecenoic acid after the decarboxylation and isomerization process as described in Example 34 as a function of elution time (minutes).

Example 34: The Decarboxylation and Isomerization of 9-Cis-Octadecenoic Acid with Bis(Tricyclohexylphosphine)Isopentenylidene Dichlororuthenium, at 250° C. for 4 Hours This reaction was ran by the same method as Example 10, using 0.0018 g of Bis(tricyclohexylphosphine)isopentenylidene dichlororuthenium, and 2.0208 g of 9-cis-octadecenoic acid. This reaction was run at 250° C. for 4 hours. In this instance, the Grubbs catalyst is used as a precursor for the decarboxylation and isomerization reaction and not as a metathesis catalyst. The GC-MS chromatogram, FIG. 36, shows apparently complete steady state isomerization isomerization and alkene production of greater than 1%.

Figure 37:
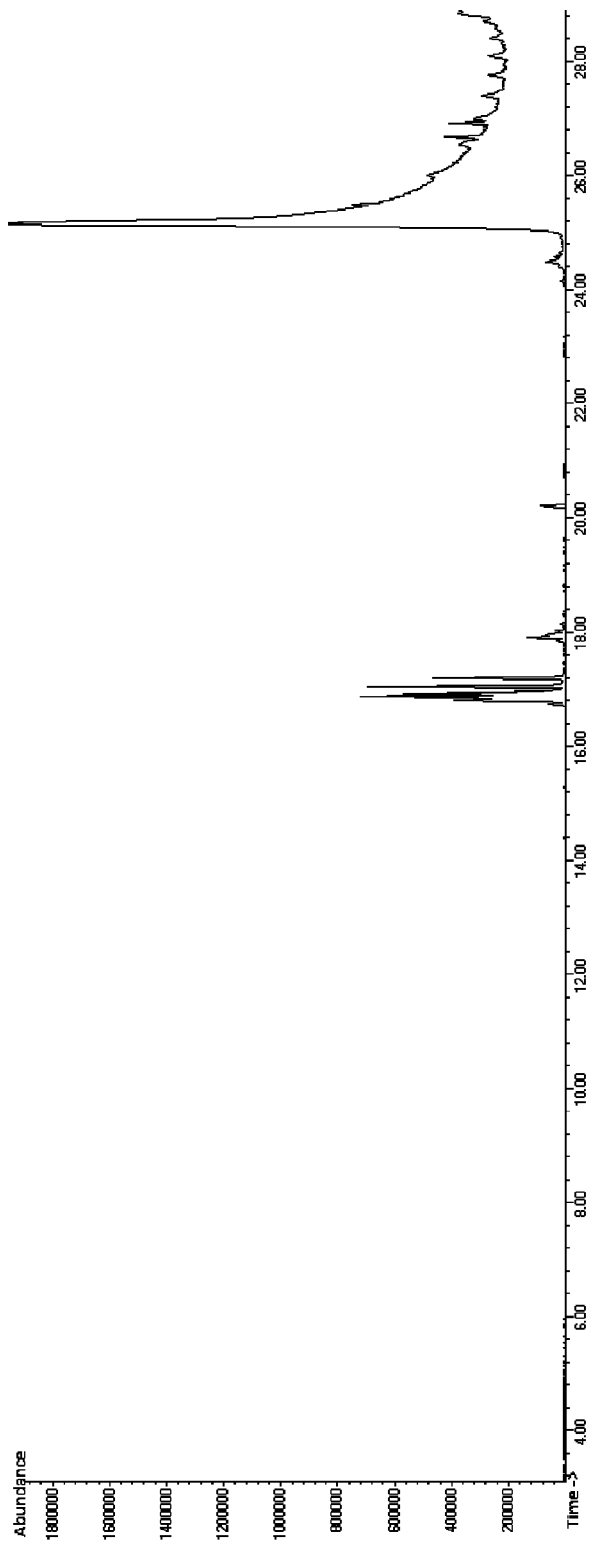
FIG. 37 is a chromatogram of a gas chromatography-mass spectrometry of 9-cis-octadecenoic acid after the decarboxylation and isomerization process as described in Example 35 as a function of elution time (minutes).

Example 35: The Decarboxylation and Isomerization of 9-Cis-Octadecenoic Acid with Bis(Tricyclohexylphosphine)Isopentenylidene Dichlororuthenium, at 250° C. for 24 Hours This reaction was ran by the same method as Example 10, using 0.0030 g of Bis(tricyclohexylphosphine)isopentenylidene dichlororuthenium, and 2.0640 g of 9-cis-octadecenoic acid. In this instance, the Grubbs catalyst is used as a precursor for the decarboxylation and isomerization reaction and not as a metathesis catalyst. This reaction was run at 250° C. for 24 hours. The GC-MS chromatogram, FIG. 37, shows apparently complete steady state isomerization isomerization and alkene production of ~5%.

Figure 38:
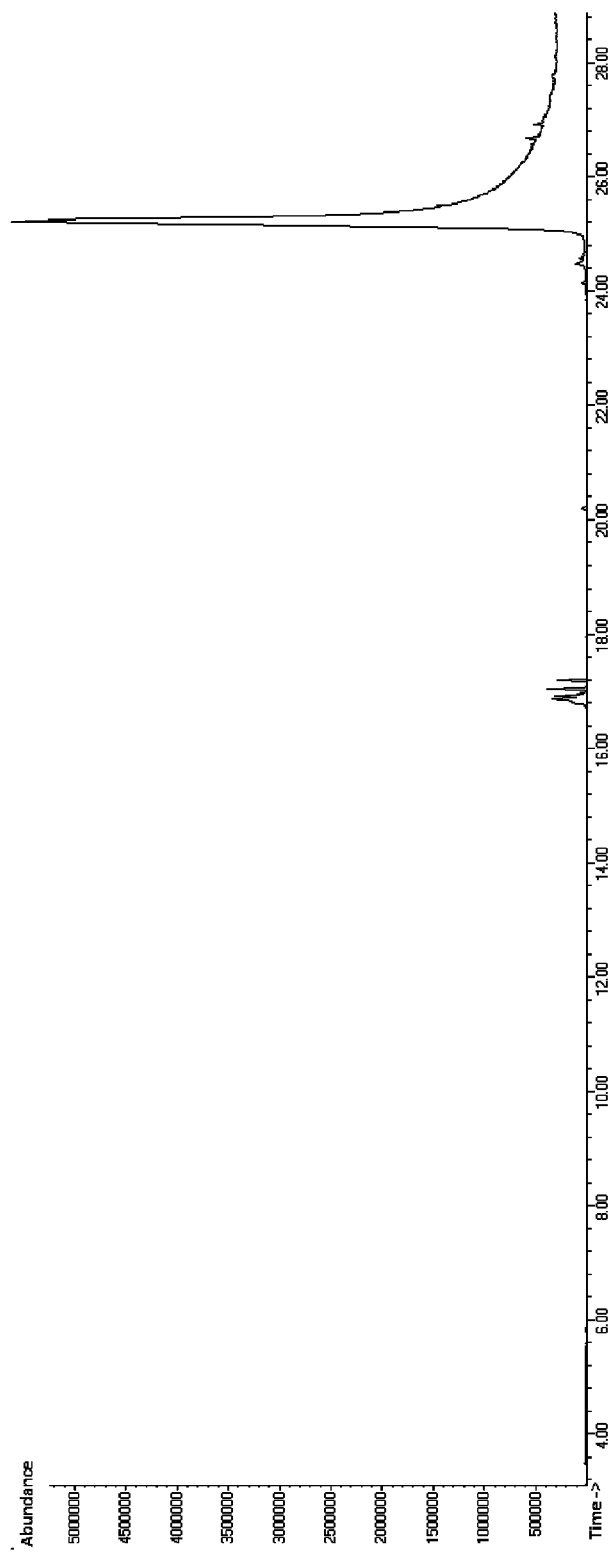
FIG. 38 is a chromatogram of a gas chromatography-mass spectrometry of 9-cis-octadecenoic acid after the decarboxylation and isomerization process as described in Example 36 as a function of elution time (minutes).

Example 36: The Decarboxylation and Isomerization of 9-Cis-Octadecenoic Acid with $RuCl_3$, at 250° C. for 4 Hours This reaction was ran by the same method as Example 10, using 0.0018 g of $RuCl_3$, and 2.0229 g of 9-cis-octadecenoic acid. This reaction was run at 250° C. for 4 hours. The GC-MS chromatogram, FIG. 38, shows apparently complete steady state isomerization and alkene production of ~1%.

Figure 39:
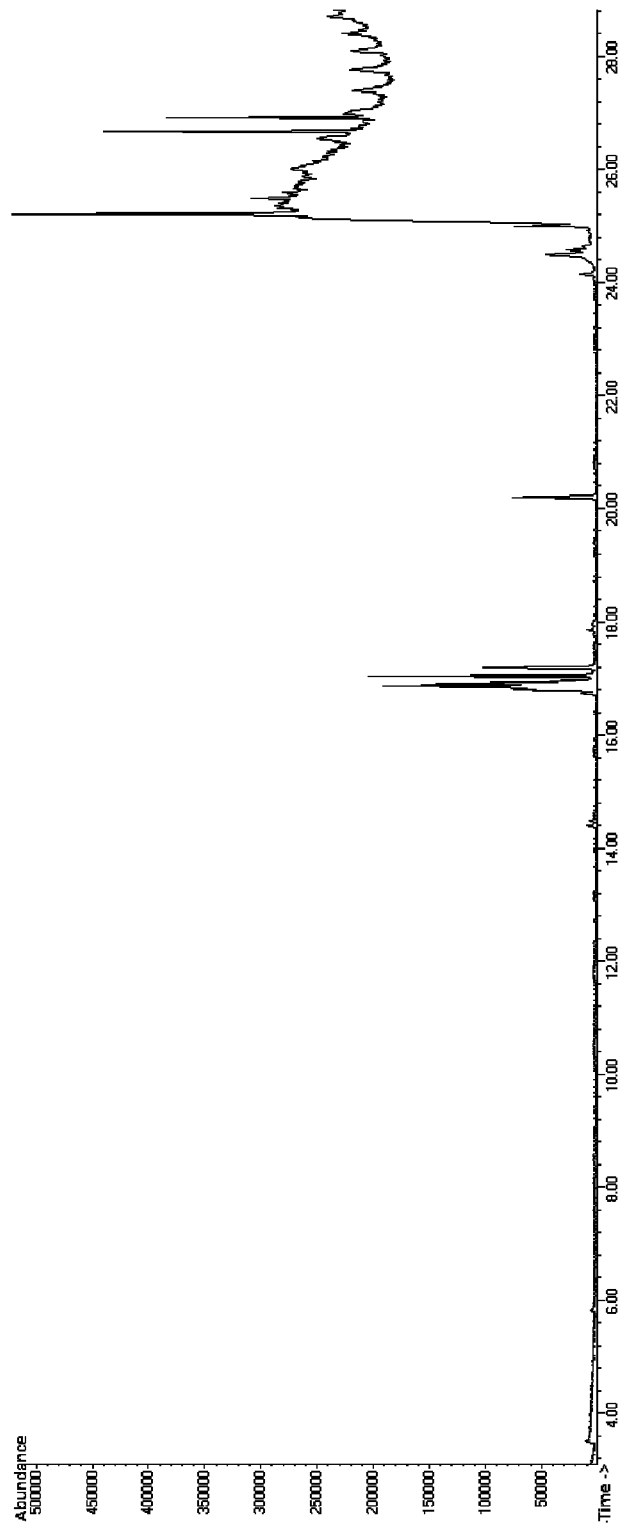
FIG. 39 is a chromatogram of a gas chromatography-mass spectrometry of 9-cis-octadecenoic acid after the decarboxylation and isomerization process as described in Example 37 as a function of elution time (minutes).

Example 37: The Decarboxylation and Isomerization of 9-Cis-Octadecenoic Acid with $RuCl_3$, at 250° C. for 24 Hours This reaction was ran by the same method as Example 10, using 0.0027 g of $RuCl_3$, and 2.0139 g of 9-cis-octadecenoic acid. This reaction was run at 250° C. for 24 hours. The GC-MS chromatogram, FIG. 39, shows apparently complete steady state isomerization and alkene production of ~3%.

Example 37a Control Experiment

Figure 40:
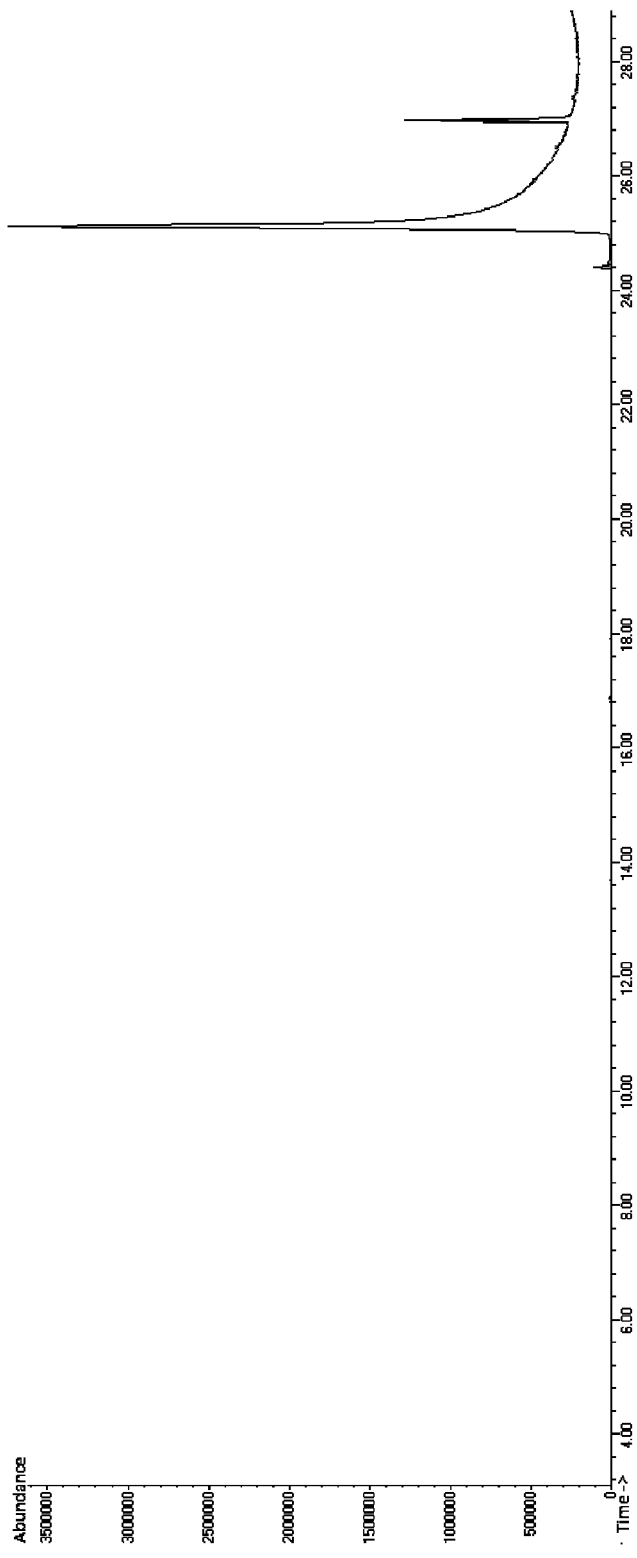
FIG. 40 is a chromatogram of a gas chromatography-mass spectrometry of 9-cis-octadecenoic acid control as described in Example 37A as a function of elution time (minutes).

The Decarboxylation and Isomerization of 9-Cis-Octadecenoic Acid without Catalyst, at 250° C. for 24 Hours This reaction was run by the same method as Example 10. Using 2.0816 g of 9-cis-octadecenoic acid, but no catalysis. GC-MS chromatogram, FIG. 40, shows no significant alkene production.

Figure 41:
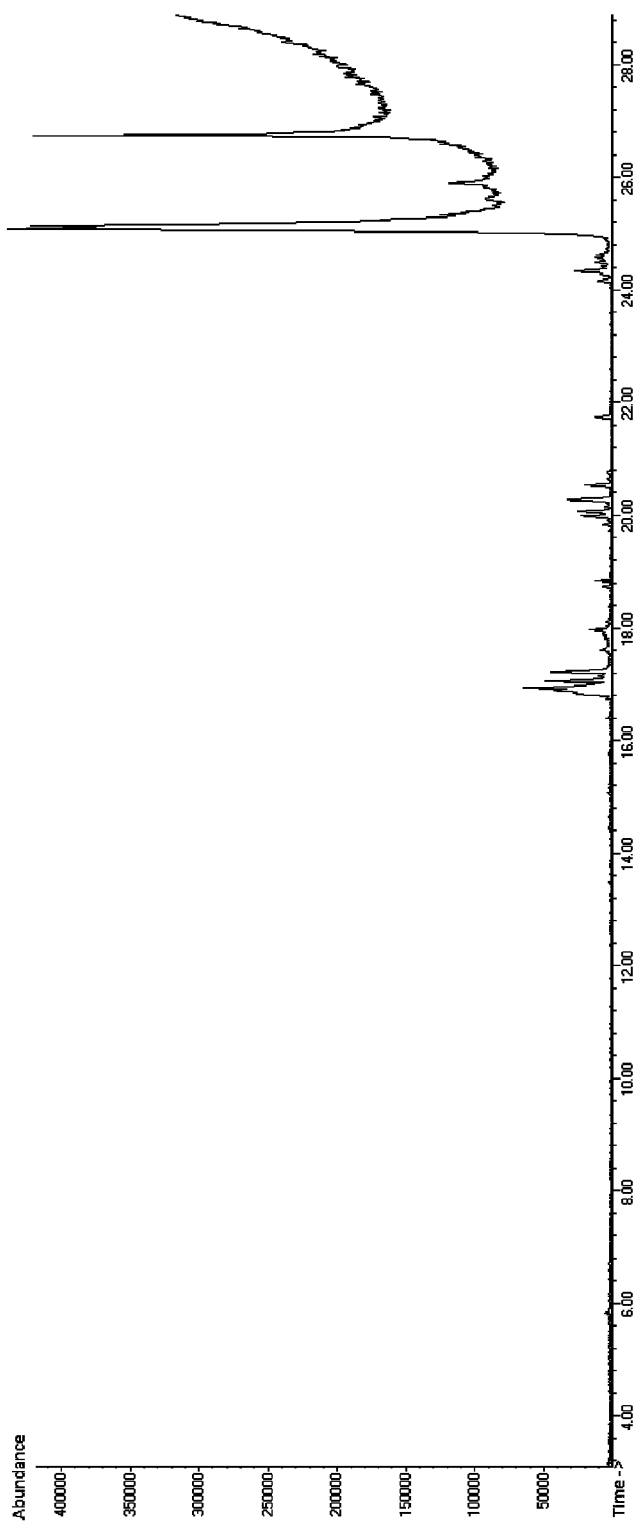
FIG. 41 is a chromatogram of a gas chromatography-mass spectrometry of R-12-hydroxy-9-cis-octadecenoic acid after the decarboxylation and isomerization process as described in Example 38 as a function of elution time (minutes).
Figure 42:
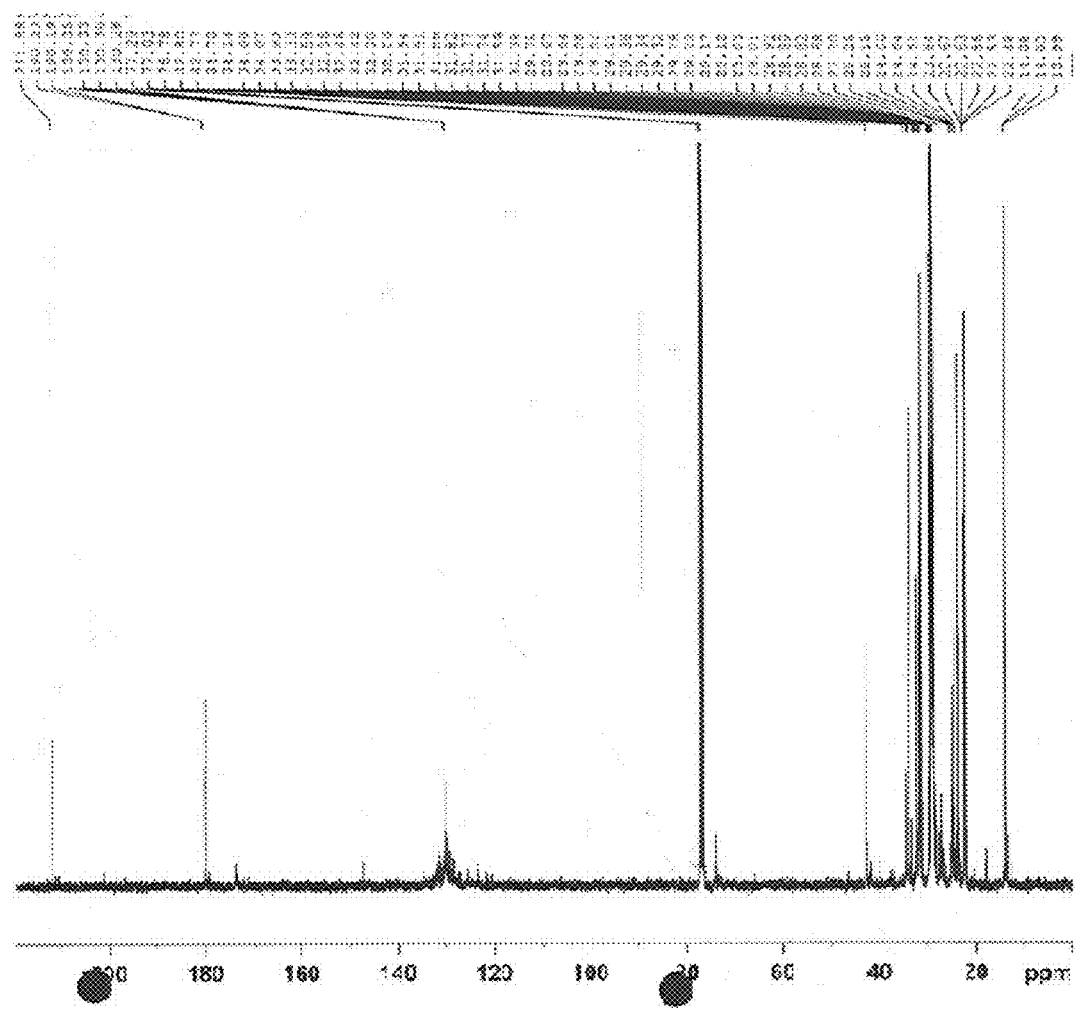
FIG. 42 is a $^{13}$C NMR spectra of the reaction as described in Example 38.

Example 38: The Transformation of R-12-Hydroxy-9-Cis-Octadecenoic Acid with $Ru_3(CO)_{12}$ at 250° C. for 4 Hours Inside of the inert atmosphere dry-box, a saturated solution of $Ru_3(CO)_{12}$ was made by adding 0.0198 g of $Ru_3(CO)_{12}$ to 10.0157 g R-12-hydroxy-9-cis-octadecenoic acid. This was heated to 100° C. with stirring for 90 minutes. Excess $Ru_3(CO)_{12}$ was observed in the yellow solution. A 1.1386 g aliquot was removed, placed in a septa-capped culture tube, and was heated according to the method of Example 10, for 4 hours. The resultant GC-MS chromatogram, FIG. 41 and $^{13}C$ NMR, FIG. 42, show a variety of products, including the described ketone.

Figure 43:
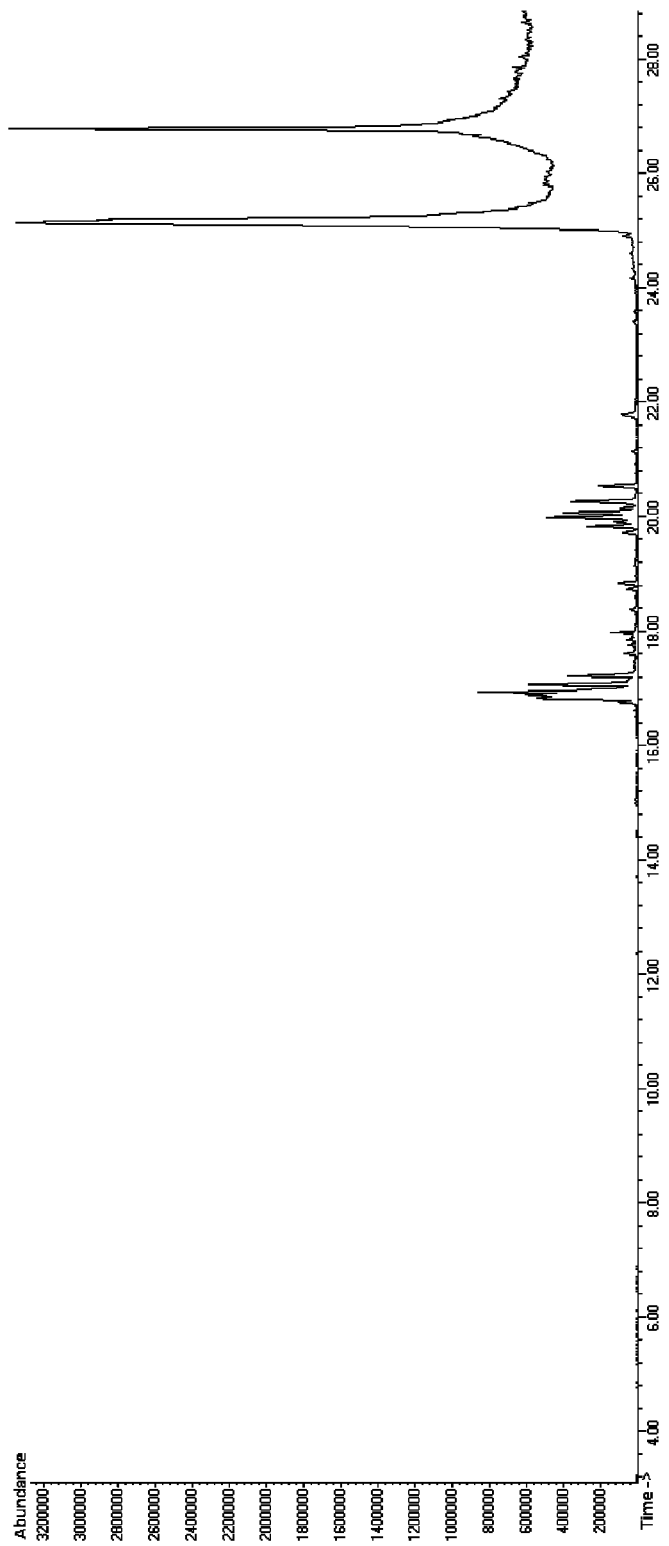
FIG. 43 is a chromatogram of a gas chromatography-mass spectrometry of R-12-hydroxy-9-cis-octadecenoic acid after the decarboxylation and isomerization process as described in Example 39 as a function of elution time (minutes).
Figure 44:
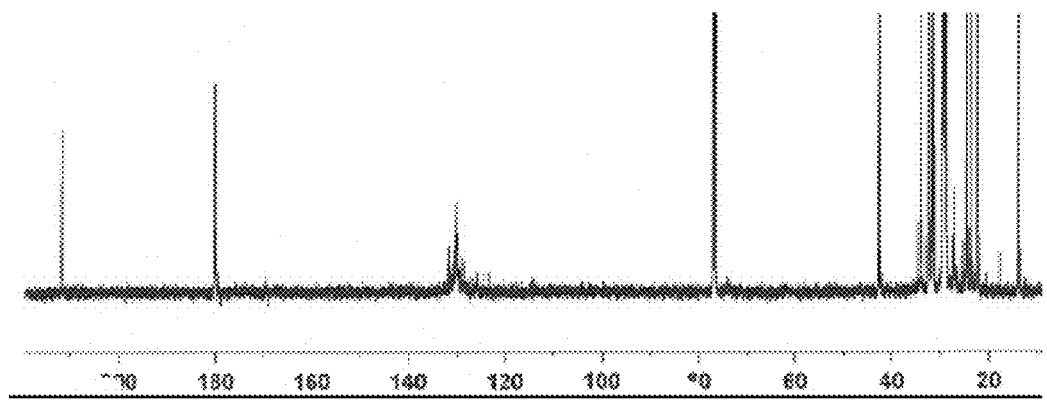
FIG. 44 is a $^{13}$C NMR spectra of the reaction as described in Example 39.

Example 39: The Transformation of R-12-Hydroxy-9-Cis-Octadecenoic Acid with $Ru_3(CO)_{12}$ at 250° C. for 24 Hours This reaction was performed by the method of Example 38. A mass of 1.0380 g of the saturated solution was heated for 24 hours. As before, the GC-MS, shows multiple products, FIG. 43 and the $^{13}C$ NMR spectrum, FIG. 44, confirms a ketone is observed.

Figure 45:
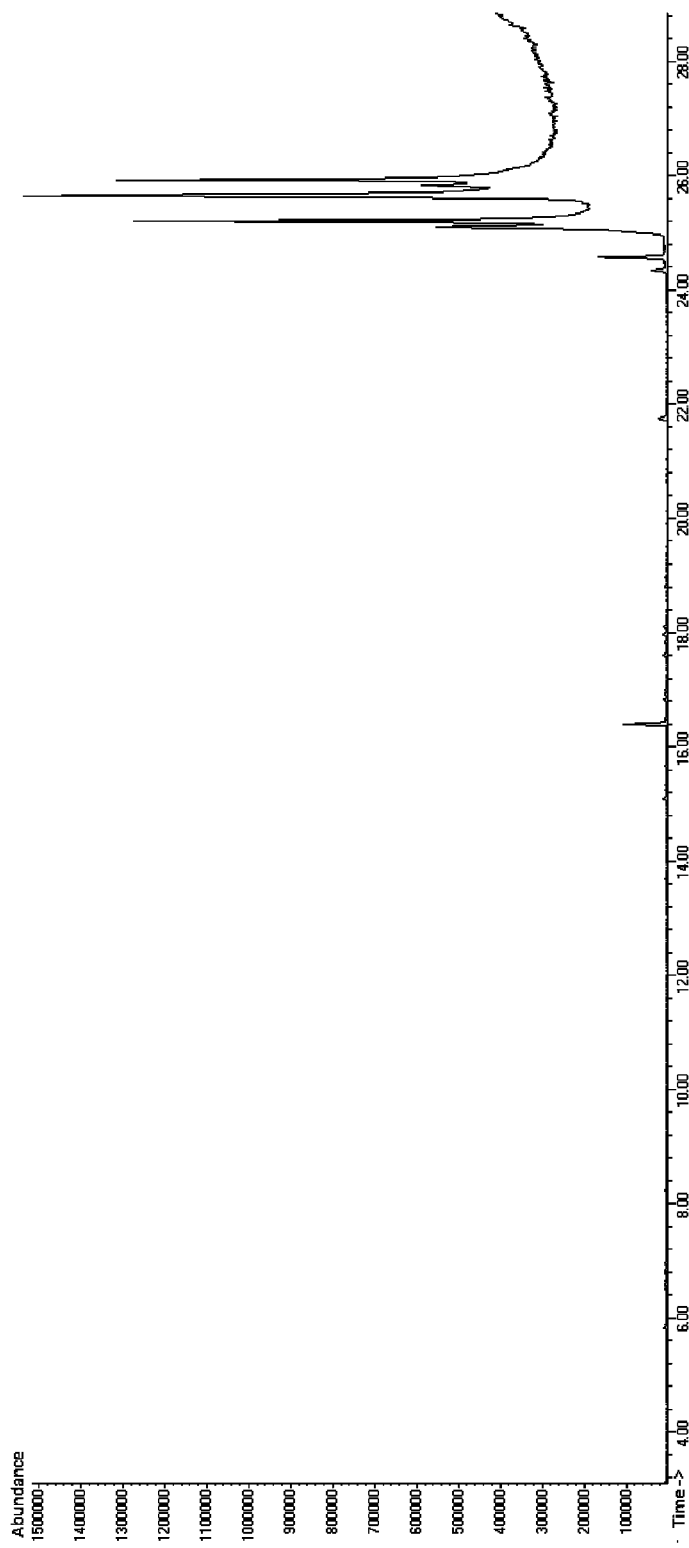
FIG. 45 is a chromatogram of a gas chromatography-mass spectrometry of R-12-hydroxy-9-cis-octadecenoic acid control as described in Example 39A as a function of elution time (minutes).
Figure 46:
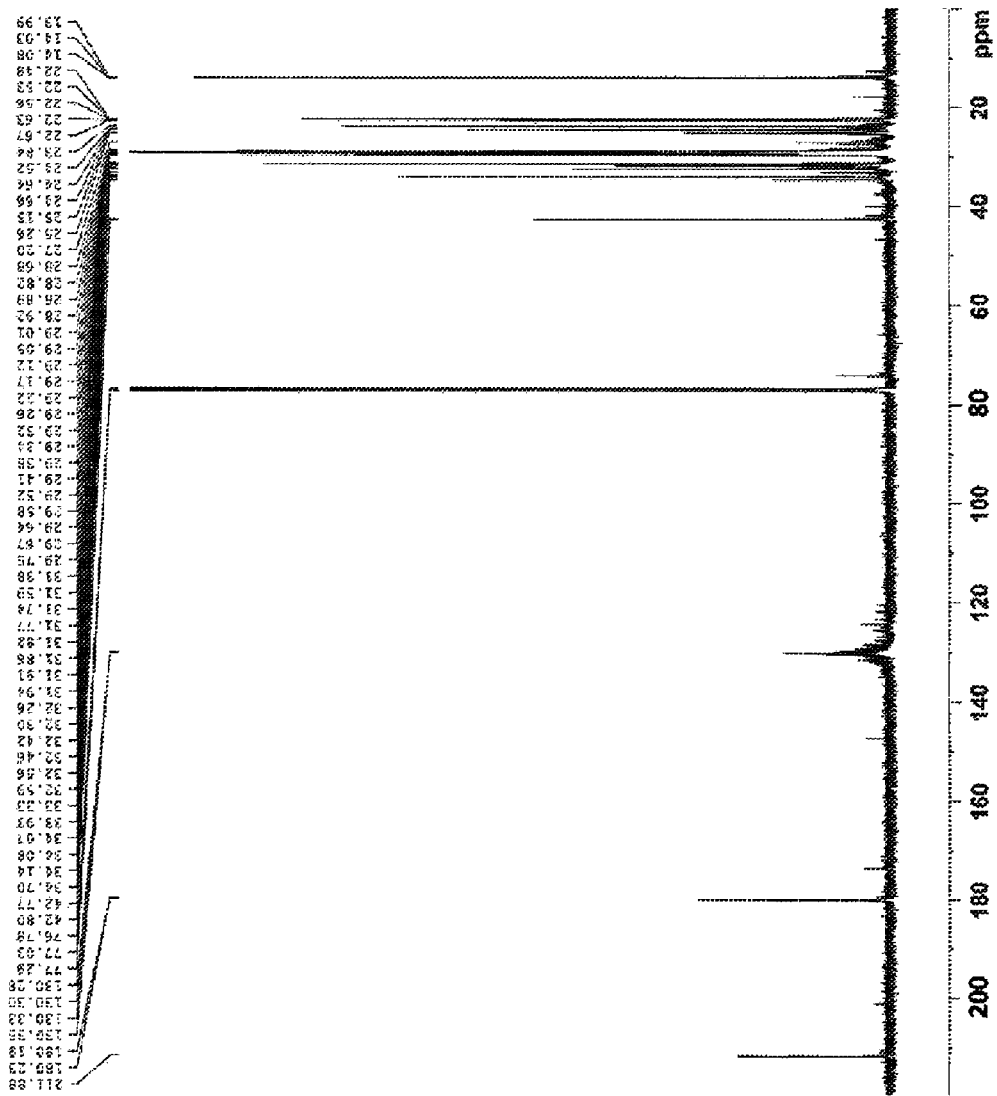
FIG. 46 is a $^{13}$C NMR spectra of the control reaction as described in Example 39A.

Example 39a Control Experiment: The Transformation of R-12-Hydroxy-9-Cis-Octadecenoic Acid without Catalyst at 250° C. for 24 Hours A 1.0224 g sample of R-12-hydroxy-9-cis-octadecenoic acid was heated to 250° C., by the method of Example 38. Although the GC-MS chromatogram shows multiple products, FIG. 45, the absence of ketone is confirmed by NMR spectroscopy, FIG. 46.

Figure 47:
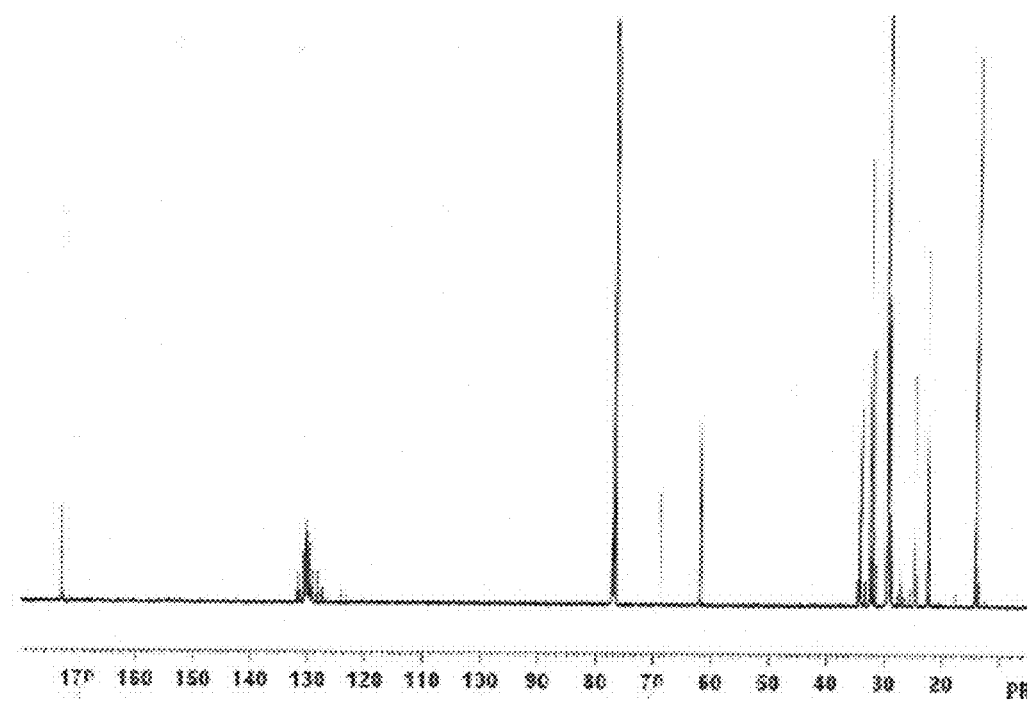
FIG. 47 is a $^{13}$C NMR spectra of triolein after the isomerization process as described in Example 40.
Figure 48:
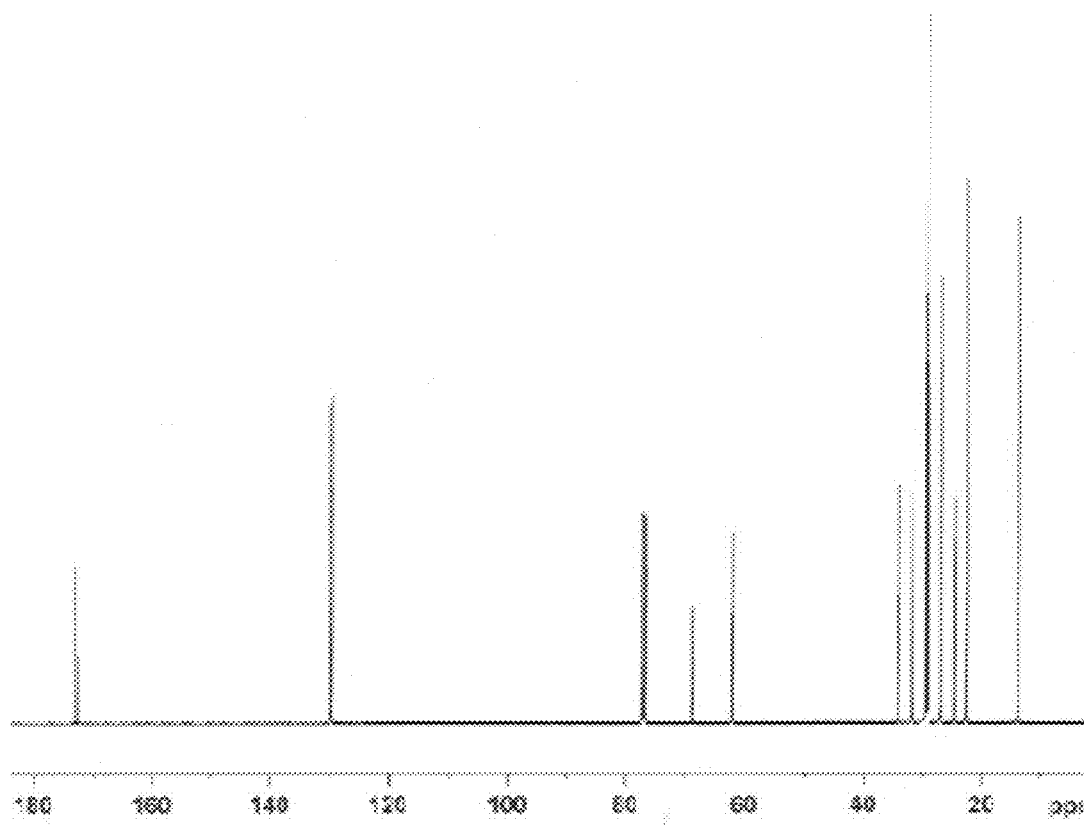
FIG. 48 is a $^{13}$C NMR spectra of the starting material as described in Example 40.

Example 40: Isomerization of Triolein with $[Ru(CO)_2(EtCO_2)]_n$ in 4 Hours This reaction was ran by the same method as Example 10, using 0.0026 g of $[Ru(CO)_2(EtCO_2)]_n$ and 1.9896 g of triolein. This reaction was run at 250° C. for 4 hours. The $^{13}C$ NMR spectrum of the product, FIG. 47, shows isomerization of the product, when compared to the spectrum of the starting material, FIG. 48.

Figure 49:
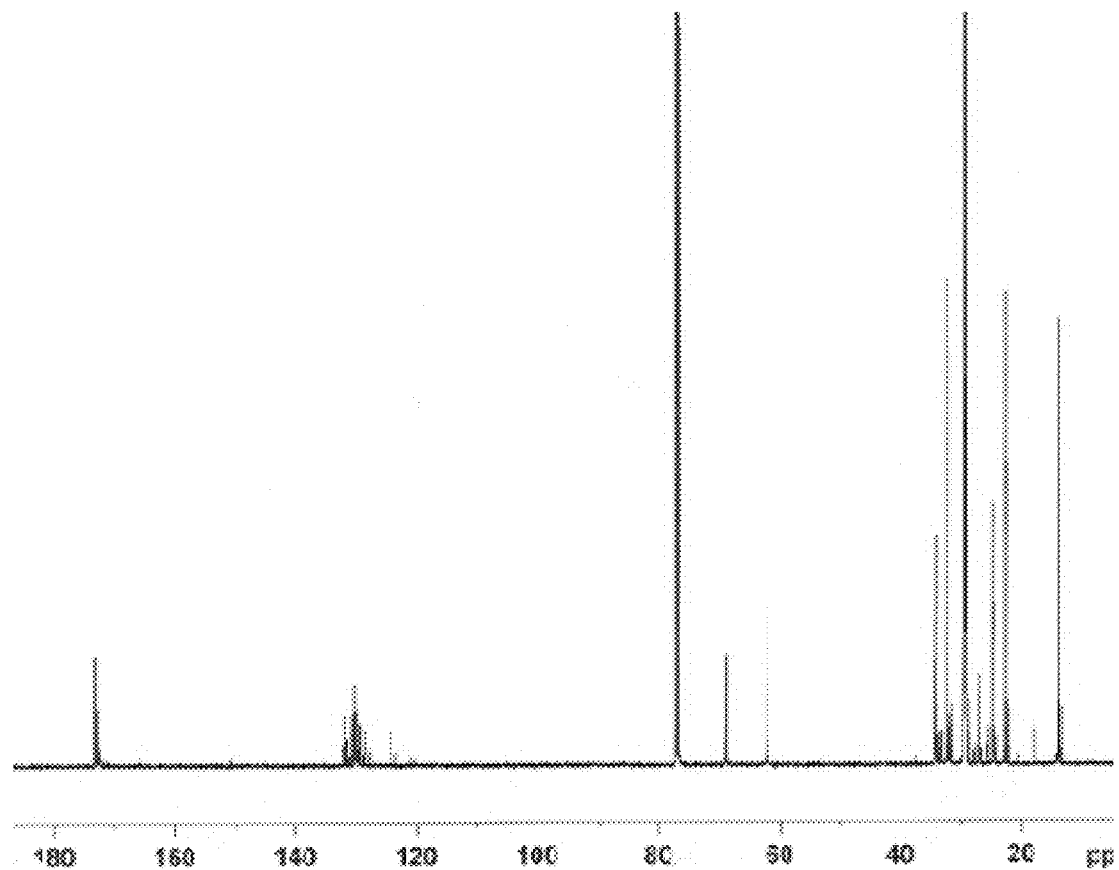
FIG. 49 is a $^{13}$C NMR spectra of triolein after the isomerization process as described in Example 41.

Example 41: Isomerization of Triolein with $[Ru(CO)_2(EtCO_2)]_n$ in 24 Hours This reaction was ran by the same method as Example 10, using 0.0026 g of $[Ru(CO)_2(EtCO_2)]_n$ and 2.0436 g of triolein. This reaction was run at 250° C. for 24 hours. The $C^{13}$ NMR spectrum of the product, FIG. 49, shows apparently complete steady state isomerization.

Figure 50:
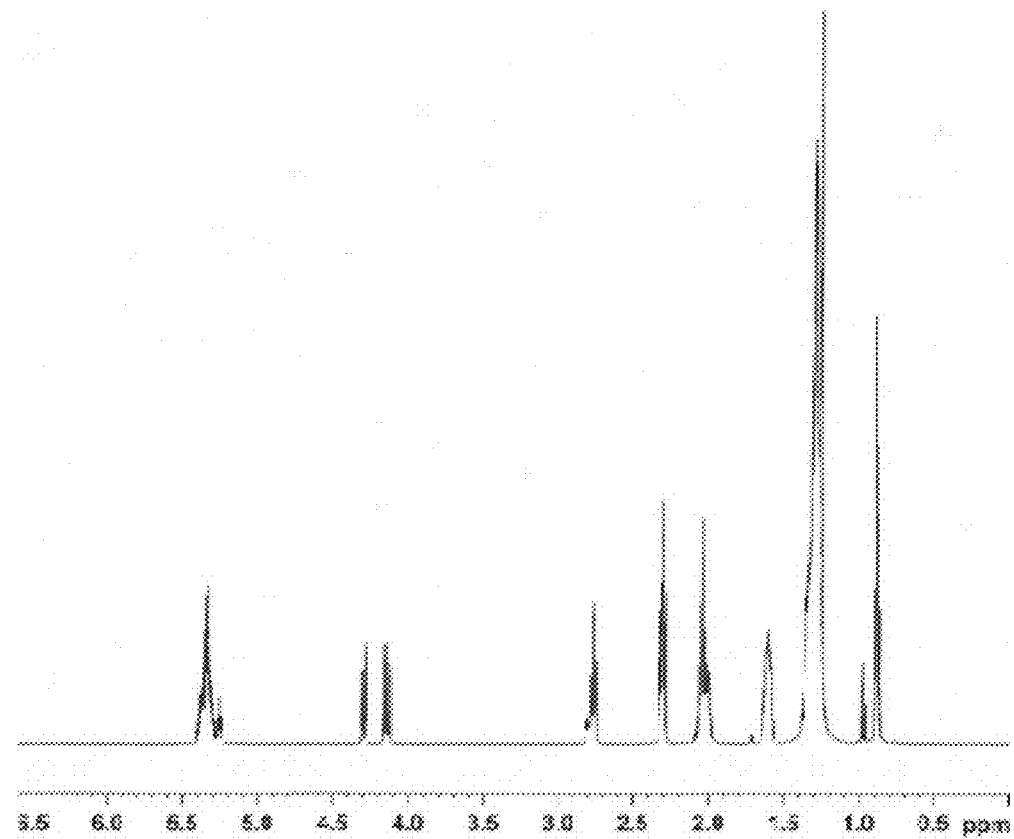
FIG. 50 is a $^{1}$H NMR spectra of isomerized product after the process as described in Example 42.
Figure 51:
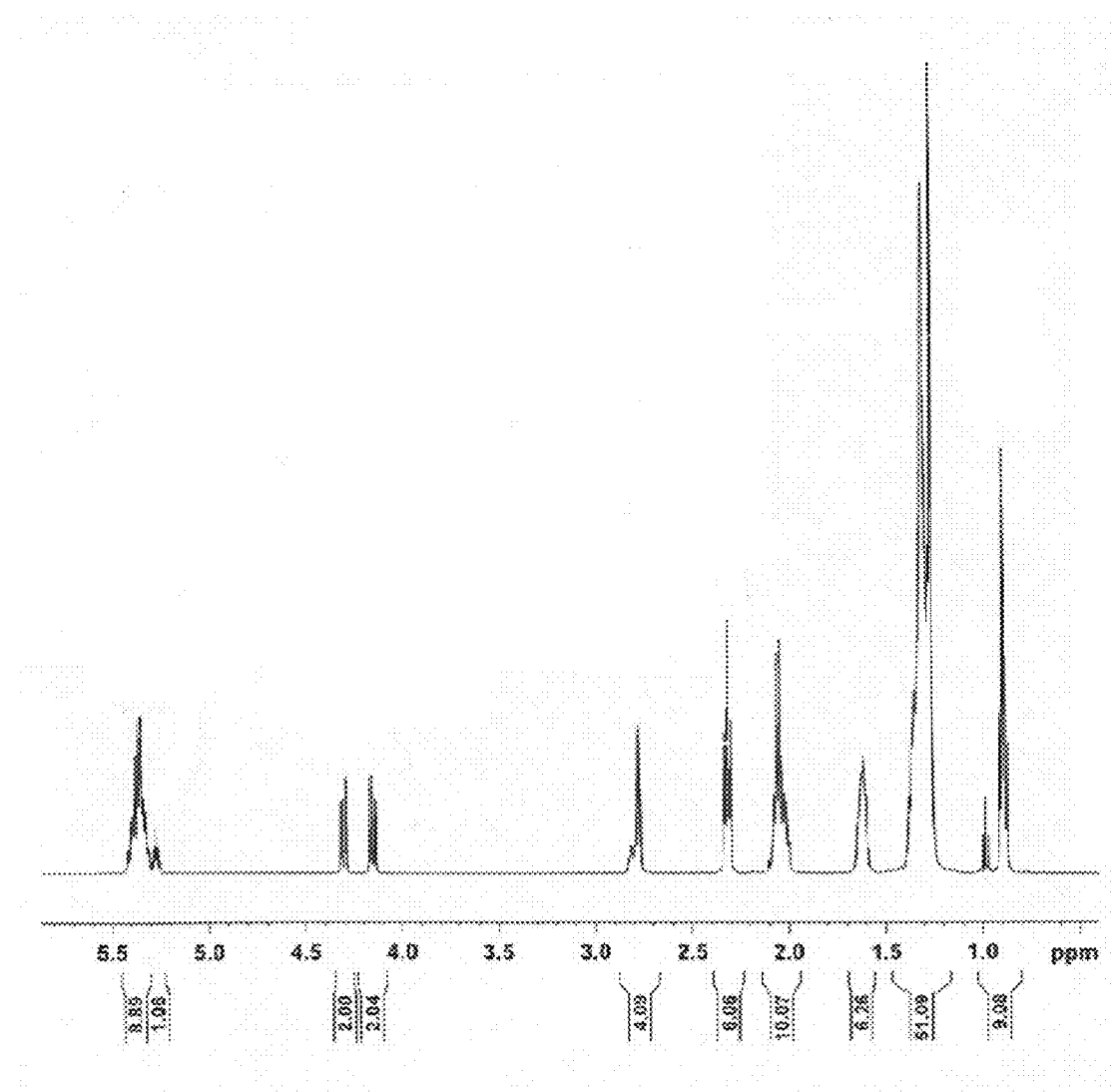
FIG. 51 is a $^{1}$H NMR spectra of isomerized product of the starting material for the process as described in Example 42.

Example 42: Isomerization of Soybean Oil with $[Ru(CO)_2(EtCO_2)]_n$ in 24 Hours A stock solution of 15.0236 g of soybean oil with 0.0063 g of $[Ru(CO)_2(EtCO_2)]_n$ was prepared in an inert atmosphere glovebox as in the method of Example 38. This reaction was run by the same method as Example 10, using 1.9632 g of soybean oil, at 125° C. for 24 hours. The $^1H$ NMR spectrum of the product, FIG. 50, is similar to the spectrum of the starting material, FIG. 51.

Figure 52:
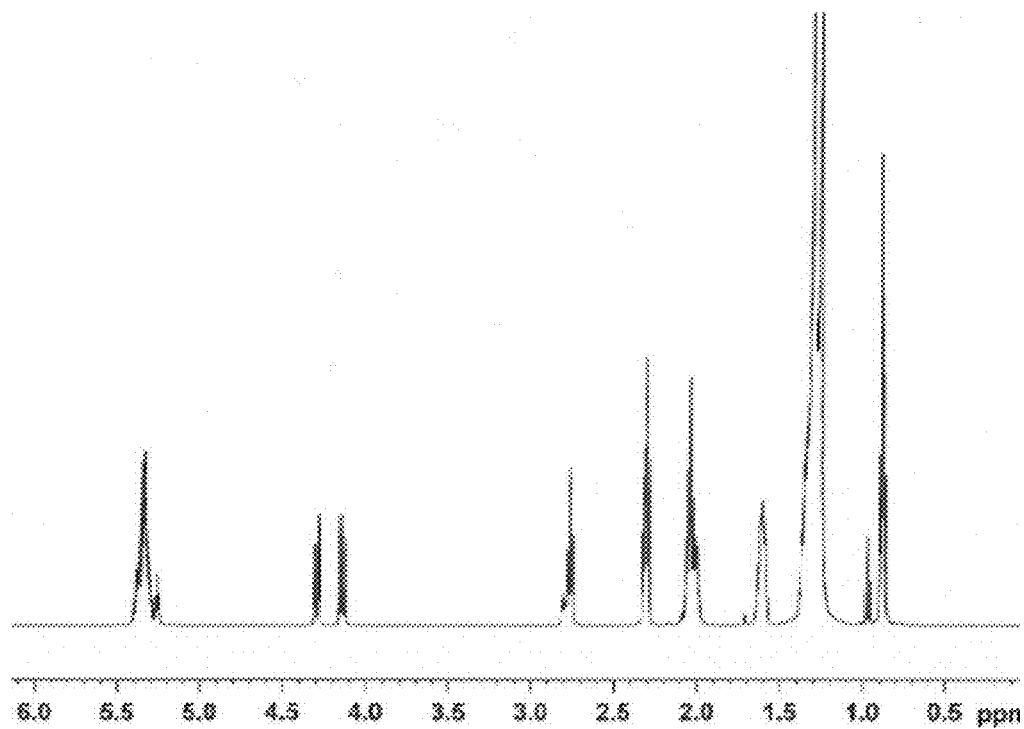
FIG. 52 is a $^1$H NMR spectra of material after the process as described in Example 42A.

Example 42a Control Experiment Isomerization of Soybean Oil without the Presence of Ruthenium This reaction was run by the same method as Example 10, with 2.1463 g of soybean oil, without catalyst precursor. This reaction was run at 125° C. for 24 hours. The $^1H$ NMR spectrum of the product, FIG. 52, shows very little isomerization of the product, when compared to the spectrum of the starting material, FIG. 51.

Figure 53:
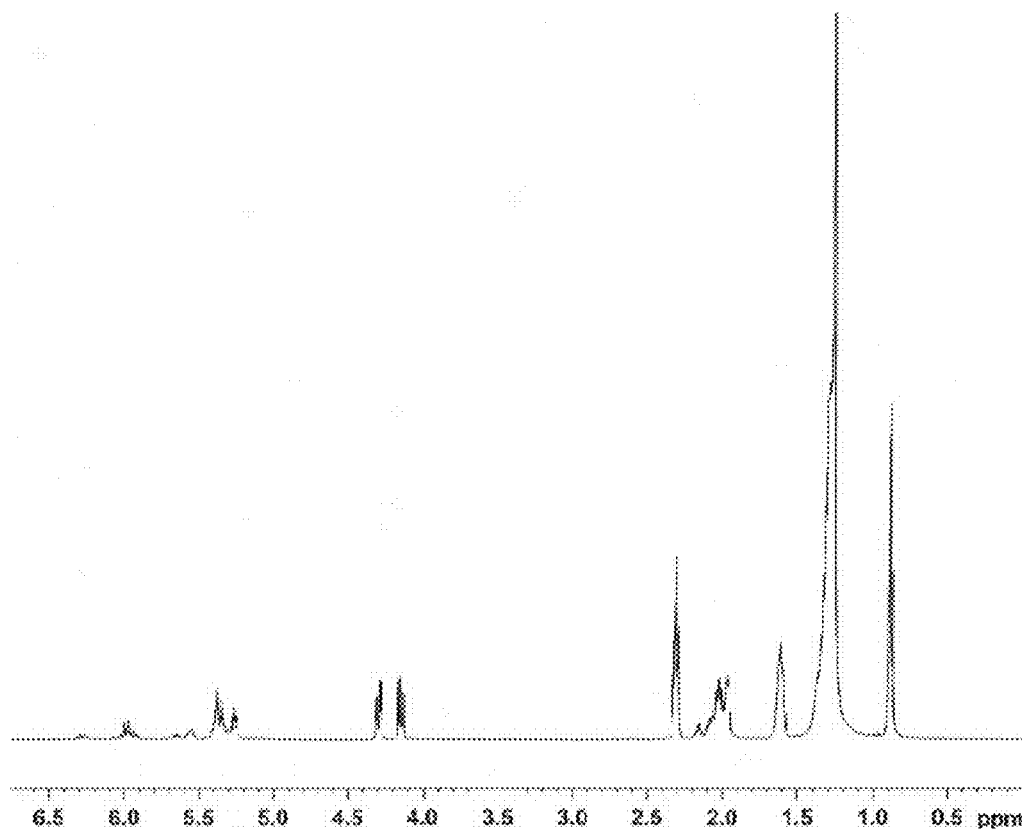
FIG. 53 is a $^1$H NMR spectra of isomerized product after the process as described in Example 43.

Example 43: Isomerization of Soybean Oil with $[Ru(CO)_2(EtCO_2)]_n$ in 24 Hours This reaction was ran by the same method as Example 42, using 2.0137 g of soybean oil solution with $[Ru(CO)_2(EtCO_2)]_n$. This reaction was run at 175° C. for 24 hours. The $^1H$ NMR spectrum of the product, FIG. 53, shows isomerization of the product, when compared to the spectrum of the starting material, FIG. 51.

Figure 54:
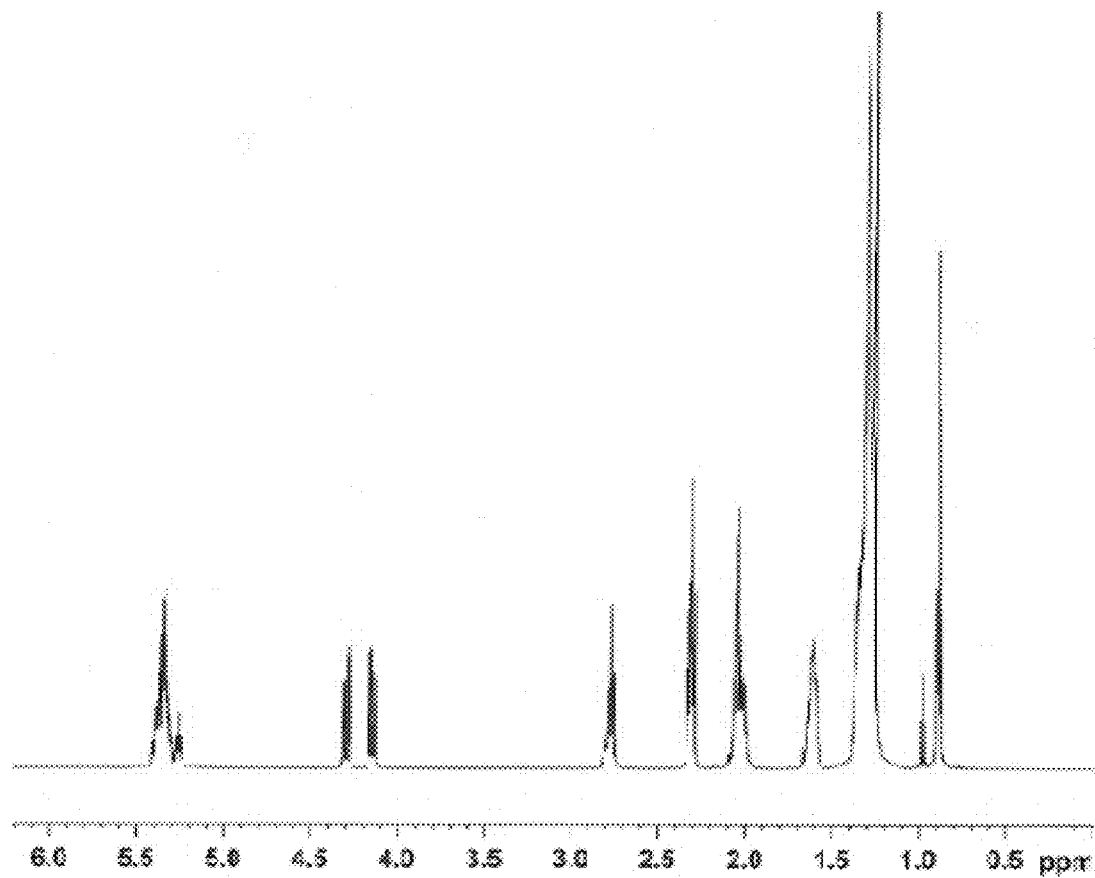
FIG. 54 is a $^1$H NMR spectra of material after the process as described in Example 43A.

Example 43a Control Experiment: Isomerization of Soybean Oil without the Presence of Ruthenium This reaction was run by the same method as Example 10, with 1.9989 g of soybean oil, without catalyst precursor. This reaction was run at 175° C. for 24 hours. The $^1H$ NMR spectrum of the product, FIG. 54, shows very little isomerization of the product, when compared to the spectrum of the starting material, FIG. 51.

Figure 55:
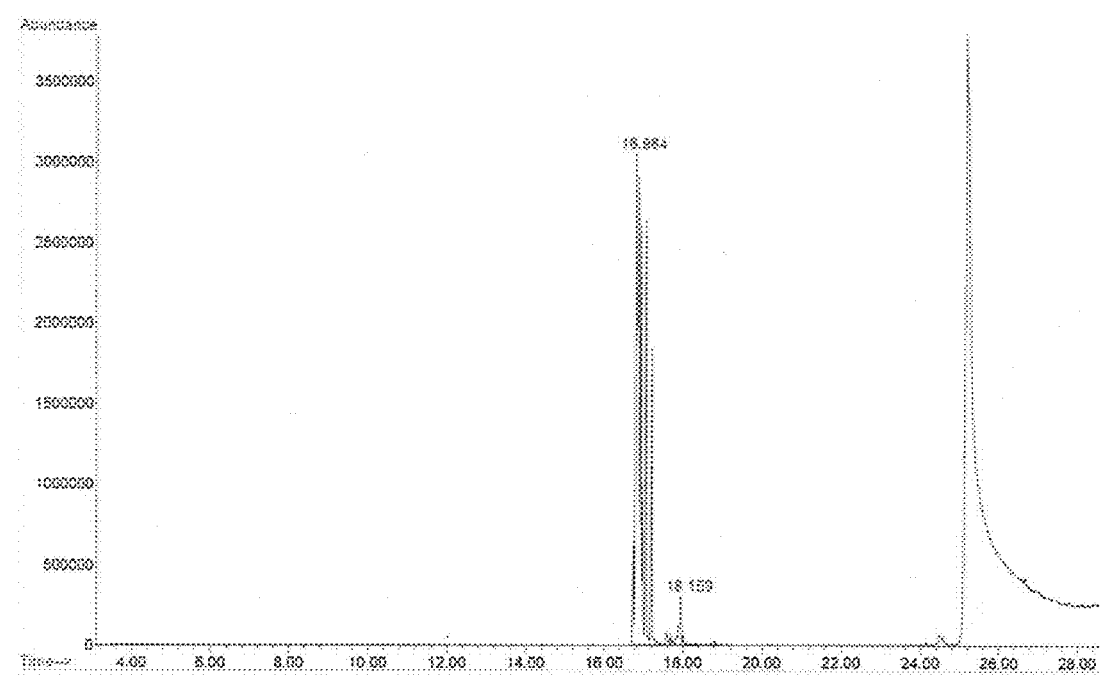
FIG. 55 is a chromatogram of a gas chromatography-mass spectrometry of 9-cis-octadecenoic acid after the decarboxylation and isomerization process as described in Example 44 as a function of elution time (minutes).

Example 44: The Decarboxylation and Isomerization of 9-Cis-Octadecenoic Acid with a Mixture of $Os_3(CO)_{12}$ and $Ru_3(CO)_{12}$, at 250° C. for 4 Hours This reaction was ran by the same method as Example 10, using 0.0017 g of $Ru_3(CO)_{12n}$, 0.0011 g $Os_3(CO)_{12}$, and 2.0436 g of 9-cis-octadecenoic acid. This reaction was run at 250° C. for 4 hours. The GC-MS chromatogram, FIG. 55, shows alkene production of nearly 30%.

Figure 56:
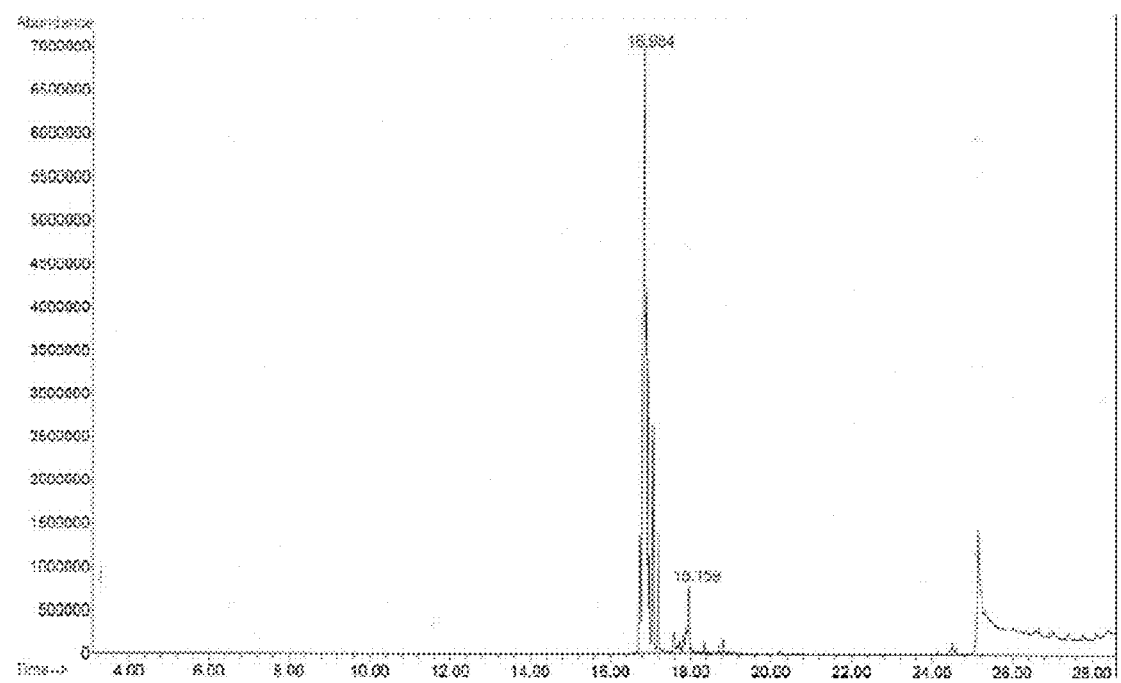
FIG. 56 is a chromatogram of a gas chromatography-mass spectrometry of 9-cis-octadecenoic acid after the decarboxylation and isomerization process as described in Example 56 as a function of elution time (minutes).

Example 45: The Decarboxylation and Isomerization of 9-Cis-Octadecenoic Acid with a Mixture of $Os_3(CO)_{12}$ and $Ru_3(CO)_{12}$, at 250° C. for 24 Hours This reaction was ran by the same method as Example 10, using 0.0017 g of $Ru_3(CO)_{12n}$, 0.0011 g of $Os_3(CO)_{12}$, and 2.0436 g of 9-cis-octadecenoic acid. This reaction was run at 250° C. for 24 hours. The GC-MS chromatogram, FIG. 56, shows alkene production of nearly 80%.

Example 46: Larger Scale Isomerization and Decarboxylation of Oleic Acid

Inside an inter atmosphere dry-box, 0.501 g (0.00078 mol) of $Ru_3(CO)_{12}$ was mixed with 60.1 g (0.21 mol) of 9-cis-octadecenoic acid in a 500 mL roundbottom flask. The mixture was heated to 90° C. for 45 minutes, then a Vigreux column was placed on the flask, which was septa capped, and it was brought out of the glovebox, and connected to a Schlenk line with argon flow. The flask was placed in a fitted heating block on a hotplate which was set to 300° C., corresponding to a reaction temperature of ~280° C. The flask was covered with glass wool and foil, and the refluxing continued for 24 hours, resulting in a dark orange solution. Upon cooling, the crude product was a light yellow solid, which was purified through vacuum distillation. A still head was attached to the roundbottom flask, and connected to a vacuum showing a pressure reading below 0.2 torr. The distillation was monitored and hotplate settings between 150-165° C. gave an overhead temperature recorded between 90-95° C. The final collected product was a clear liquid, (20.9 g, 0.877 mol, 42%). GC analysis showed complete the product to be a mixture of isomers of heptadecene.

Figure 59:
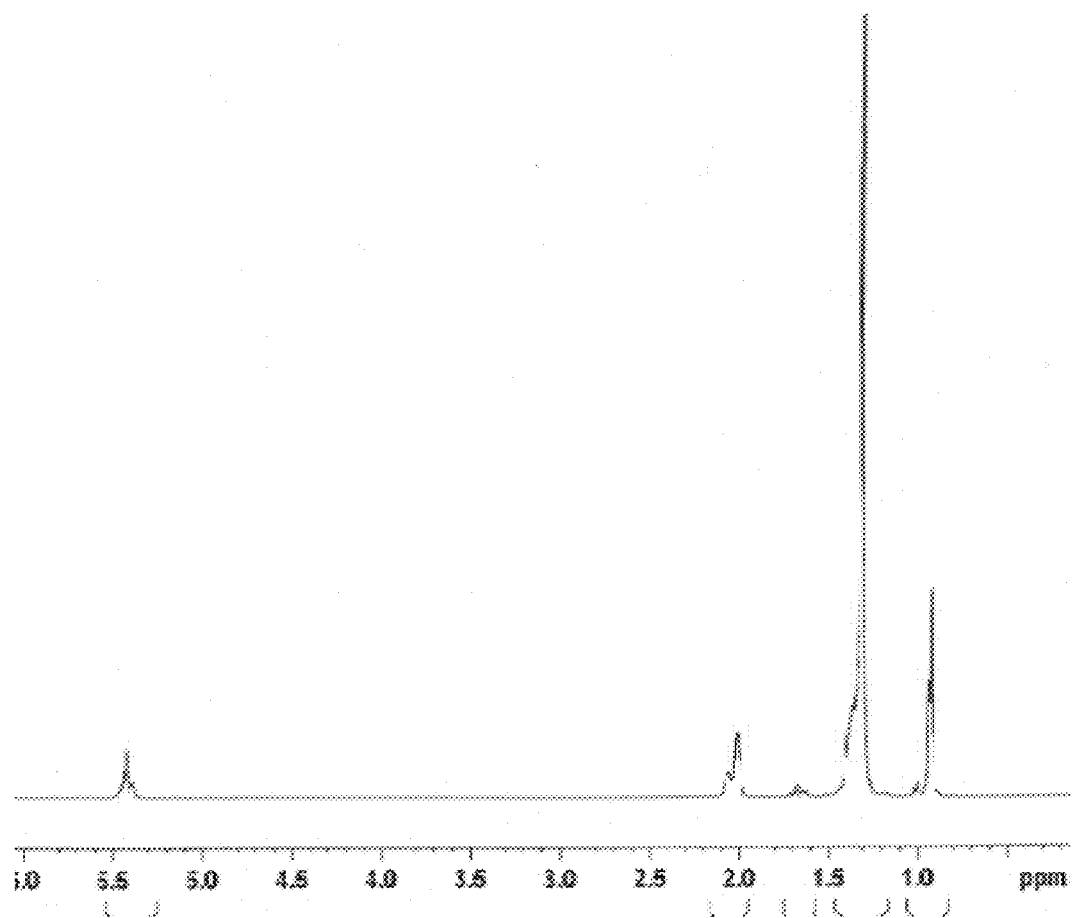
FIG. 59 is a $^1$H NMR spectrum of the isomerized octadecene from Example 10 using the starting material in Example 47.
Figure 60:
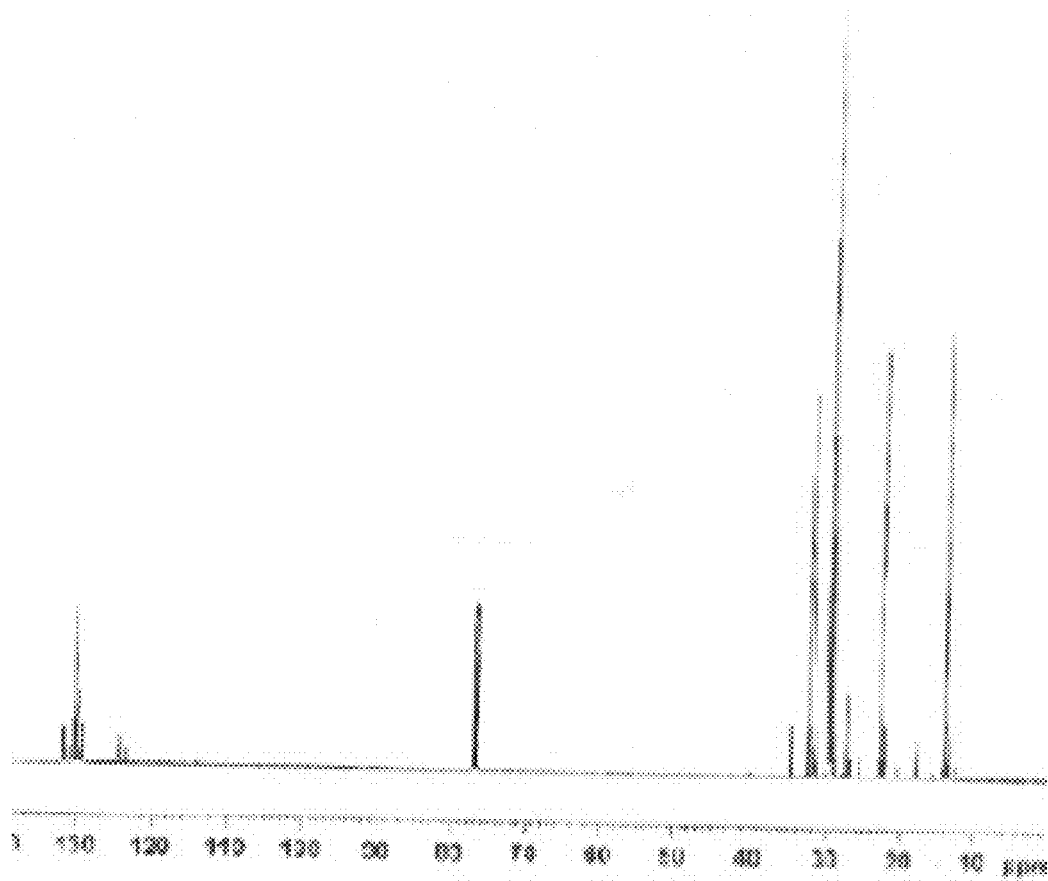
FIG. 60 is a $^{13}$C NMR spectrum of the isomerized octadecene from Example 10, using the starting material in Example 47.
Figure 61:
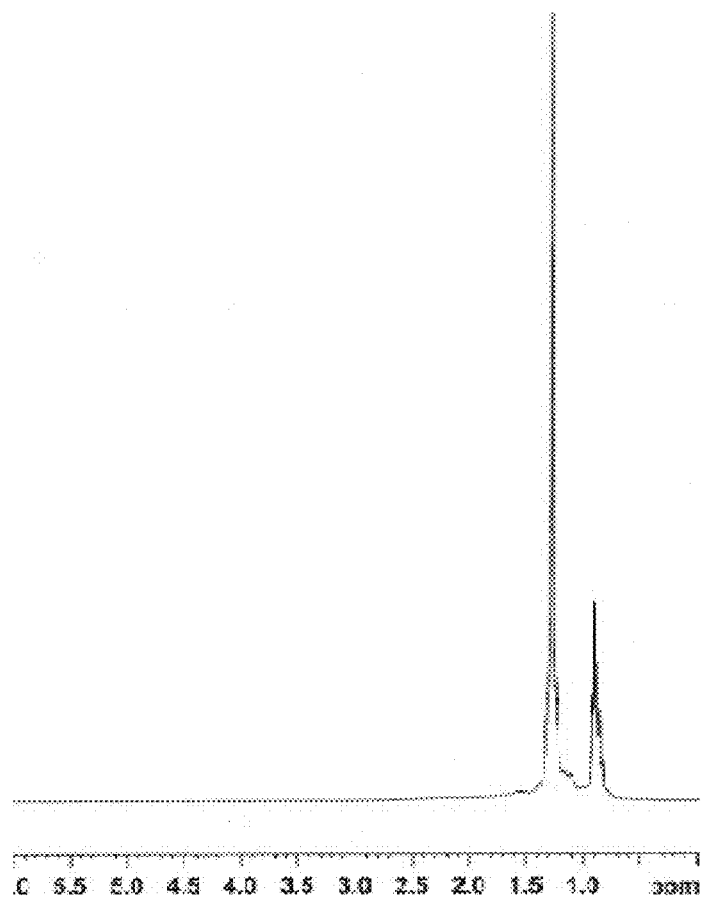
FIG. 61 is a $^1$H NMR spectrum of the polymerized isomerized octadecene of Example 47.
Figure 62:
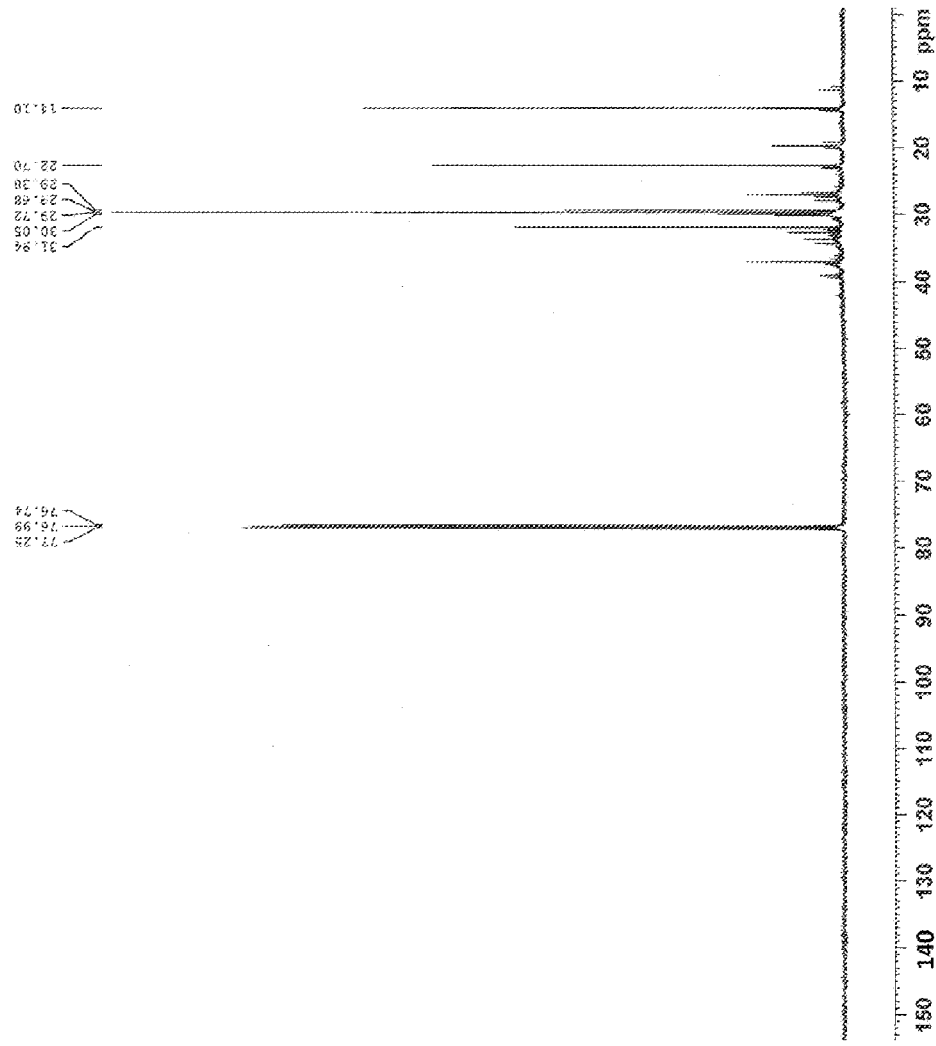
FIG. 62 is a $^{13}$C NMR spectrum of the polymerized isomerized octadecene of Example 47.

Example 47: Polymerization of Isomerized Alkenes Using Hexafluoro Antimonic Acid Oligomerization of a sample of isomerized octadecene, made by the method of Example 11, was carried out in a 50 mL autoclave reactor from Parr Instrument Co. (Moline, Ill.). The reactor was attached to an Isco Model 260D high pressure syringe pump used to fill the reactor with $CO_2$. In the reaction, 10 g of octadecene was added to the reactor, which was then sealed and purged with $N_2$ was for 5 minutes before addition of $CO_2$ to the desired pressure and temperature maintained by a Parr 4843 controller. Once the reactor was brought to the appropriate temperature, 60° C., and pressure of 1200 psi, $HSbF_6$ was charged into an injection port to give a molar ratio of catalyst to alkene of 1:1. A flush of fresh $CO_2$ was pumped through the injector line to insure that the initiator was supplied to the reactor. After reaction of 24 hr, 2 ml of $H_2O$ was added into reactor to quench any remaining initiator. The product was dissolved in 20 mL hexane and washed sequentially with $H_2O$, 5% aqueous sodium bicarbonate, and $H_2O$. The hexane solution was dried over sodium sulfate, filtered, and evaporated under reduced pressure. A comparison of the NMR analysis of the starting material, FIGS. 59 and 60, with that of the product, FIGS. 61 and 62, show the apparently complete reaction of the alkene groups. The analysis results as well as those of gel permeation chromatography show that the dominate constituent of the material is dimeric, with a small amount of trimer but no higher oligomers.

Figure 63:
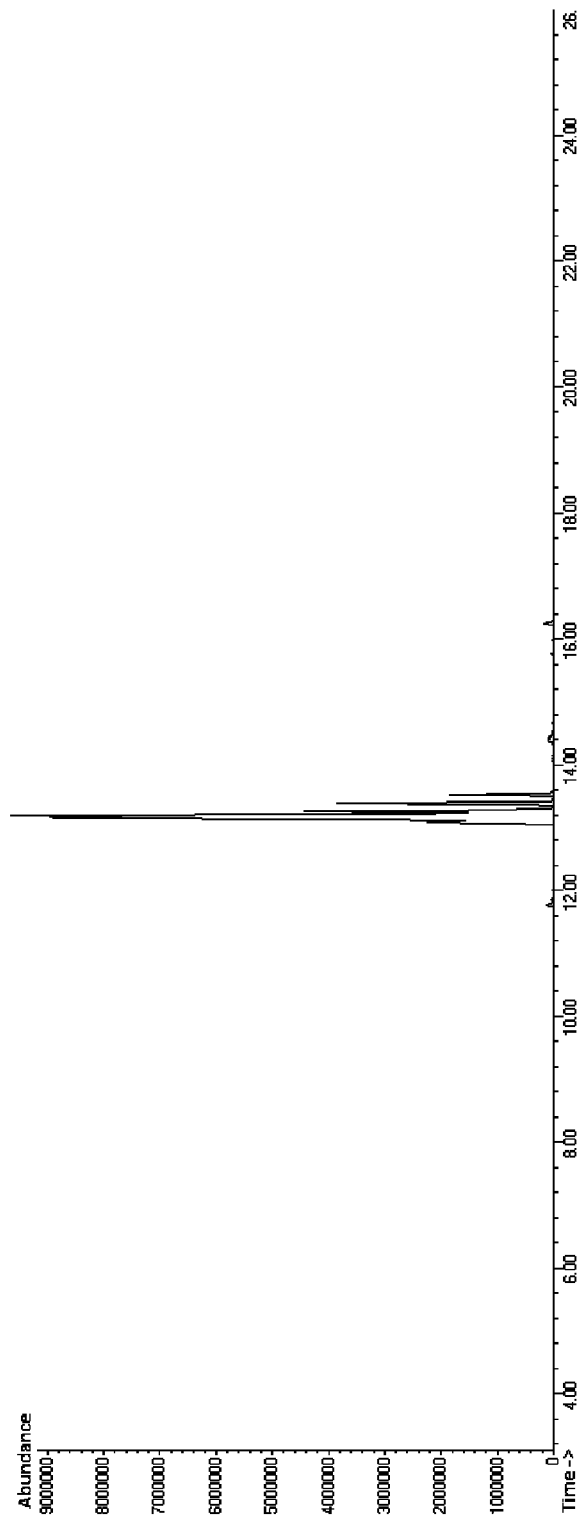
FIG. 63 is a GC-MS chromatogram of isomerized tetradecene showing a mixture of isomers as a function of elution time (minutes).
Figure 64:
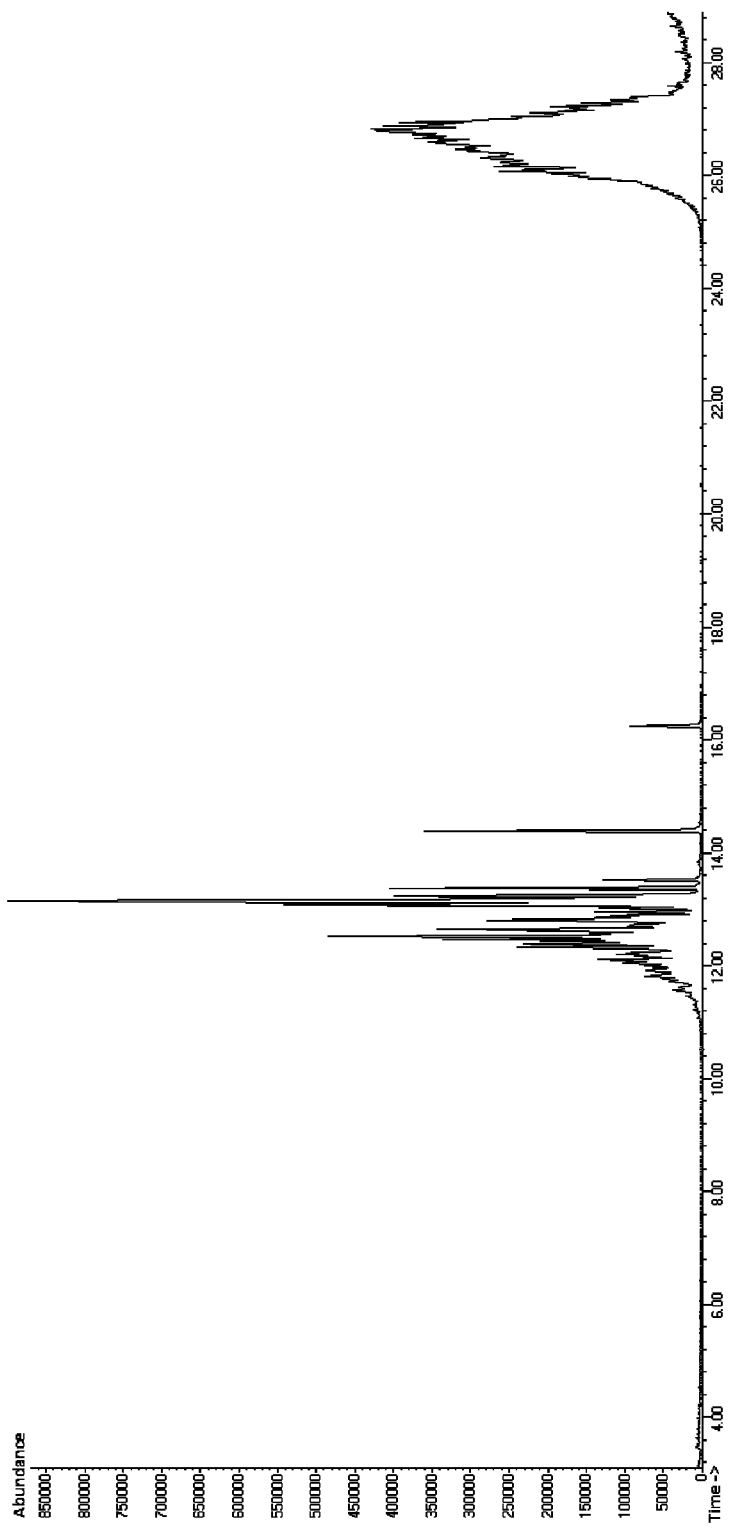
FIG. 64 is a GC-MS chromatogram of polymerized isomerized tetradecene showing conversion to dimeric product as a function of elution time (minutes).
Figure 65:
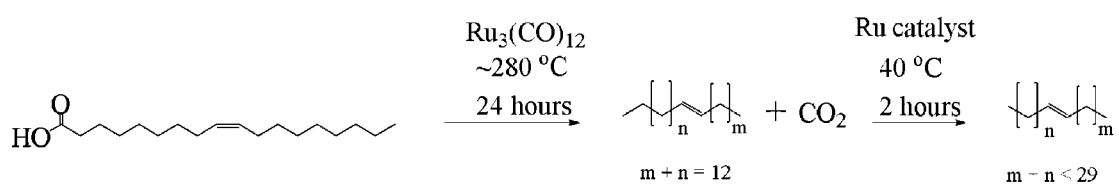
FIG. 65 is a depiction of an exemplar reaction scheme for the decarboxylation reaction followed by the self metathesis reaction to make a plurality of alkene compounds.

Example 48: Isomerization and Polymerization of Isomerized Alkenes Heterogeneous Catalysts Inside of the inert atmosphere dry-box, 0.0015 g $[Ru(CO)_2(EtCO_2)]_n$ was added to 10.0013 g of 7-trans-tetradecene inside a roundbottom flask. It was attached to a Schlenk line and placed in a heating block on a hotplate set to 250° C. for 4 hours. At this point, isomerization was not complete, and additional $[Ru(CO)_2(EtCO_2)]_n$, 0.0018 g, was added, with heat again applied for 4 hours. A GC-MS trace showed an apparent steady state of isomers. This was checked by heating the reaction again and observing that there was no change in isomer distribution. The alkene was dried over 4A and 13× mol sieves for at least 12 hours before performing polymerization reactions. These were also prepared inside of the inert atmosphere dry-box. Isomerized tetradecene, 0.1799 g was placed in 16 mm×150 mm test tube. The catalyst, sulfated zirconia, 0.0176 g, that had been prepared via literature methods, was added. The tube was sealed with a septa cap and attached to a Schlenk line via a needle and placed in a heating block on a hotplate. The polymerization reactions were done at 200 for 4 hours. Comparison of the GC-MS chromatograms of the starting material, FIG. 63, with the product, FIG. 64, show 58% conversion to dimeric material. A comparison of $^1$H NMR spectra shows the alkane/alkene ratio increases from 14.1 to 29.7 in the product.

Example 49: Polymerization of Isomerized Heptadecene Made from Decarboxylation of 9-Cis-Octadecenoic Acid This Example was done by the same method as Example 48, except isomerized heptadecene from Example 46 was used. It was ran through an Amberlite IRA 400 column and distilled 3 times prior to use. Heptadecene, 0.2296 g, was used with 0.0226 g of sulfated zirconia catalyst. A comparison of $^1$H NMR spectra shows the alkane/alkene ratio increases from 21.18 to 25.65 in the product.

The sulfated zirconia was prepared as disclosed in Oh J., et al., (2013) Appl Catal. A: Gen., 455, 164-171 and incorporated herein by reference. Namely, five grams zirconium isopropoxide was suspended in 20 ml n-propanol with vigorous stirring. Subsequently, 15 ml of a 0.5 M sulfuric acid solution was added dropwise over a period of 30 min. The resulting gel was stirred overnight, collected by filtration, washed with water and methanol, then dried under vacuum at 90° C. The resulting solid was calcined at 625° C. for 2 hr. Scanning Electron Microscope equipped with an Energy Dispersive Spectrometer indicated the product was 75.7 wt % Zr, 1.1 wt % S.

Example 50: Polymerization of Isomerized Heptadecene Made from Decarboxylation of 9-Cis-Octadecenoic Acid, at 250° C., 5 Weight % Catalyst This example was done by the same method as Example 49, with a temperature of 250° C. Heptadecene, 0.3483 g was used with 0.0173 g of sulfated zirconia catalyst. A comparison of $^1$H NMR spectra shows the alkane/alkene ratio increases from 21.18 to 28.97 in the product.

Example 51: Polymerization of Isomerized Heptadecene Made from Decarboxylation of 9-Cis-Octadecenoic Acid, at 250° C.

This Example was done by the same method as Example 49, with a temperature of 250° C. Heptadecene, 0.3295 g was used with 0.0328 g of sulfated zirconia catalyst. A comparison of $^1$H NMR spectra shows the alkane/alkene ratio increases from 21.18 to 48.44 in the product.

Example 52: Polymerization of Isomerized Heptadecene Made from Decarboxylation of 9-Cis-Octadecenoic Acid, at 250° C.

This Example was done by the same method as Example 49, with a temperature of 250° C. Heptadecene, 0.2961 g was used with a different catalyst of 0.0228 g of beta zeolite. The beta zeolite catalyst (Zeolyst) was activated by heating at 600° C. for 4 hours. A comparison of $^1$H NMR spectra shows the alkane/alkene ratio increases from 21.18 to 28.01 in the product.

As a control, polymerization at a temperature of 250° C. was conducted with 0.2509 g heptadecene with no added catalyst. A comparison of $^1$H NMR spectra shows the alkane/alkene ratio didn't significantly change, 21.18 in the starting material and 20.05 in the product.

Example 53: A Self Metathesis Experiment on Isomerized Heptadecene

Figure 66:
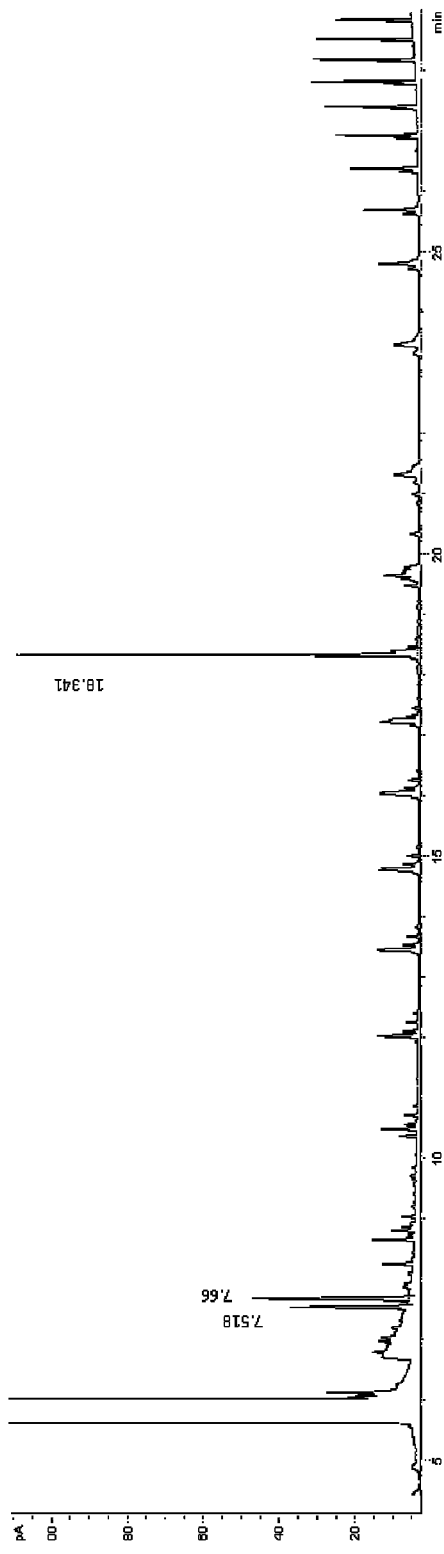
FIG. 66 is a GC-FID chromatogram of the self metathesis reaction of isomerized heptadecene as a function of elution time (minutes) showing a mixture of isomers of alkenes of various size.
Figure 67:
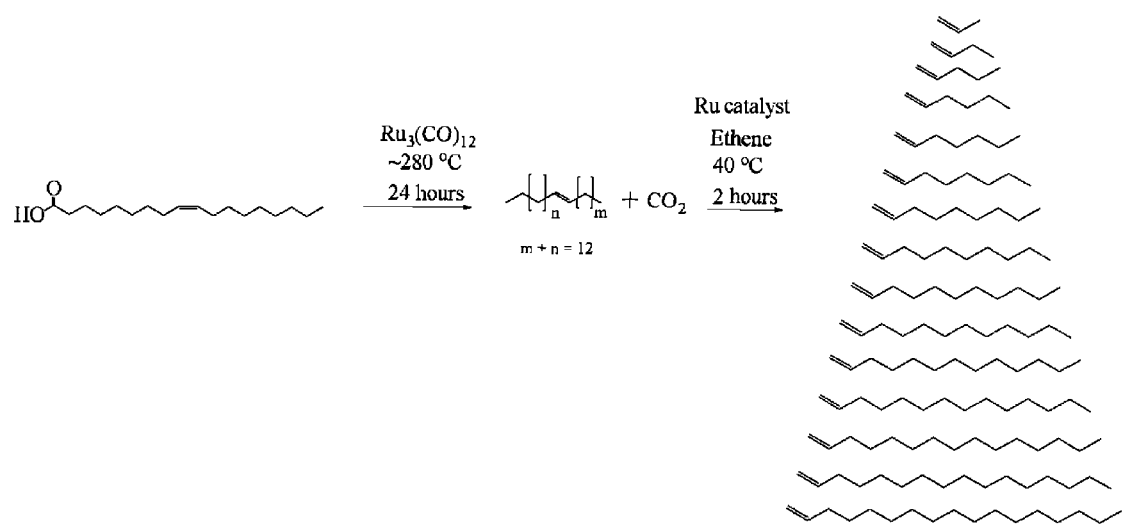
FIG. 67 is a depiction of an exemplar reaction scheme for the decarboxylation reaction followed by the cross metathesis with ethene to make a distribution of α-olefins.

Inside an inert atmosphere glovebox, 0.110 g of heptadecene isomers from Example 46, was mixed with 1 mL of a toluene solution that contained 0.001 g of Second Generation Grubbs catalyst. The vial was removed from the glovebox, and stirred on a hot plate at 35° C. for two hours. A toluene solution of butyl vinyl ether was added to quench the reaction. The GC-FID chromatogram, FIG. 66, shows a variety of compounds, expected from this reaction.

Figure 68:
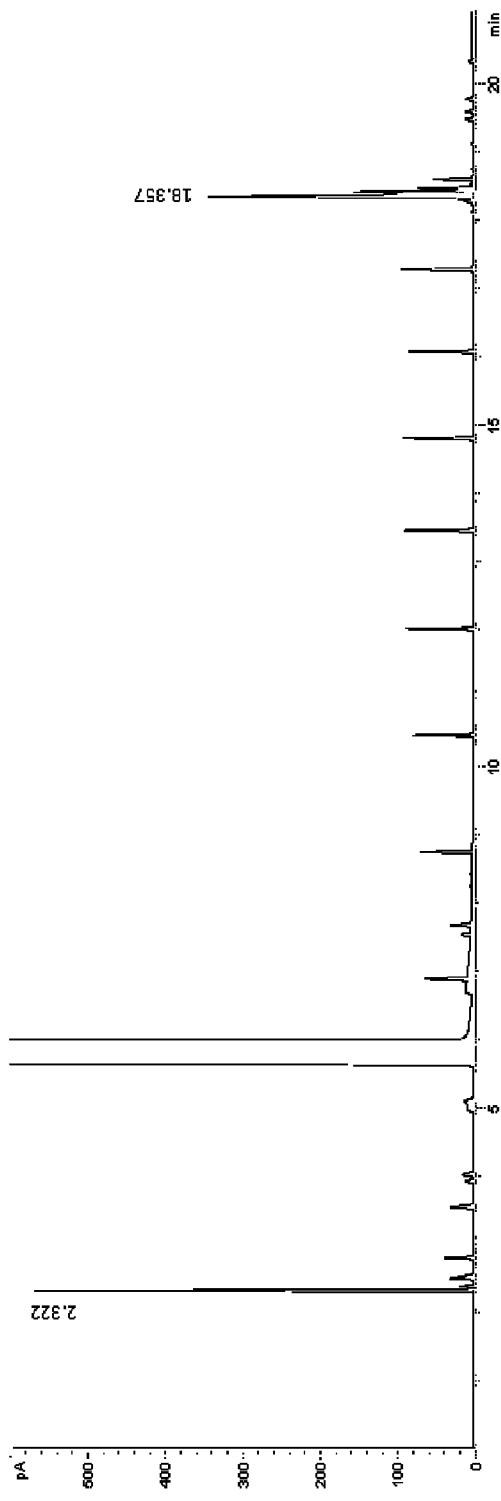
FIG. 68 is a GC-FID chromatogram of the cross metathesis reaction of isomerized heptadecene as a function of elution time (minutes) showing a mixture of isomers of alkenes of various size.
Figure 69:
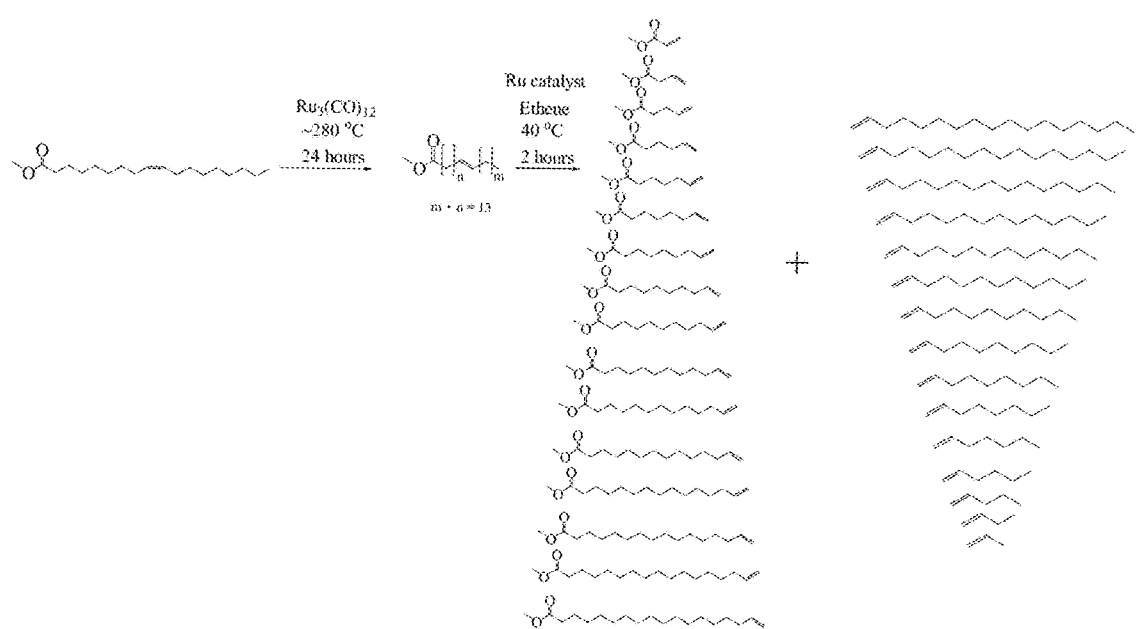
FIG. 69 is a depiction of an exemplar reaction scheme for the isomerization of methyl 9-cis-octadecenoate followed by the cross metathesis with ethene to make a plurality of alkene and ester compounds.

Example 54: An Ethylene Cross-Metathesis Experiment on Isomerized Heptadecene Inside an inert atmosphere glovebox, 0.108 g of heptadecene isomers from Example 46, was mixed with 10 mL of a toluene solution and transferred into a pressure reactor bottle. The bottle was removed from the drybox, purged with ethene and then pressurized to 88 PSI with ethene. Next, 1 mL of a toluene solution that contained 0.001 g of First Generation Grubbs catalyst was injected. The reaction was ran for 2 hours at 35° C., before quenching with a toluene solution of butyl vinyl ether. The GC-FID chromatogram, FIG. 68, shows a variety of compounds, primarily α-olefins.

Figure 70:
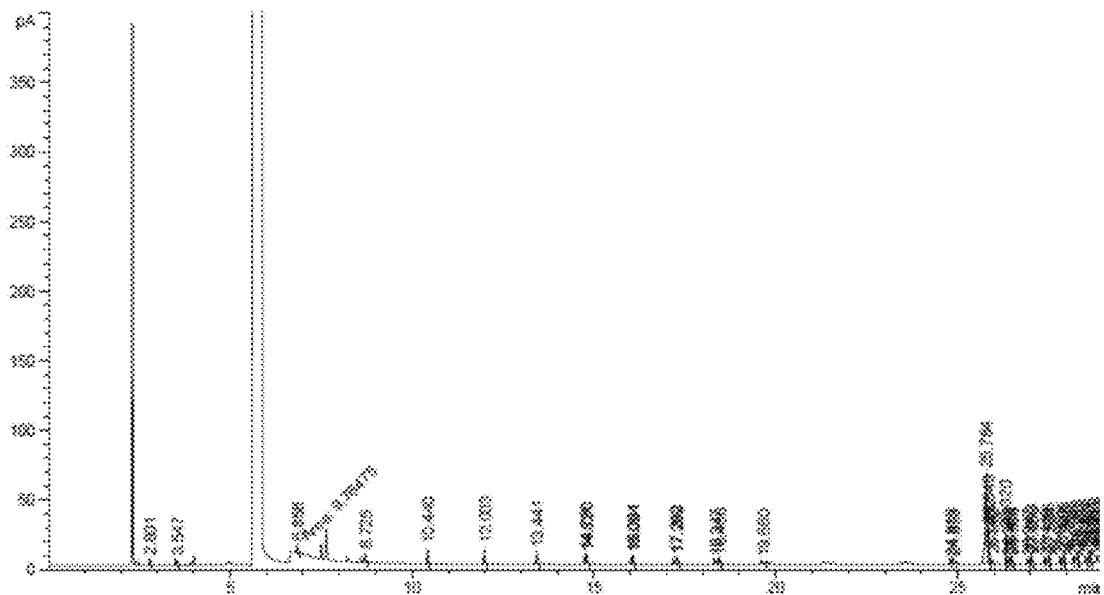
FIG. 70 is a GC-FID chromatogram of isomerized methyl cis-9-octadecene after a metathesis reaction with ethene as a function of elution time (minutes).

Example 55: A cross metathesis experiment on isomerized methyl octadecenoate This Example was done using the same method as Example 54. The isomerized methyl octadecenoate 0.118 g, was made in a similar manner to that from Example 17. The GC-FID chromatogram, FIG. 70, shows a variety of compounds, expected from this reaction.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). For instance, the isomerization of an alkene with a catalyst or catalyst precursor is determined in a inclusive manner.

While the invention has been described with reference to details of the illustrated embodiment, these details are not intended to limit the scope of the invention as defined in the appended claims.

The embodiment of the invention in which exclusive property or privilege is claimed is defined as follows:

1. A process for the production of a decarboxylated unsaturated organic compound, the process comprising contacting an unsaturated carboxylic acid in the presence of a catalyst or catalyst precursor containing a ruthenium carbonyl carboxylates at a temperature at which decarboxylation occurs and recovering the decarboxylated unsaturated organic compound product; wherein the number of C—C double bonds in said decarboxylated unsaturated organic compound is the same as in said carboxylic acid.

2. The process of claim 1 comprising the additional step of contacting an additional acid to said carboxylic acid in the presence of a catalyst or catalyst precursor.

3. The process of claim 2 wherein the acid is a monocarboxylic acid.

4. The process of claim 3 wherein the monocarboxylic acid is benzoic acid, cinnamic acid, propanoic, acid, undecanoic acid, acetic acid, stearic acid, or oleic acid.

5. The process of claim 1 wherein the decarboxylated unsaturated organic compound product is an olefin.

6. The process of claim 5 wherein the olefin is further subject to an oligomerization or a polymerization reaction.

7. The process of claim 5 wherein the decarboxylated unsaturated organic compound product is a mixture of internal and alpha-olefins.

8. The process of claim 5 wherein the decarboxylated unsaturated organic compound product is a conjugated internal olefin.

9. A process for the isomerization and decarboxylation of an unsaturated carboxylic acid, the process comprising contacting an unsaturated carboxylic acid in the presence of a catalyst or catalyst precursor containing a ruthenium carbonyl carboxylates at a temperature at which the isomerization and decarboxylation occurs and recovering the products which are isomerized and decarboxylated unsaturated olefins, wherein the C—C double bonds in said isomerized and decarboxylated unsaturated olefins are in different locations compared to said unsaturated carboxylic acid, and wherein the number of C—C double bonds in said isomerized and decarboxylated unsaturated olefins are the same as in said unsaturated carboxylic acid.

10. The process of claim 9 comprising the additional step of contacting an additional acid to said unsaturated fatty acid in the presence of a catalyst or catalyst precursor.

11. The process of claim 10 wherein the acid is a monocarboxylic acid.

12. The process of claim 11 wherein the monocarboxylic acid is benzoic acid, cinnamic acid, propanoic acid, undecanoic acid, acetic acid, stearic acid, or oleic acid.

13. The process of claim 9 wherein the isomerized and decarboxylated unsaturated organic compound product is an olefin.

14. The process of claim 13 wherein the isomerized and decarboxylated unsaturated organic compound product is a mixture of internal and alpha-olefins.

15. The process of claim 13 wherein the isomerized and decarboxylated unsaturated organic compound product is a conjugated internal olefin.

16. A process for the production of an isomerized unsaturated vegetable oil, the process comprising contacting a starting unsaturated vegetable oil in the presence of a catalyst or catalyst precursor containing a ruthenium carbonyl carboxylates at a temperature at which isomerization occurs and recovering the isomerized unsaturated vegetable oil product, wherein the C—C double bonds in said isomerized unsaturated vegetable oil are in different locations compared to said starting unsaturated vegetable oil, wherein the branching of said isomerized unsaturated vegetable oil is not increased compared to said starting unsaturated vegetable oil, and wherein the number of C—C double bonds in said isomerized unsaturated vegetable oil is the same as in said starting unsaturated vegetable oil; wherein said catalyst or catalyst precursor does not contain a phosphine ligand.

17. The process of claim 16 comprising the additional step of contacting an additional acid to said vegetable oil in the presence of a catalyst or catalyst precursor.

18. The process of claim 17 wherein the acid is a monocarboxylic acid.

19. The process of claim 18 wherein the monocarboxylic acid is benzoic acid, cinnamic acid, propanoic acid, undecanoic acid, acetic acid, stearic acid, or oleic acid.

20. The process of claim 16 wherein the isomerized vegetable oil is an olefin containing triglyceride.

21. The process of claim 20 wherein the isomerized vegetable oil product is a mixture of internal and alpha-olefin containing triglycerides.

22. The process of claim 20 wherein the isomerized vegetable oil product contains a conjugated internal olefin.

23. The process of claim 20, wherein said vegetable oil is soybean oil.

24. The process of claim 16 wherein the olefin is further subject to an oligomerization or a polymerization reaction.

* * * * *